(12) United States Patent
Dresser et al.

(10) Patent No.: US 10,914,941 B2
(45) Date of Patent: Feb. 9, 2021

(54) ELECTROMAGNETIC RADIATION BEAM SCANNING SYSTEM AND METHOD

(71) Applicant: Avava, Inc., Boston, MA (US)

(72) Inventors: Charles Holland Dresser, Wayland, MA (US); Jayant Bhawalkar, Auburndale, MA (US); Joseph Ting, Acton, MA (US)

(73) Assignee: Avava, Inc., Waltham, MA (US)

( * ) Notice: Subject to any disclaimer, the term of this patent is extended or adjusted under 35 U.S.C. 154(b) by 140 days.

(21) Appl. No.: 16/219,801

(22) Filed: Dec. 13, 2018

(65) Prior Publication Data

US 2019/0187461 A1 Jun. 20, 2019

Related U.S. Application Data

(60) Provisional application No. 62/598,854, filed on Dec. 14, 2017, provisional application No. 62/598,865, filed on Dec. 14, 2017.

(51) Int. Cl.
*G02B 26/08* (2006.01)
*G02B 26/10* (2006.01)
(Continued)

(52) U.S. Cl.
CPC ....... *G02B 26/128* (2013.01); *G02B 21/0012* (2013.01); *G02B 21/0048* (2013.01);
(Continued)

(58) Field of Classification Search
CPC .... G02B 26/12; G02B 26/128; G02B 26/101; G02B 26/105; G02B 21/0012;
(Continued)

(56) References Cited

U.S. PATENT DOCUMENTS 3,779,094 A 12/1973 La
6,193,710 B1 2/2001 Lemberg
(Continued)

FOREIGN PATENT DOCUMENTS

CN 204637343 U 9/2015
DE 102011121459 A1 6/2013
(Continued)

OTHER PUBLICATIONS

Balu et al. (Aug. 2017) "In vivo multiphoton-microscopy of picosecond-laser-induced optical breakdown in human skin," Lasers Surg Med. 49(6):555-562. Accessible on the Internet at URL: https://www.ncbi.nlm.nih.gov/pubmed/28333369.
(Continued)

*Primary Examiner* — Mustak Choudhary
(74) *Attorney, Agent, or Firm* — Mintz Levin Cohn Ferris Glovsky and Popeo, P.C.

(57) ABSTRACT

An electromagnetic beam scanning system and corresponding method of use is provided. The system includes a motor, a reciprocating mechanism, and a focus optic. The motor is configured to generate a rotational movement. The reciprocating mechanism is operatively coupled with the motor and configured to convert the rotational movement to a reciprocating movement including a plurality of strokes along a first scanned axis. The reciprocating movement has a constant speed over a portion of at least one stroke of the plurality of strokes. The focus optic is operatively coupled to the reciprocating mechanism such that the focus optic moves experiences the reciprocating movement of the reciprocating mechanism. The focus optic is configured to focus an electromagnetic radiation (EMR) beam incident upon the focus optic to a focus along an optical axis substantially orthogonal to the first scanned axis.

20 Claims, 54 Drawing Sheets

(51) Int. Cl.
*G02B 26/12* (2006.01)
*G02B 21/00* (2006.01)
*G06K 7/10* (2006.01)
*H01S 3/11* (2006.01)

(52) U.S. Cl.
CPC ......... *G02B 26/101* (2013.01); *G02B 26/105* (2013.01); *G02B 26/12* (2013.01); *G06K 7/10613* (2013.01); *H01S 3/11* (2013.01)

(58) Field of Classification Search
CPC . G02B 21/0048; G06K 7/10613; A61F 9/008; A61F 9/00804; A61F 9/00817; A61B 18/04; A61B 18/18; A61B 18/20; A61B 18/24; A61B 18/203; A61B 18/1477; B23K 26/082; H01S 3/11; A61M 5/007; A61M 5/1422; A61M 5/3153
USPC .......... 359/199.3, 200.7, 203.1, 210.1, 210.2
See application file for complete search history.

(56) References Cited

U.S. PATENT DOCUMENTS

| | | | |
|---|---|---|---|
| 6,537,270 | B1 | 3/2003 | Elbrecht et al. |
| 7,201,748 | B2* | 4/2007 | Karino .................. A61B 18/24 606/14 |
| 7,625,371 | B2* | 12/2009 | Morris ............... A61B 18/1477 606/41 |
| 2002/0022829 | A1* | 2/2002 | Nagase .................. A61B 18/20 606/12 |
| 2002/0161357 | A1* | 10/2002 | Anderson ............ A61B 18/203 606/9 |
| 2004/0009540 | A1 | 1/2004 | Soohoo et al. |
| 2006/0276778 | A1 | 12/2006 | Sink |
| 2007/0239147 | A1 | 10/2007 | Manstein et al. |
| 2008/0015555 | A1 | 1/2008 | Manstein et al. |
| 2008/0067251 | A1* | 3/2008 | Yoshimoto ........... B23K 26/082 235/462.32 |
| 2008/0161888 | A1 | 7/2008 | Hsia |
| 2008/0186591 | A1 | 8/2008 | Altshuler et al. |
| 2008/0208104 | A1 | 8/2008 | Bragagna et al. |
| 2008/0234669 | A1 | 9/2008 | Kauvar |
| 2008/0287801 | A1 | 11/2008 | Magnin et al. |
| 2009/0147807 | A1* | 6/2009 | Lai ....................... H01S 3/0675 372/6 |
| 2009/0254073 | A1 | 10/2009 | Davenport et al. |
| 2009/0261239 | A1 | 10/2009 | Clancy et al. |
| 2010/0082019 | A1 | 4/2010 | Neev |
| 2010/0217248 | A1 | 8/2010 | Mirkov et al. |
| 2012/0016239 | A1 | 1/2012 | Barthe et al. |
| 2012/0283711 | A1 | 11/2012 | Liu et al. |
| 2012/0296322 | A1 | 11/2012 | Yamazaki et al. |
| 2012/0310235 | A1 | 12/2012 | Paithankar et al. |
| 2014/0005644 | A1 | 1/2014 | Karni et al. |
| 2014/0100489 | A1 | 4/2014 | Altshuler et al. |
| 2014/0243804 | A1 | 8/2014 | Lukac et al. |
| 2015/0051487 | A1 | 2/2015 | Uber et al. |
| 2015/0051593 | A1 | 2/2015 | Johnson et al. |
| 2015/0062320 | A1 | 3/2015 | Tunnell |
| 2015/0133848 | A1 | 5/2015 | Bratchenia et al. |
| 2015/0150629 | A1 | 6/2015 | Anderson et al. |
| 2015/0202007 | A1 | 7/2015 | Manstein et al. |
| 2015/0238258 | A1 | 8/2015 | Palero et al. |
| 2016/0199132 | A1 | 7/2016 | Anderson et al. |
| 2018/0177550 | A1 | 6/2018 | Anderson et al. |

FOREIGN PATENT DOCUMENTS

| | | |
|---|---|---|
| JP | 2003185584 A | 7/2003 |
| WO | 2004000419 A1 | 12/2003 |
| WO | 2005007003 A1 | 1/2005 |
| WO | 2007134257 A2 | 11/2007 |
| WO | 2008001284 A2 | 1/2008 |
| WO | 2012098548 A1 | 7/2012 |
| WO | 2017130185 A2 | 8/2017 |

OTHER PUBLICATIONS

Bril (May 2010) "Fractional Laser Skin Treatment Using Diffractive Optics," Photonics Media. 1 page. Accessible on the Internet at URL: https://www.photonics.com/Article.aspx?AID=42337.

Fotona (2003) "Dermatological Handpiece—Hexagonal Laser Beam Shape for Uniform Coverage," Fotona Technology. 2 pages. Accessible on the Internet at URL: https://www.fotona.com/media/aurora/dokumenti/2011/12/90683_1_0_handpiece_r_hx_leaflet.pdf.

Grossinger et al. (2018) "Recent Optical Solutions with Diffractive Optical Technology," Ben-Gurrion University. 30 pages. Accessible on the Internet at URL: https://physics.bgu.ac.il/~gtelzur/teaching/comphy/Presentations/TamirGrossinger.pdf.

Hong et al. (2009) "Maskless multibeam laser irradiation enables large-area nanostructure fabrication," SPIE Proceedings. Accessible on the Internet at URL: http://spie.org/newsroom/1594-maskless-multibeam-laser-irradiation-enables-large-area-nanostructure-fabrication?SSO=1.

Reichel et al. (2009) "Glass diffractive optical beam shaper for laser applications," DGaO Proceedings. 2 pages. Accessible on the Internet at URL: https://www.dgao-proceedings.de/download/110/110_a22.pdf.

International Search Report with Written Opinion corresponding to International Patent Application No. PCT/US2018/065538, dated Feb. 22, 2019, 17 pages.

* cited by examiner

ELECTROMAGNETIC RADIATION BEAM SCANNING SYSTEM AND METHOD

CROSS-REFERENCE TO RELATED APPLICATIONS

This application claims the benefit of U.S. Provisional Application No. 62/598,854, entitled "Scanning Systems for EMR-Based Tissue Treatment," filed Dec. 14, 2017, and U.S. Provisional Application No. 62/598,865, entitled "Alternative Scanning Systems For EMR-Based Tissue Treatment," filed Dec. 14, 2017. The entirety of each of these applications is incorporated by reference.

FIELD

The present disclosure relates generally to methods, systems, and devices for laser beam scanning.

BACKGROUND

Scanning of electromagnetic radiation (EMR) (e.g., laser) beams is required for many technical applications, including energy based medical and cosmetic treatments. In many cases it is advantageous for a beam to be scanned at a speed that is as fast as possible, so that radiation may be delivered as quickly as possible reducing processing time (e.g., treatment time). It is also often advantageous for the speed at which the beam is scanned to be as constant as possible, in order that radiation beam consistently delivered over a scan path. Where the speed of scanning varies, the beam delivers more radiation to locations along the path where the scan speed is slower and less radiation to locations along the path where the scan speed is higher. The amount of variation in scan speed varies on the application.

As new applications employing electromagnetic radiation grow, new beam scanning systems and methods are needed to accommodate these new applications. For example, treating epidermal pigmentation (e.g., Solar Lentigo) has long been performed successfully with EMR devices and methods (e.g., lasers and intense pulsed light). However, successful treatment of some dermal pigmentation (e.g., Melasma) conditions with EMR has remained impractical.

Melasma is an example of one skin disorder of unknown etiology that causes a blotchy hyperpigmentation, often in the facial area. This condition is more common in women than in men. Although the specific cause(s) of melasma may not be well-understood, the pigmented appearance of melasma can be aggravated by certain conditions such as pregnancy, sun exposure, certain medications, such as, e.g., oral contraceptives, hormonal levels, genetics, etc. Exemplary symptoms of melasma include dark, irregularly-shaped patches or macules, which are commonly found on the upper cheek, nose, upper lip, and forehead. These patches often develop gradually over time. Melasma does not appear to cause any other symptoms, nor have other detrimental effects, beyond the cosmetic discoloration.

Unlike many pigmented structures that are typically present in the epidermal region of skin (e.g., at or near the tissue surface), dermal (or deep) melasma is often characterized by widespread presence of melanin and melanophages (including, e.g., excessively-pigmented cells) in portions or regions of the underlying dermis. Accordingly, treatment of dermal melasma (e.g., lightening of the appearance of darkened pigmented regions) can be particularly challenging because of the presence of the greater difficulty in accessing and affecting such pigmented cells and structures located deeper within the skin. Accordingly, conventional skin rejuvenation treatments such as facial peels (laser or chemical), dermabrasion, topical agents, and the like, which primarily affect the overlying epidermis, may not be effective in treating dermal melasma.

Various conditions can be treated with the application of light or optical energy of certain wavelengths. Many challenges exist in delivering the energy to the appropriate target structure (e.g., tissue such as the skin) without damaging tissue structures adjacent to the target structure. These challenges include delivery of energy at an appropriate wavelength with sufficient fluence and focus as well as the ability to effectively and efficiently scan the target structure with the light or optical energy.

It has been observed that application of light or optical energy of certain wavelengths can be strongly absorbed by pigmented cells, thereby damaging them. However, an effective treatment of dermal melasma using optical energy introduces several obstacles. For example, pigmented cells in the dermis must be targeted with sufficient optical energy of appropriate wavelength(s) to disrupt or damage them, which may release or destroy some of the pigmentation and reduce the pigmented appearance. However, such energy can be absorbed by pigment (e.g., chromophores) in the overlying skin tissue, such as the epidermis and upper dermis. This near-surface absorption can lead to excessive damage of the outer portion of the skin, and insufficient delivery of energy to the deeper dermis to affect the pigmented cells therein. Moreover, thermal injury to melanocytes located in the basal layer of the epidermis can trigger an increase in the production of melanin.

Fractional approaches have been developed that involve application of optical energy to small, discrete treatment locations on the skin that are separated by healthy tissue to facilitate healing. Accurately targeting the treatment locations (e.g., located in dermal layer) with desirable specificity while avoiding damage to healthy tissue around the treatment location (e.g., in the epidermal layer) can be challenging. This requires, for example, an optical system with high numerical aperture (NA) for focusing a laser beam to a treatment location. The high NA optical system delivers a sufficiently high fluence (i.e., energy density) to the dermis, while maintaining a sufficiently low out of focus fluence in the epidermis. U.S. Patent Application Publication No. 2016/0199132, entitled "Method and Apparatus for Treating Dermal Melasma" has illustrates this technique to be advantageous for treatment of dermal pigmentation, including Melasma, in research settings. However, currently available beam scanning systems and methods preclude this treatment technique from widespread adoption. It has long been the hope of those suffering with pigmentary conditions, such as Melasma, and their caregivers that an EMR-based treatment for their condition be made widely available.

SUMMARY

Therefore, it is desirable to develop an optical system that can have high numerical aperture, and is capable of scanning over large affected regions. Further, it can be desirable that the optical system can treat the affected region in a reasonable time duration (e.g., less than an hour). Also, in order to deliver a consistent amount of radiation it is advantageous for the optical system to scan at a consistent rate. Furthermore, it can be desirable that the optical system includes an interface that can, for example, establish a robust contact with the treatment region, stabilize the treatment region, cool the treatment region, and the like.

Accordingly, improved methods, systems, and devices for EMR (e.g., laser) beam scanning are provided.

In an embodiment, an electromagnetic beam scanning system is provided. The system includes a motor, a reciprocating mechanism, and a focus optic. The motor is configured to generate a rotational movement. The reciprocating mechanism is operatively coupled with the motor and configured to convert the rotational movement to a reciprocating movement including a plurality of strokes along a first scanned axis. The reciprocating movement has a constant speed over a portion of at least one stroke of the plurality of strokes. The focus optic is operatively coupled to the reciprocating mechanism such that the focus optic moves experiences the reciprocating movement of the reciprocating mechanism. The focus optic is configured to focus an electromagnetic radiation (EMR) beam incident upon the focus optic to a focus along an optical axis substantially orthogonal to the first scanned axis.

In another embodiment, the constant speed is within 50% of a desired constant speed and the portion of the stroke is at least 10% of the stroke.

In another embodiment, the system also includes an electromagnetic radiation source and an optical system. The electromagnetic radiation source is configured to generate the EMR beam. The optical system is configured to direct the EMR beam incident upon the focus optic.

In another embodiment, at least one element of the optical system experiences the reciprocating movement.

In another embodiment, the EMR source is configured to operate in a pulsed mode according to a predetermined repetition rate, and a relationship between the repetition rate of the EMR source and the constant speed of the reciprocating movement determines a nominal pitch between sequential pulsed focuses along the first scanned axis.

In another embodiment, the system further includes an intermittent mechanism. The intermittent mechanism is operatively coupled with the reciprocating mechanism, and configured to introduce an intermittent movement along a second scanned axis that is substantially orthogonal to the first scanned axis. The focus optic is operably coupled to the intermittent mechanism such that the focus optic experiences the intermittent movement.

In another embodiment, the intermittent mechanism is configured to introduce the intermittent movement according to a position of the reciprocating movement.

In another embodiment, the intermittent movement is introduced when the reciprocating movement is generally at a position corresponding to at least one of: a beginning of the stroke, a middle of the stroke, and an end of the stroke.

In another embodiment, the system additionally includes a housing disposed between the focus optic and the focus along the optical axis that is configured to contact a surface of a target tissue via a contacting surface; wherein the focus is located down beam of the surface of the target tissue.

In another embodiment, the contacting surface is configured to cool the target tissue.

In another embodiment, the housing includes one or more of a pressure sensor, a contact sensor, and a temperature sensor.

In a further embodiment, a method for electromagnetic beam scanning is provided. The method includes generating a rotational movement. The method also includes converting the generated rotational movement into a reciprocating movement including a plurality of strokes along a first scanned axis. The reciprocating movement has a constant speed over a portion of at least one stroke of the plurality of strokes. The method further includes moving a focus optic according to the reciprocating movement, wherein the focus optic is configured to focus an electromagnetic radiation (EMR) beam incident upon the focus optic to a focus along an optical axis substantially orthogonal to the first scanned axis.

In another embodiment, the constant speed is within 50% of a desired constant speed and the portion of the stroke is at least 10% of the stroke.

In another embodiment, the method includes generating the EMR beam, and directing, using an optical system, the EMR beam incident upon the focus optic.

In another embodiment, the method includes moving at least one element of the optical system according to the reciprocating movement.

In another embodiment, the method includes pulsing the EMR beam according to a predetermined repetition rate. A relationship between the repetition rate and the constant speed determines a nominal pitch between sequential pulsed laser focuses along the first scanned axis.

In another embodiment, the method includes introducing an intermittent movement along a second scanned axis that is substantially orthogonal to the first scanned axis, and moving the focus optic according to the intermittent movement.

In another embodiment, the intermittent movement is introduced according to a position of the reciprocating movement.

In another embodiment, the intermittent movement is introduced when the reciprocating movement is generally at a position corresponding to at least one of: a beginning of the stroke, a middle of the stroke, and an end of the stroke.

In another embodiment, the method includes contacting a surface of a target tissue between the focus optic and the focus along the optical axis with a contacting surface of a housing, wherein the focus is located down beam of the surface of the target tissue.

In another embodiment, the method includes cooling the target tissue using the contacting surface.

In another embodiment, the method includes sensing, using a sensor located within the housing, one or more variables of the target tissue. The one or more variables can include at least one of a pressure, a contact between the contacting surface and the target tissue, and a temperature.

BRIEF DESCRIPTION OF DRAWINGS

Embodiments of the present disclosure will be more fully understood from the following detailed description taken in conjunction with the accompanying drawings, in which.

Figure 1:
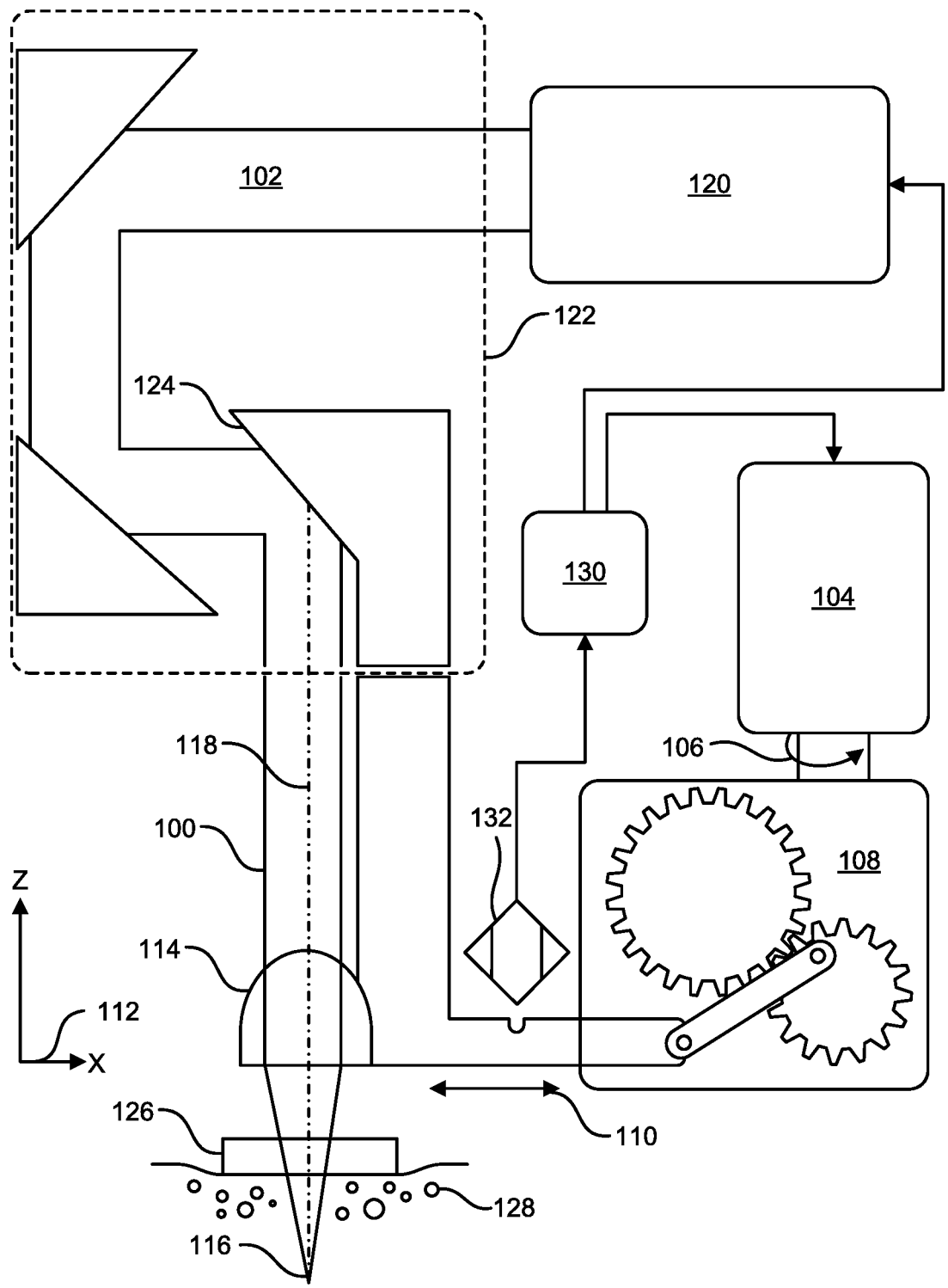
FIG. 1 schematically represents a one-dimensional (1D) beam scanning system, according to some embodiments.

It is noted that the drawings are not necessarily to scale. The drawings are intended to depict only typical aspects of the subject matter disclosed herein, and therefore should not be considered as limiting the scope of the disclosure. Those skilled in the art will understand that the systems, devices, and methods specifically described herein and illustrated in the accompanying drawings are non-limiting exemplary embodiments and that the scope of the present invention is defined solely by the claims.

DETAILED DESCRIPTION

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Embodiments of the disclosure are discussed in detail below with respect to treatment of pigmentary conditions of the skin, such as melasma, to improve the appearance of such a pigmentary condition. However, the disclosed embodiments can be employed for treatment of other pigmentary and non-pigmentary conditions and other tissue and non-tissue targets without limit. Examples of pigmentary conditions can include, but are not limited to, post inflammatory hyperpigmentation, dark skin surrounding eyes, dark eyes, café au lait patches, Becker's nevi, Nevus of Ota, congenital melanocytic nevi, freckles/lentigo, hemosiderin rich structures, pigmented gallstones, lutein, zeaxanthin, rhodopsin, carotenoid, biliverdin, bilirubin and hemoglobin rich structures, and tattoo-containing tissue. Examples of non-pigmentary conditions can include, but are not limited to, hair follicles, hair shaft, vascular lesions, infectious conditions, sebaceous glands, acne, and the like.

Further, in the present disclosure, like-named components of the embodiments generally have similar features, and thus within a particular embodiment each feature of each like-named component is not necessarily fully elaborated upon. Additionally, to the extent that linear or circular dimensions are used in the description of the disclosed systems, devices, and methods, such dimensions are not intended to limit the types of shapes that can be used in conjunction with such systems, devices, and methods. A person skilled in the art will recognize that an equivalent to such linear and circular dimensions can easily be determined for any geometric shape. Sizes and shapes of the systems and devices, and the components thereof, can depend at least on the anatomy of the subject in which the systems and devices will be used, the size and shape of components with which the systems and devices will be used, and the methods and procedures in which the systems and devices will be used.

In general, high numerical aperture (NA) optical scanning systems are described that can focus electromagnetic radiation (EMR) (e.g., a laser beam) to a treatment region in a tissue. The focused laser beam can deliver optical energy to the treatment region without harming the surrounding tissue. The delivered optical energy can, for example, disrupt pigmented chromophores and/or targets in a treatment region of the dermal layer of the skin, without affecting the surrounding regions (e.g., overlying epidermal layer, other portions of the dermal layer, and the like) or within other pigmented target areas of the skin or tissue surrounded by unaffected and non-targeted areas. In other implementations, the delivered optical energy can cause tattoo removal or alteration, or hemoglobin-related treatment.

Exemplary methods and devices for treating skin conditions with light or optical energy are disclosed in U.S. Patent Application Publication No. 2016/0199132, entitled "Method and Apparatus for Treating Dermal Melasma," and U.S. Provisional Application No. 62/438,818, entitled "Method and Apparatus for Selective Treatment of Dermal Melasma," each of which is incorporated by reference herein in its entirety.

In general, systems and corresponding methods are provided for treatment of pigmentary conditions in tissues. As discussed in greater detail below, the disclosed systems and methods employ electromagnetic radiation (EMR), such as laser beams, to deliver predetermined amounts of energy to a target tissue. The EMR can be focused to a focal region and the focal region can be translated or rotated in any direction with respect to the target tissue. The predetermined amount of radiation can be configured to thermally disrupt or otherwise damage portions of the tissue exhibiting the pigmentary condition. In this manner, the predetermined amount of energy can be delivered to any position within the target tissue for treatment of the pigmentary condition such as to improve the appearance thereof.

For various applications involving the delivery of EMR to a target, including for the treatment of tissue, it is important to deliver a constant amount of radiation. To do so, it is advantageous for the optical system to scan at a constant rate. Described below are exemplary systems that implement a constant or substantially constant scan rate.

FIG. 1 schematically represents a system 100 for scanning an electromagnetic radiation (EMR) beam 102 according to some embodiments. A motor 104 generates a rotational movement 106. The motor 104 is operatively coupled to a reciprocating mechanism 108, such that the rotational movement 106 drives the reciprocating mechanism 108. The reciprocating mechanism 108 converts the rotational movement 106 into a reciprocating movement 110 that acts linearly generally along a first scanned axis 112 (e.g., an x-axis). According to some embodiments, the reciprocating mechanism includes one or more of the following: a cam and follower, a crank and slider, a Scotch yoke, and a multi-bar linkage. According to some embodiments, the reciprocating movement 110 moves with a plurality of strokes (e.g., two strokes, a forward stroke and a backward stroke). Typically, the reciprocating mechanism 108 is configured to provide the reciprocating movement 110 with a constant speed. Said another way, the reciprocating movement 110 has a velocity profile that is substantially flat over some portion of at least one stroke.

Embodiments of the constant speed can adopt a predetermined or desired constant speed. For instance, the desired constant speed can be selected from the range of about 2 mm/s to about 5 m/s. In certain embodiments, the constant speed can be a selected percentage of the desired constant speed. As an example, the selected percentage can be selected from the range of about 5% to about 95% of the desired constant speed (e.g., about 50%).

The portion of the stroke of the reciprocating movement 110 over which constant speed is provided can vary. For instance, the portion of the stroke having constant speed can be selected from the range of about 5% to about 95% (e.g., at least about 10%).

A focus optic 114 is operatively coupled to the reciprocating mechanism 108, such that it experiences and moves according to the reciprocating movement 110. The focus optic 114 is configured to focus the EMR beam 102 to a focus 116 along an optical axis 118. The reciprocating movement 110 of the focus optic 114 thereby moves the focus 116 and the optical axis 118 along the first scanned axis 112.

According to some embodiments, the EMR beam 102 is generated by an electromagnetic radiation (EMR) source 120. Examples of EMR sources are described in detail below. The EMR beam 102 is delivered from the EMR source 120 and directed incident upon the focus optic 114 by an optical system 122. Typically, the optical system 122 comprises one or more reflective and/or transmissive optics. According to some embodiments, The optical system 122 comprises one or more dynamic optical elements 124 that move. For example, the dynamic optical element 124 in the form of a reflector placed along the optical axis 118, and mechanically affixed to the focus optic 114, therefore experiences and moves according to the reciprocating movement 110. As discussed in greater detail below, the EMR source 120 can be configured to operate in a pulsed mode according to a predetermined repetition rate. A relationship between the repetition rate of the EMR source 12- and the constant speed of the reciprocating movement 110 can determine a nominal pitch between sequential pulsed focuses along the first scanned axis 112.

According to some embodiments, a housing 126 is disposed between the focus optic 114 and the focus 116 along the optical axis. The housing 126 is configured to contact a target surface, e.g., a surface of a target tissue 128, via a contacting surface. As shown, the focus 116 is positioned down beam of the surface of the target tissue 128. The housing 126 is described in greater detail below. In one embodiment, the contacting surface can be configured to cool the target tissue 128. In another embodiment, one or more sensors (e.g., a pressure sensor, a contact sensor, a temperature sensor, etc.) can be located within the housing and configured to measure one or more variables of the target tissue. The one or more variables can include at least one pressure, contact between the contacting surface and the target tissue, and temperature According to some embodiments, a controller 130 is used to control one or more of the motor 104, the reciprocating mechanism 108, and the EMR source 120. In some versions, the controller 130 takes input from one or more sensors 132 that measure at least one of the rotational movement 106 and the reciprocating movement 110.

Figure 2:
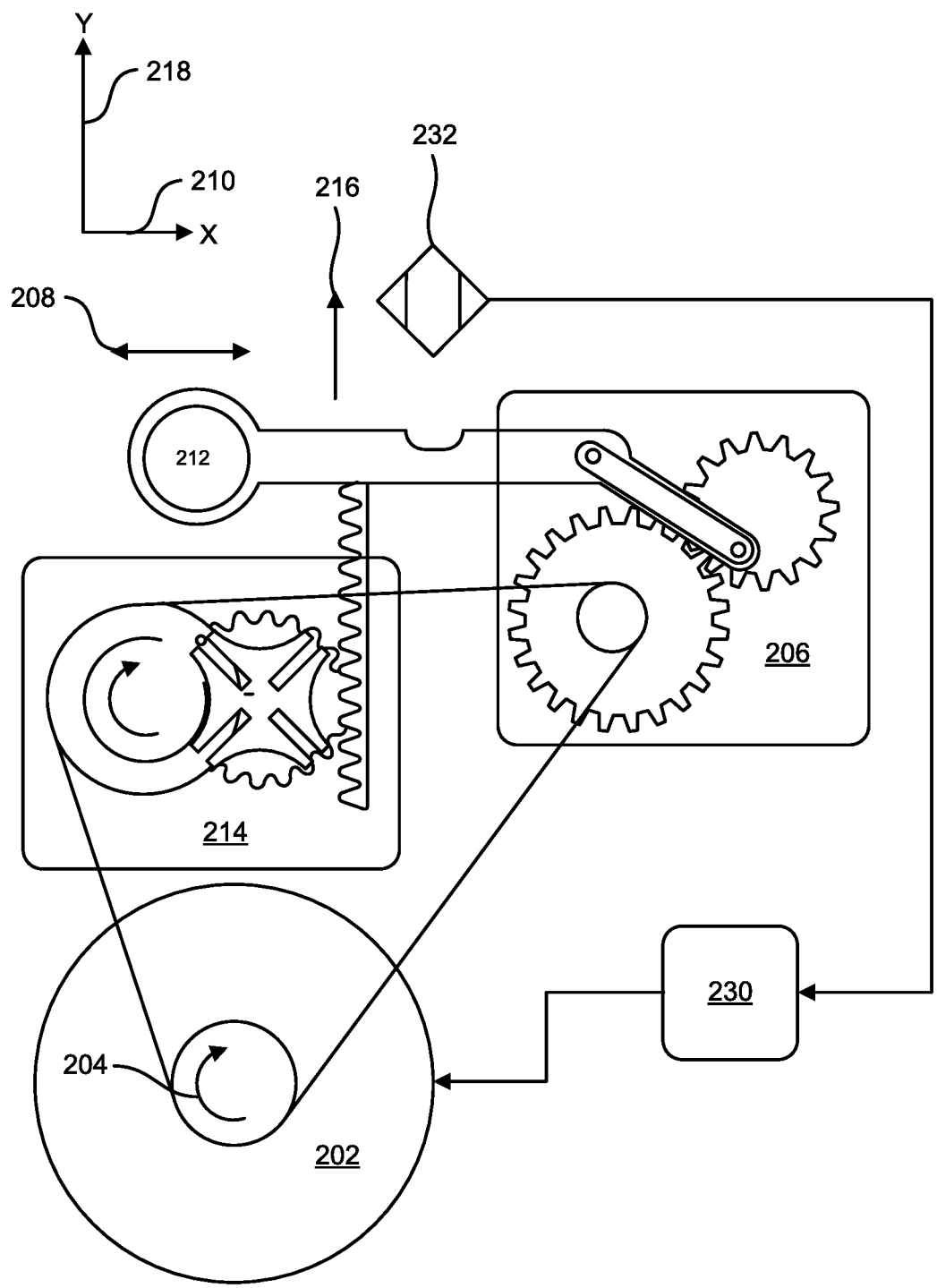
FIG. 2 schematically represents a two-dimensional (2D) beam scanning system, according to some embodiments.

FIG. 2 schematically represents a system 200 that scans an electromagnetic radiation (EMR) beam in two axes. A motor 202 generates and delivers a rotational movement 204 to a reciprocating mechanism 206 that converts the rotational movement 204 to a reciprocating movement 208 along a first scanned axis 210. According to some embodiments, the reciprocating movement 208 comprises a linear stroke and has a constant velocity over a portion of the linear stroke. A focus optic 212 is mechanically affixed to an output of the reciprocating mechanism 206, such that it experiences and moves according to the reciprocating movement 208. An intermittent mechanism 214 is operatively coupled with the reciprocating mechanism 206. The intermittent mechanism 214 outputs an intermittent movement 216 intermittently. According to some embodiments, the intermittent mechanism comprises one or more of: a ratchet mechanism, a Geneva wheel mechanism, a cam mechanism, and an intermittent gear mechanism. According to some embodiments, the intermittent movement 216 is linear and acts generally along a second scanned axis 218, which is generally orthogonal to the first scanned axis 210.

According to some embodiments, the intermittent mechanism 214 is configured to (e.g., timed to) introduce the intermittent movement 216 when the reciprocating movement 208 is at or near a specific location, for example at a beginning of a stroke, a middle of a stroke, or an end of a stroke.

According to some embodiments, a controller 230 is used to control one or more of the motor 202, the reciprocating mechanism 206, and the intermittent mechanism 214. In some versions, the controller 230 takes input from one or more sensors 232 that measure at least one of the rotational movement 204, the reciprocating movement 208, and the intermittent movement 216.

Figure 3A:
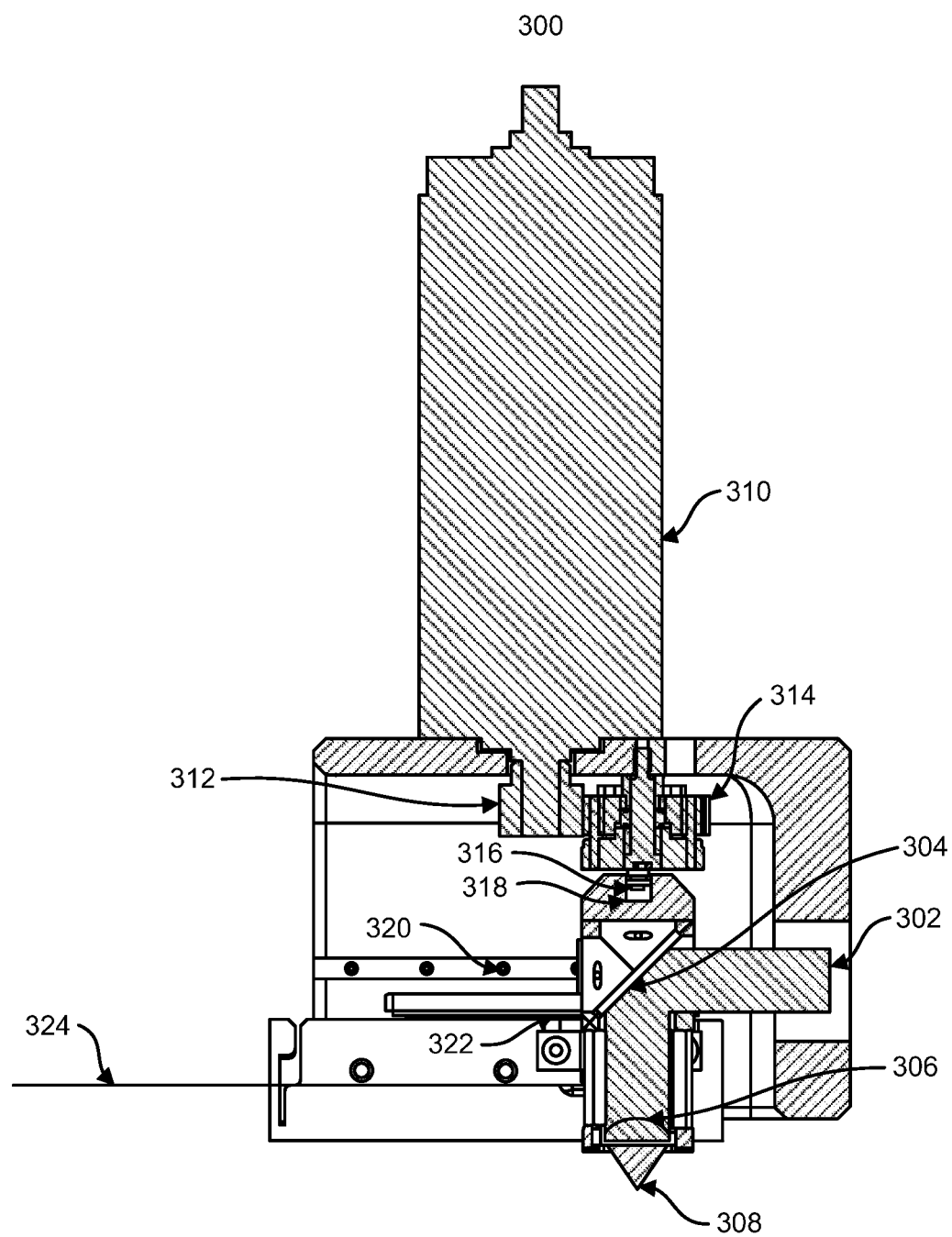
FIG. 3A is a cross-sectional view of an exemplary beam scanning system, according to some embodiments.

FIG. 3A illustrates a cross-sectional view of an exemplary system 300 for scanning an electromagnetic radiation (EMR) beam 302 in a single axis according to some embodiments. The EMR beam 302 enters the system 300 from the right and is reflected by a mirror 304. The mirror 304 directs the EMR beam 302 incident a focus optic (e.g., objective) 306. The focus optic 306 focuses the EMR beam 302 to a focus 308. A motor 310 drives a first non-circular gear 312 (e.g., an elliptical bilobe gear). The first non-circular gear 312 meshes and in turn drives a second non-circular gear 314. The second non-circular gear 314 is affixed to an eccentric pin 316. The eccentric pin 316 rides within a yoke 318. The yoke 316 is attached to the mirror 304, the focus optic 306, and a carriage that rides on a linear rail 320. The eccentric pin 316, the yoke 318, and the rail 320 are arranged to convert rotational movement of the eccentric pin 316 into linear reciprocating movement (e.g., such as by a Scotch yoke mechanism). According to some embodiments, the eccentric pin 316 comprises a bearing to reduce friction forces between the pin 316 and the yoke 318 (e.g., a rolling Scotch yoke pseudo-mechanism). According to some embodiments, a linear encoder is used to sense the linear reciprocating movement. A magnetic strip 322 (e.g., PN: MS05BM040AM010 from RLS Merilna tehnika d.o.o. of Komenda, Slovenia) is shown attached to the yoke 318. A magnetic encoder sensor (e.g., PN: RLM2ICAD40B15A00 from RLS Merilna tehnika d.o.o. of Komenda, Slovenia) is statically held relative the magnetic strip 322 and senses movement of the magnetic strip. According to some embodiments, a relative position of the yoke 318 is derived from counting sensed pulses of the magnetic strip and a direction of movement of the yoke 318 is derived from quadrature encoding. According to some embodiments, the linear encoder communicates one or more signals to a controller via a connection 324.

Figure 3B:
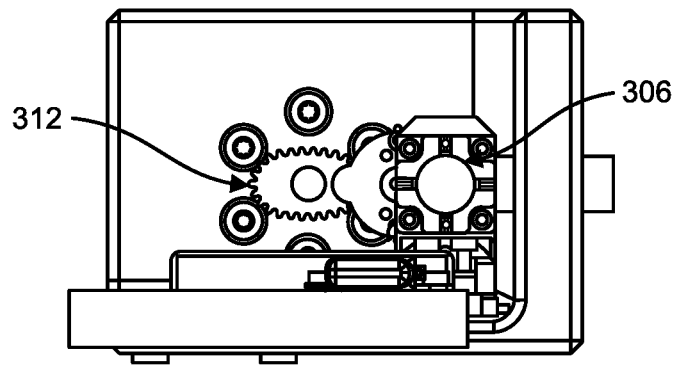
FIGS. 3B-3D are bottom views of an exemplary beam scanning system as it traverses a scan path, according to some embodiments.
Figure 3C:
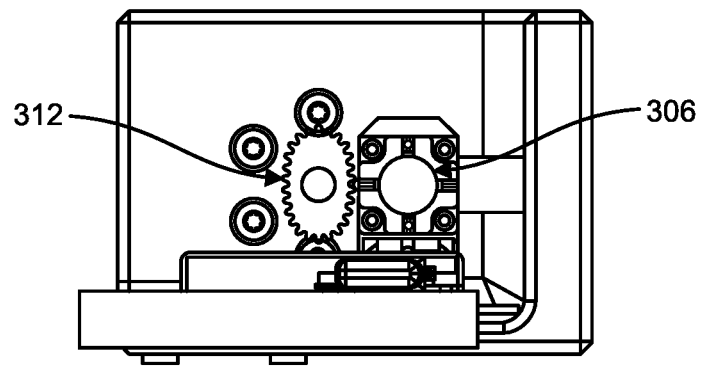
Figure 3D:
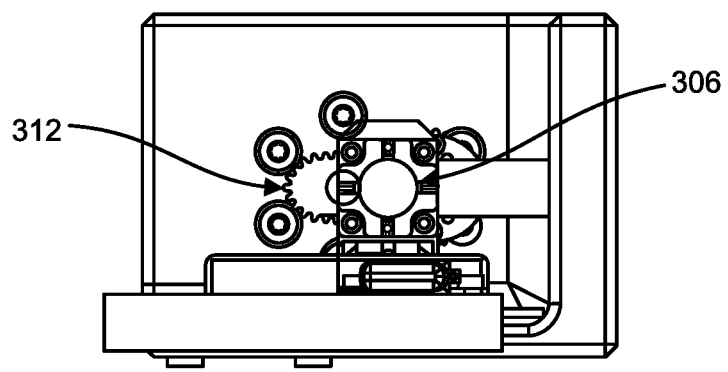

FIGS. 3B-3C show a bottom view of the system 300 of FIG. 3A as the yoke 318, mirror 306, and focus optic 308 traverse a stroke from a right position to a middle position and finally to a left position. FIG. 3B shows the system 300 with the yoke 318, mirror 306 and focus optic 308 in a position fully to the right at a beginning of a stroke. FIG. 3C shows the system 300 with the yoke 318, mirror 306 and focus optic 308 in a position in the middle of the stroke. FIG. 3D shows the system 300 with the yoke 318, mirror 306 and focus optic 308 in a position fully to the left at the end of the stroke. By virtue of the non-circular gears 312 and 314, a gear ratio between the motor 310 and the eccentric pin 316 is non-constant and varies according to rotational position.

In the case of elliptical bilobe gears, the gear ratio varies between about K and about 1/K twice over a single rotation, where K is a ratio of a maximum radius of a pitch ellipse divided by a minimum radius of the pitch ellipse. A mechanism that uses non-circular gears to drive a Scotch yoke is one technique for converting a rotational movement to a reciprocating movement having a constant or near constant linear speed. For example, according to some embodiments it is desirable to scan the EMR beam at a constant linear speed of about 1000 mm/s with a tolerance of about +/−25% and to minimize acceleration and deceleration time.

Figure 4A:
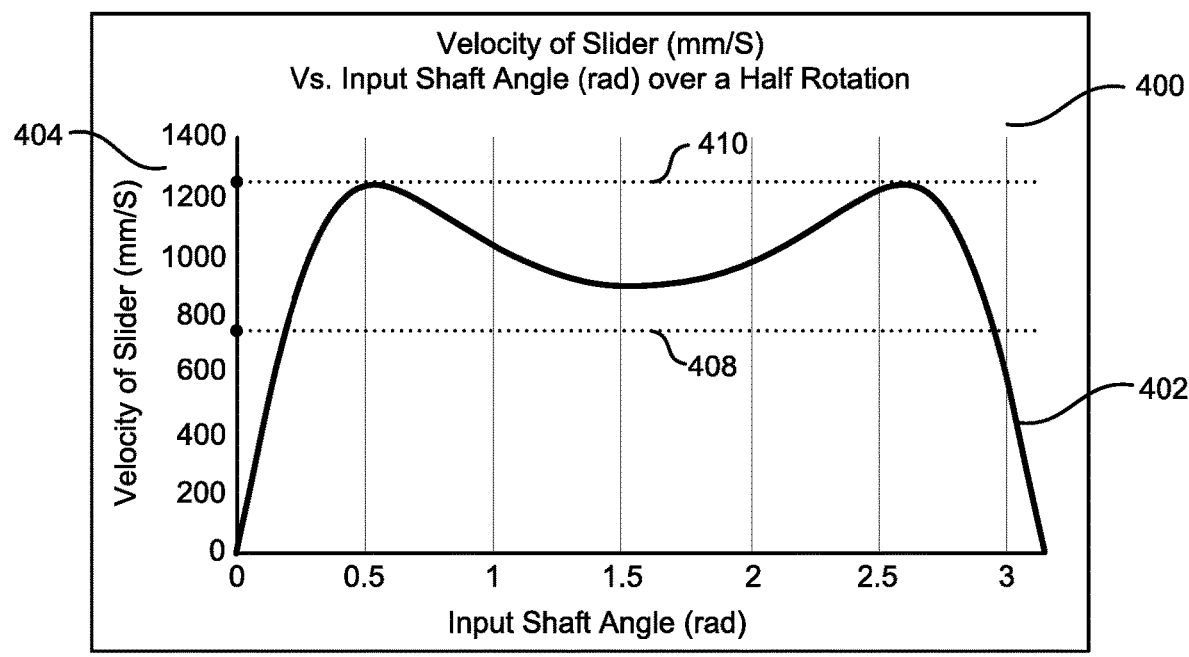
FIG. 4A is a graph showing scan velocity as a function of input shaft rotation angle for a first example reciprocation mechanism, according to some embodiments.
Figure 4B:
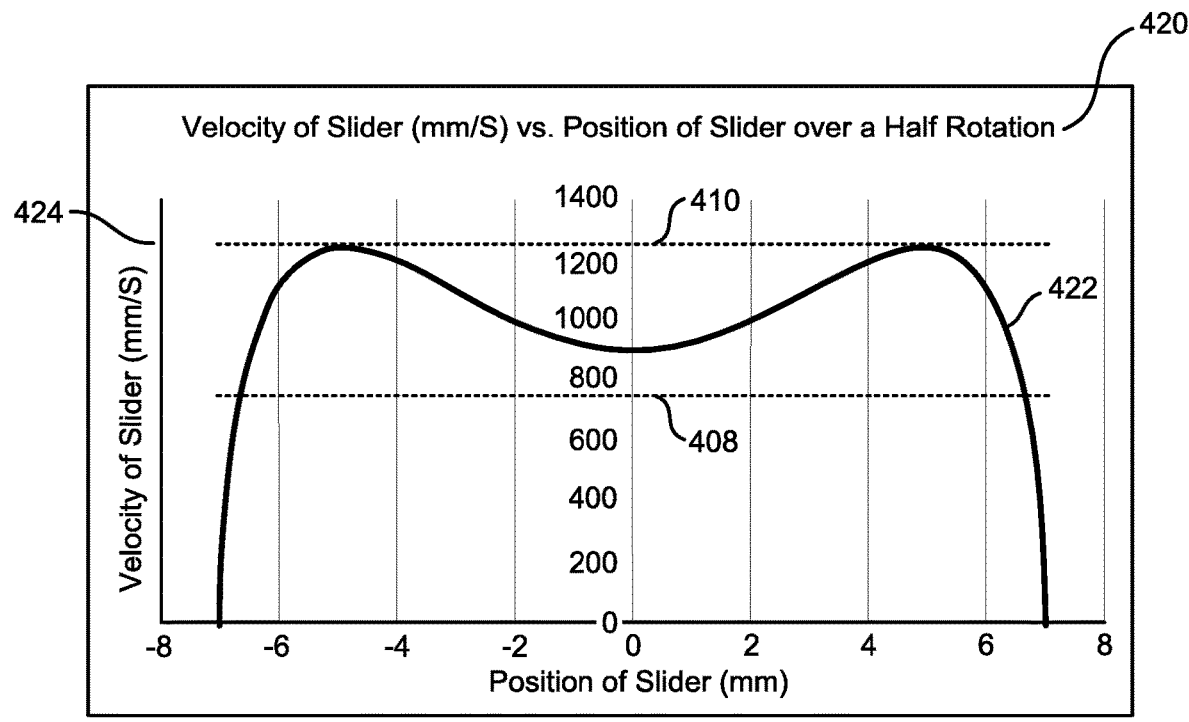
FIG. 4B is a graph showing scan velocity as a function of scan position for a first example reciprocation mechanism, according to some embodiments.
Figure 4C:
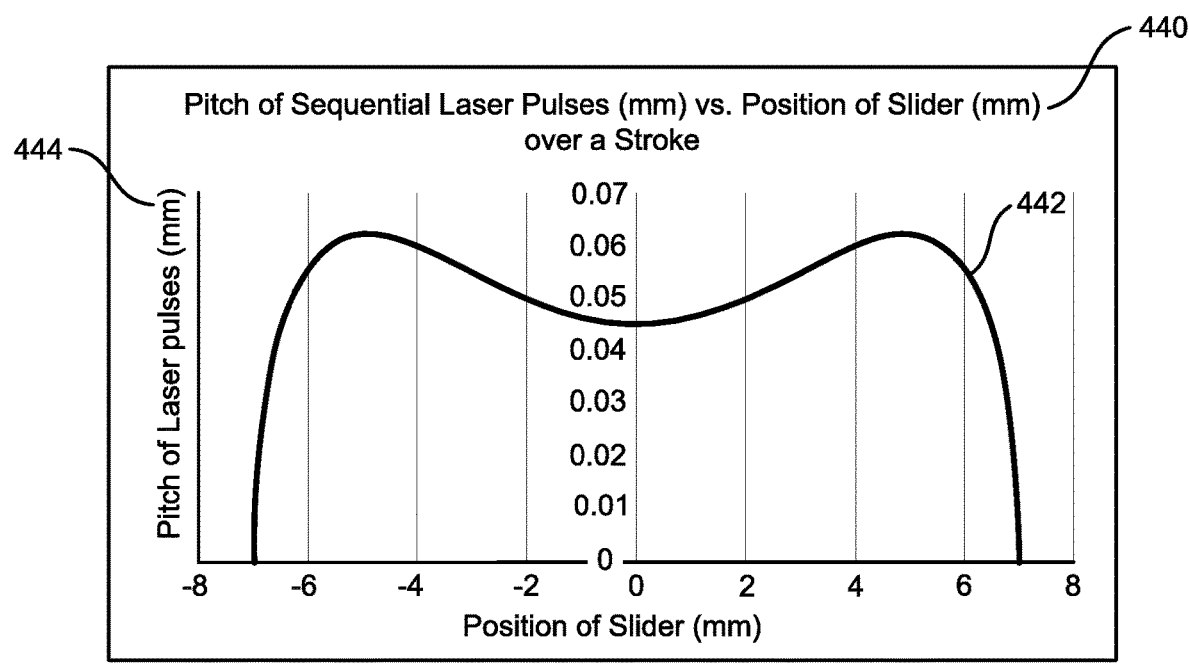
FIG. 4C is a graph showing pulse pitch as a function of scan position for a first example reciprocating mechanism and pulsed electromagnetic radiation (EMR) beam, according to some embodiments.

FIGS. 4A-4C show graphs describing motion profiles of a first exemplary reciprocating mechanism comprising elliptical bilobe gears having a K value of about 1.7; a Scotch yoke mechanism with a stroke length of about 14 mm and an eccentric radius of about 7 mm; and, an input shaft being driven at a constant velocity of about 2089 RPM.

FIG. 4A shows a graph 400 of a velocity profile 402 of a first exemplary reciprocating movement that corresponds to a one-half rotation of the input shaft of the first example reciprocating mechanism. The graph 400 has instantaneous linear speed of a slider (e.g., focus optic) in millimeters per second plotted along a vertical axis 404 and input shaft angle (e.g., motor shaft angle) in radians plotted along a horizontal axis 406. A lower threshold speed 408 is about 25% less than the desired constant linear speed of 1000 mm/s (e.g., 750 mm/s). An upper threshold speed 410 is about 25% more than the desired linear speed of 1000 mm/s (e.g., 1250 mm/s). The velocity profile 402 has an instantaneous speed 404 between the lower threshold speed 408 and the upper threshold speed 410 (e.g., has a constant speed) for about 88% of the input shaft angle 406.

FIG. 4B shows a graph 420 of a velocity profile 422 of the first example reciprocating movement that corresponds to a one-half rotation of the input shaft (e.g., one stroke of the slider) of the first example reciprocating mechanism. The graph 420 has the instantaneous linear speed of a slider (e.g., focus optic) in millimeters per second plotted along a vertical axis 424 and slider position (e.g., objective position) in millimeters plotted along a horizontal axis 426. The lower threshold speed 408 is about 25% less than the desired constant linear speed of 1000 mm/s (e.g., 750 mm/s). The upper threshold speed 430 is about 25% more than the desired linear speed of 1000 mm/s (e.g., 1250 mm/s). The velocity profile 422 has an instantaneous speed 424 between the lower threshold speed 408 and the upper threshold speed 410 (e.g., has a constant linear speed) for about 13.3 mm or about 95% of the stroke. According to some embodiments, a scanned beam is gated to fire only where and when the velocity profile 422 has an instantaneous linear speed between the lower threshold 428 and the upper threshold 430 (e.g., a range of positions between about −7.5 mm and about +7.5 mm).

FIG. 4C shows a graph 440 of a laser pulse pitch profile 442 of the first exemplary reciprocating movement that corresponds to a one-half rotation of the input shaft (e.g., one stroke of a slider) of the first example reciprocating mechanism scanning an EMR beam that is pulsed at a repetition rate of about 20 KHz. The graph 440 has instantaneous pitch between sequential laser pulses in millimeters plotted along a vertical axis 444 and the slider position (e.g., the objective position) in millimeters plotted along a horizontal axis 446.

Figure 5A:
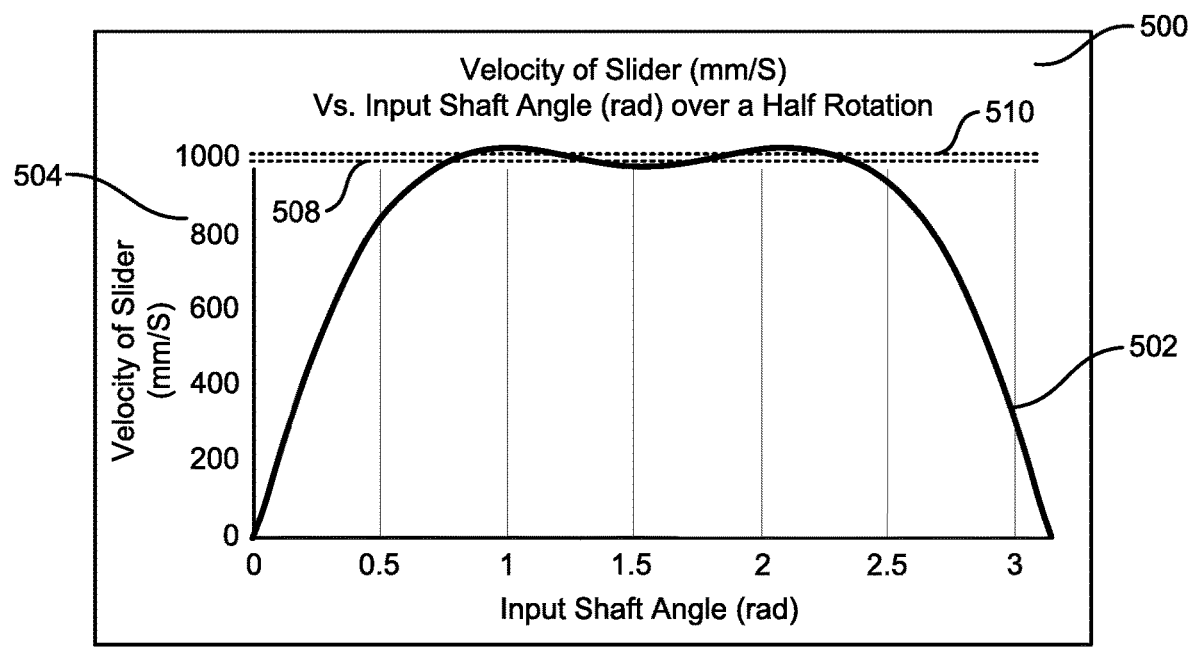
FIG. 5A is a graph showing scan velocity as a function of input shaft rotation angle for a second example reciprocation mechanism, according to some embodiments.
Figure 5B:
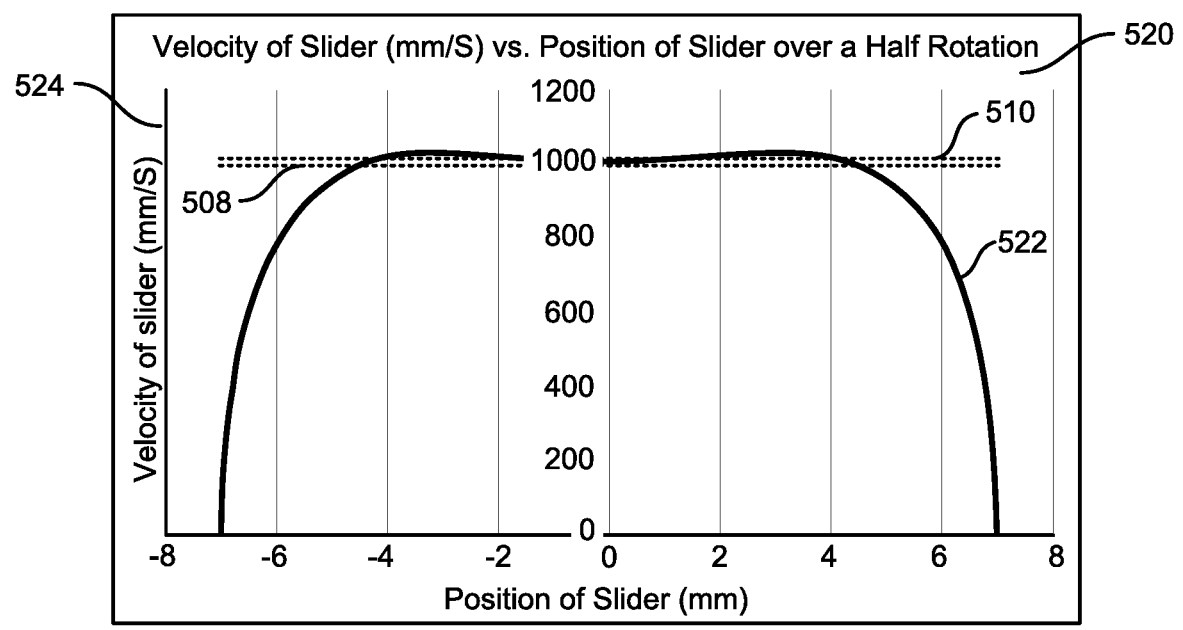
FIG. 5B is a graph showing scan velocity as a function of scan position for a second example reciprocation mechanism, according to some embodiments.
Figure 5C:
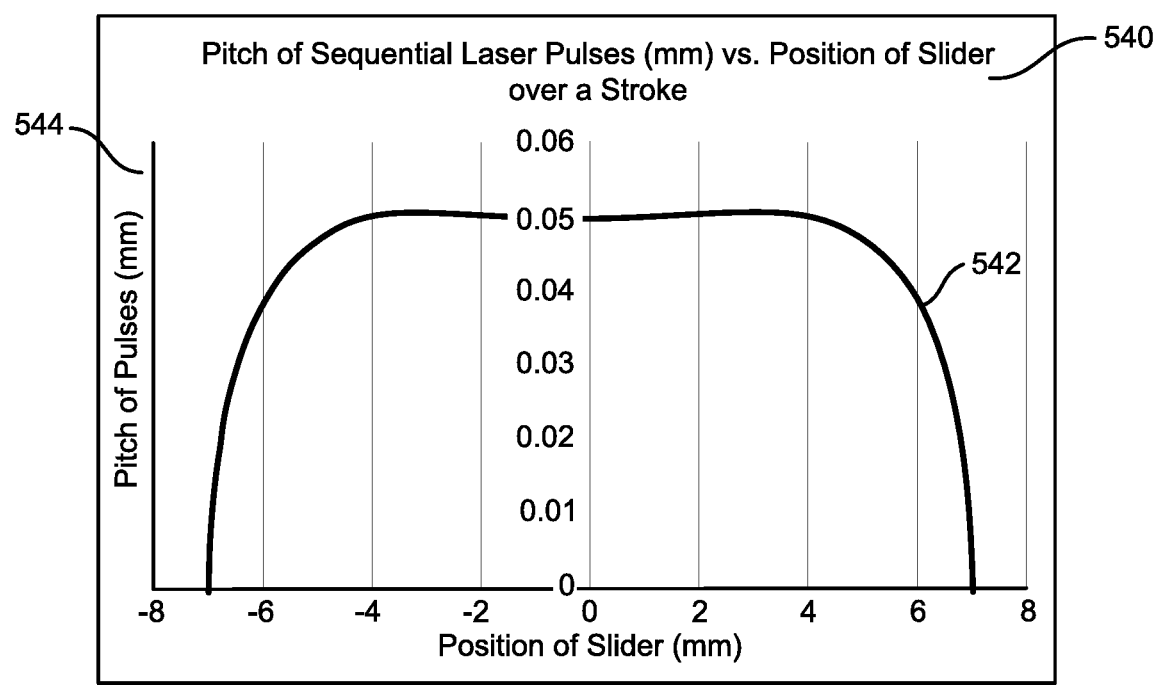
FIG. 5C is a graph showing pulse pitch as a function of scan position for a second example reciprocating mechanism and pulsed electromagnetic radiation (EMR) beam, according to some embodiments.

According to some embodiments it is desirable to scan the EMR beam at linear speed that is more constant. For example, according to some embodiments a constant linear speed of 1000 mm/s with a tolerance of about +/−1% is desired. FIGS. 5A-C show graphs describing motion profiles of a second exemplary reciprocating mechanism comprising elliptical bilobe gears having a K value of about 1.3; a Scotch yoke mechanism with a stroke length of about 14 mm and an eccentric radius of about 7 mm; and, an input shaft being driven at a constant velocity of about 1759 RPM.

FIG. 5A shows a graph 500 of a velocity profile 502 of a second exemplary reciprocating movement that corresponds to a one-half rotation of the input shaft of the second example reciprocating mechanism. The graph 500 has instantaneous linear speed of a slider (e.g., focus optic) in millimeters per second plotted along a vertical axis 504 and input shaft angle (e.g., motor shaft angle) in radians plotted along a horizontal axis 506. A lower threshold speed 508 is about 1% less than a desired constant linear speed of 1000 mm/s (e.g., 990 mm/s). An upper threshold speed 510 is about 1% more than the desired linear speed of 1000 mm/s (e.g., 1010 mm/s). The velocity profile 502 has an instantaneous speed 504 between the lower threshold speed 508 and the upper threshold speed 510 (e.g., has a constant speed) for about 49% of the input shaft angles 506.

FIG. 5B shows a graph 520 of a velocity profile 522 of the second exemplary reciprocating movement that corresponds to a one-half rotation of the input shaft (e.g., one stroke of a slider) of the second example reciprocating mechanism. The graph 520 has the instantaneous linear speed of the slider (e.g., focus optic) in millimeters per second plotted along a vertical axis 524 and the slider position (e.g., objective position) in millimeters plotted along a horizontal axis 526. The lower threshold speed 508 is about 1% less than the desired constant linear speed of 1000 mm/s (e.g., 990 mm/s). The upper threshold speed 530 is about 1% more than the desired linear speed of 1000 mm/s (i.e., 1010 mm/s). The velocity profile 522 has an instantaneous speed 524 between the lower threshold speed 508 and the upper threshold speed 510 (e.g., a constant speed) for about 8.4 mm or about 60% of the stroke. According to some embodiments, a scanned beam is gated to fire only where and when the velocity profile 522 has an instantaneous linear speed that is between the lower threshold 528 and the upper threshold 530 (e.g., a range of positions between about −4 mm and about +4 mm).

FIG. 5C shows a graph 540 of a laser pulse pitch profile 542 of the second exemplary reciprocating movement that corresponds to a one-half rotation of the input shaft (e.g., one stroke of the slider) of the second example reciprocating mechanism scanning an EMR beam that is pulsed at a repetition rate of about 20 KHz. The graph 540 has instantaneous pitch between sequential laser pulses in millimeters plotted along a vertical axis 544 and slider position (e.g., objective position) in millimeters plotted along a horizontal axis 546.

Figure 6A:
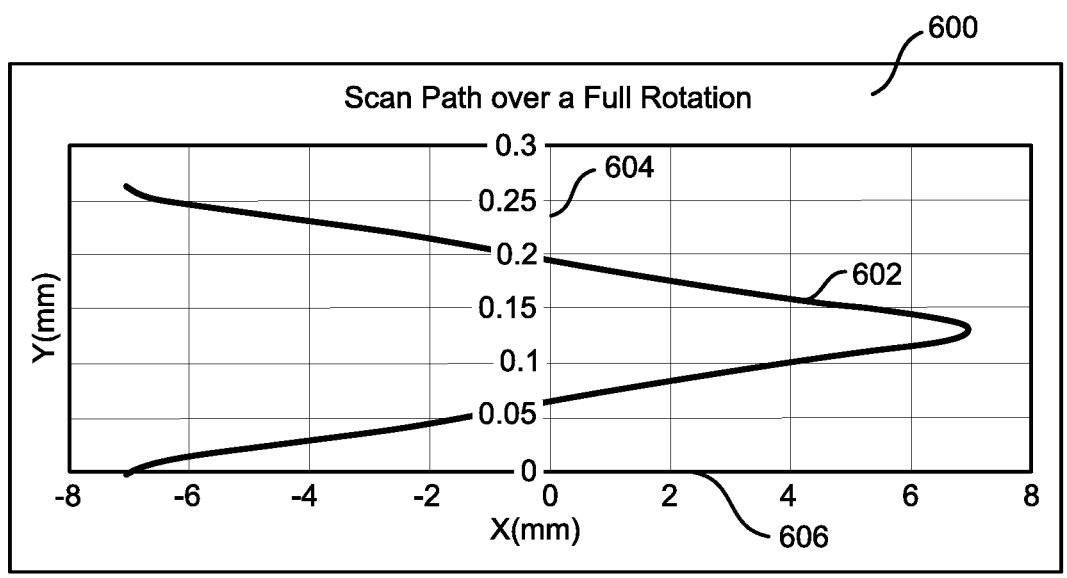
FIG. 6A is a graph showing a modeled scan path for an exemplary beam scanner, according to some embodiments.
Figure 6B:
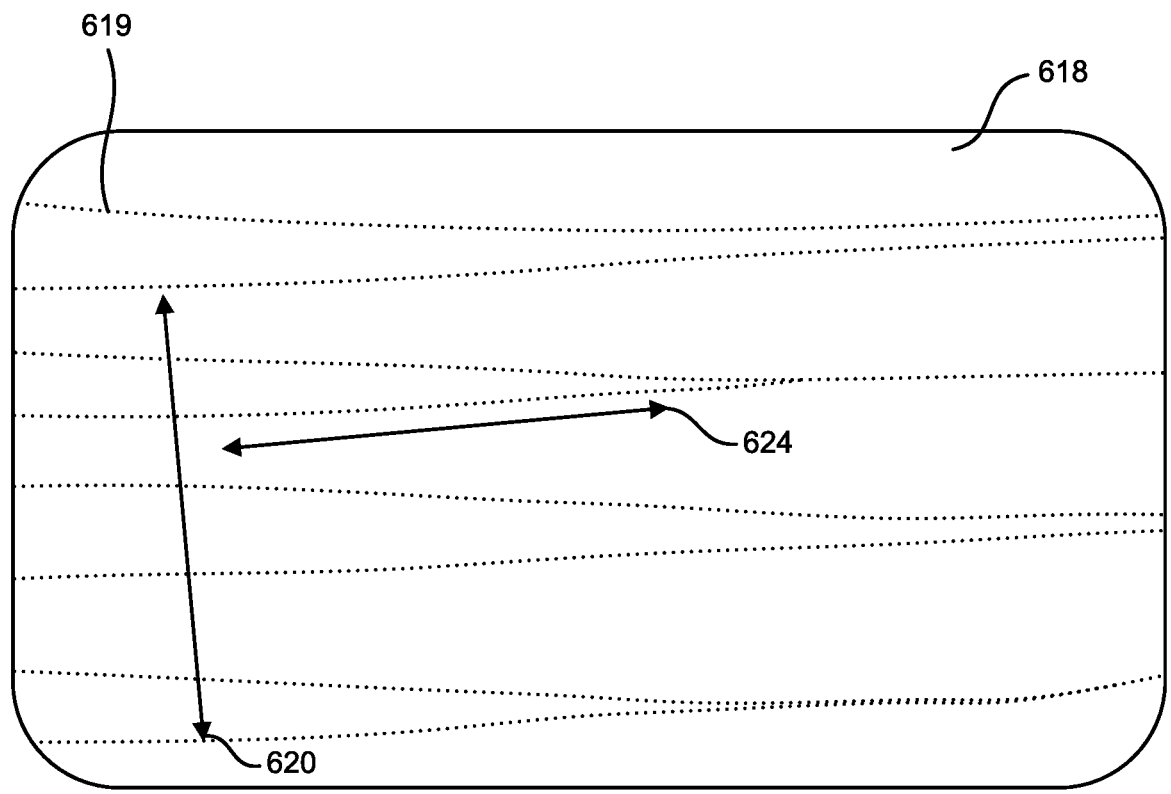
FIG. 6B is a microscope image showing an acrylic block after irradiation by an exemplary beam scanner and electromagnetic radiation (EMR) beam, according to some embodiments.

According to some embodiments, scanning is achieved in two axes through reciprocating scanning as described above in a first axis and a constant linear movement in a second axis, which is generally orthogonal to the first axis. FIGS. 6A-B illustrate a scan path according to this method. FIG. 6A shows a graph 600 of a two-dimensional (2D) scan path 602. The graph has position along a slow axis in millimeters plotted along a vertical axis 604 and position along a fast axis in millimeters plotted along a horizontal axis 606. The scan path 602 comprises movement in the fast axis 606, which is provided for by an exemplary reciprocating mechanism comprising elliptical bilobe gears having a K value of 1.7; a Scotch yoke mechanism with a stroke length of about 14 mm and an eccentric radius of about 7 mm; and an input shaft being driven at a constant velocity of about 2300 RPM.

The scan path further comprises movement in the slow axis 604, which is provided for by a stage moving at a constant velocity of about 10 mm/s. The scan path 602 has a zig-zag pattern. An exemplary scanning system was built and tested with the above parameters and a laser operating at a repetition rate of about 20 KHz.

FIG. 6B shows a microscope image 618 (magnification 10×) of an acrylic block that was scanned in two dimensions according to the scan path and parameters described above with a further exemplary scanner system. A series of laser marks 619 traces the scan path with an individual mark corresponding to an individual laser pulse. A vertical leader 620 shows a slow axis distance between three full rotations (e.g., 6 strokes) of the exemplary reciprocating mechanism. The slow axis distance is estimated to be about 0.78 mm. A horizontal leader 624 has an equal distance as the vertical leader and is placed normal to the vertical leader. Between about 13 and about 20 pulses occur over the distance of the horizontal leader 624. Therefore, an average pitch between sequential laser pulses along the fast axis can be estimated to be in a range between about 0.04 mm and about 0.06 mm. This corresponds to an estimated fast axis scan rate of between about 800 mm/s and about 1200 mm/s.

Figure 6C:
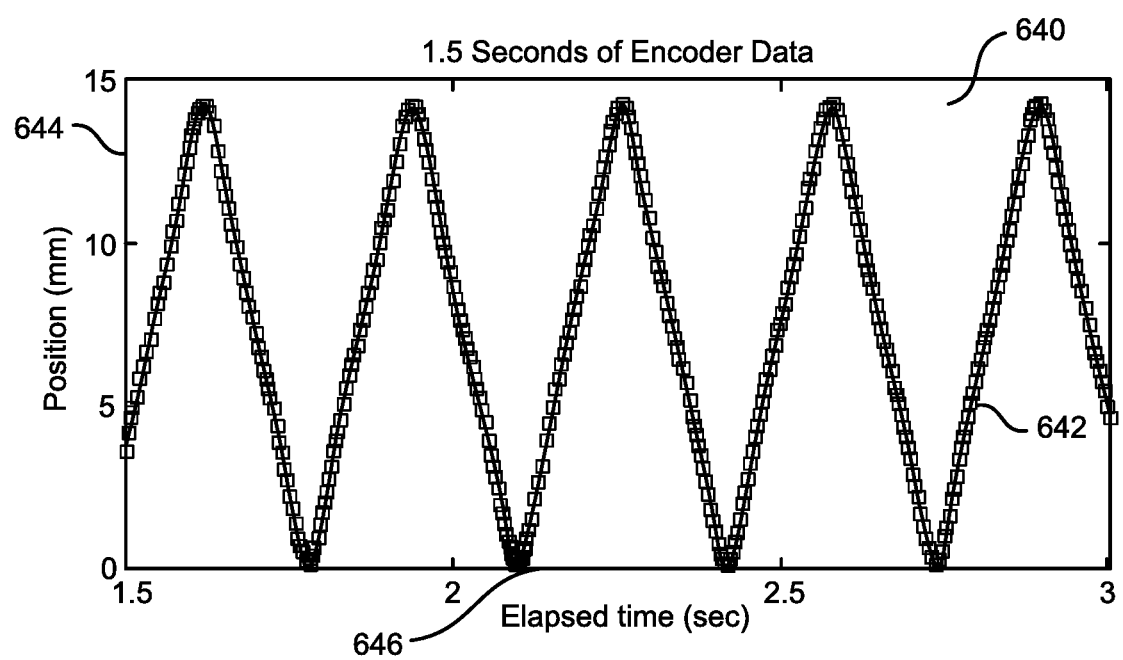
FIG. 6C illustrates a reciprocating movement with a graph showing measured position vs. time for an exemplary reciprocating mechanism, according to some embodiments.

Referring now to FIG. 6C, performance of the exemplary reciprocating mechanism is further described with reference to a graph 640. A reciprocating movement 642 was measured by way of a magnetic strip and linear encoder, see above. The exemplary reciprocating mechanism was driven by a constant rotational movement at a slow speed (e.g., about 2 Hz). The graph 640 displays position of the reciprocating movement in millimeters along a vertical axis 644. And, time in seconds is displayed along a horizontal axis 646. The reciprocating movement 642 can be seen in the graph 640 to be linear (e.g., the reciprocating movement has a constant scan speed).

Figure 7A:
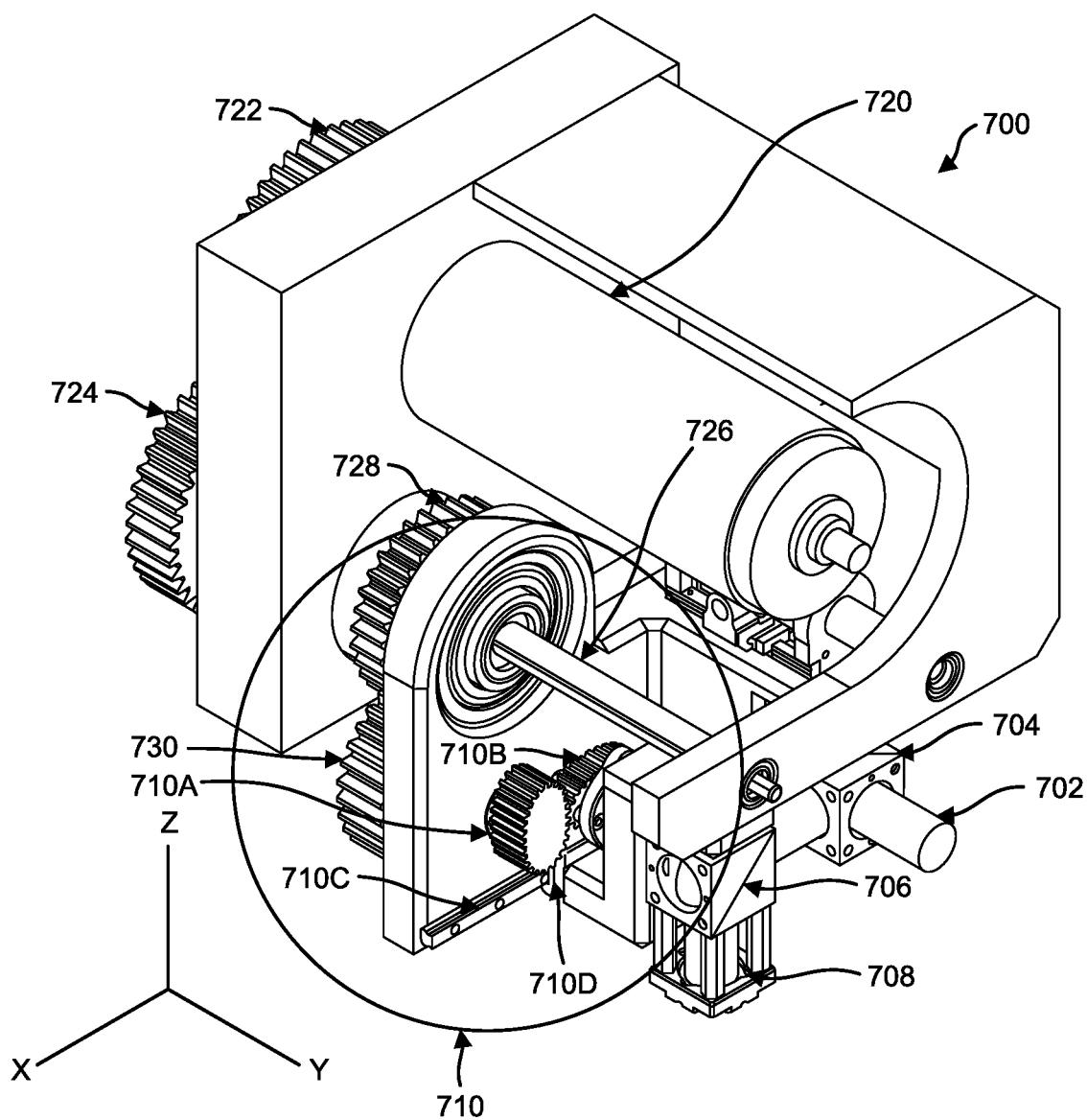
FIG. 7A shows an isometric view of an exemplary 2-dimensional (2D) beam scanner, according to some embodiments.

According to some embodiments, it is advantageous to scan an EMR beam in two dimensions in a non-zig-zag pattern. For example, according to some embodiments a raster scan or pseudo-raster scan pattern is desirable. An example of the two-dimensional (2D) scanner 700 is shown in FIGS. 7A-7F. Referring to FIG. 7A, an electromagnetic radiation (EMR) beam 702 is directed into the scanner 700 from the right along the y axis and is redirected via an optical system. The EMR beam 702 is reflected about 90° to the left by a first reflector 704 along the x axis and then 90° down along the z axis by a second reflector 706. Finally, the beam is directed incident an objective 708 that focuses the beam. The scanner 700 comprises a reciprocation mechanism 710 such as that described above. The reciprocation mechanism 710 comprises a first bilobe elliptical gear 710A, a second bilobe elliptical gear 710B, a linear rail 710C, and a carriage 710D. The reciprocating mechanism 710 is configured to convert a rotational movement to a reciprocating movement along the x axis. A rotational movement is provided by a motor 720, which is operatively coupled with the reciprocating mechanism 710 via a drivetrain. The drivetrain comprises a first gear 722, a second gear 724, a ball spline driveshaft 726, a third gear 728, and a fourth gear 730. The first gear 722 and the second gear 724, as well as the third gear 728 and the fourth gear 730 have gear ratios of approximately 1:1. Therefore, a rotational speed of the rotational movement at the motor 720 is substantially unchanged by gearing of the drivetrain.

Figure 7B:
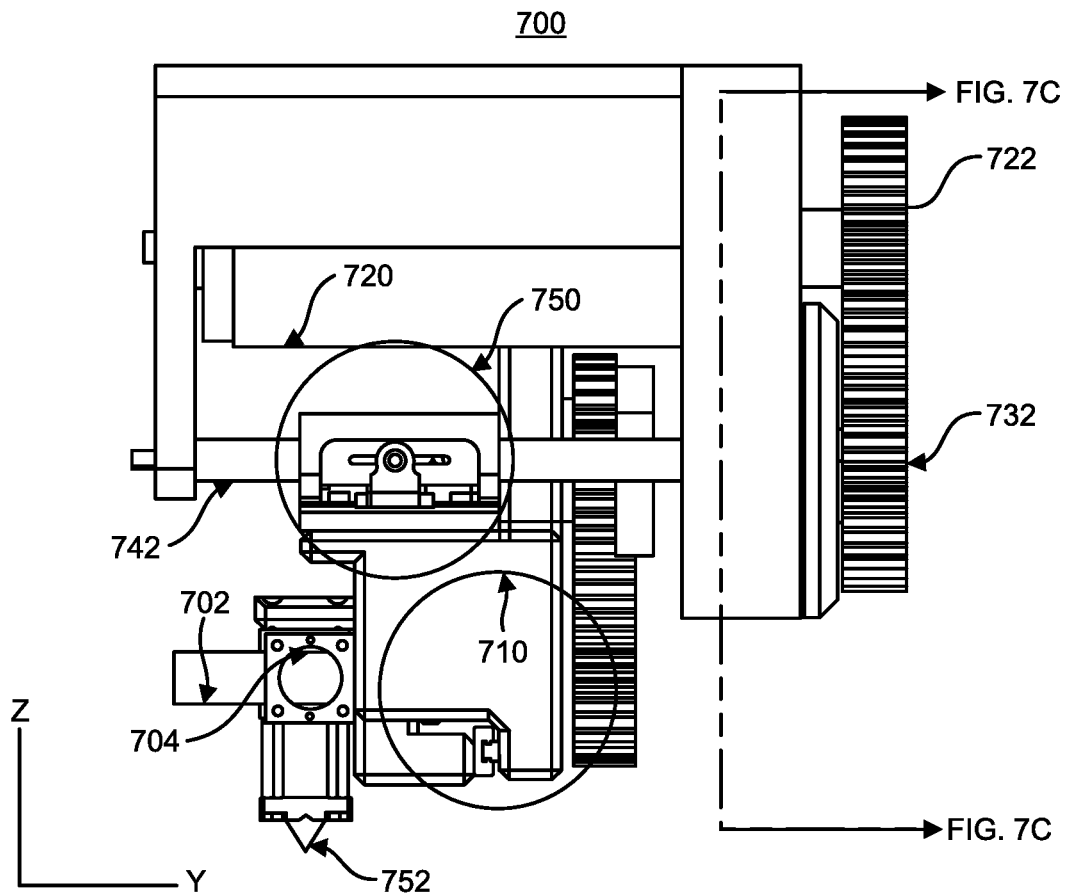
FIG. 7B shows a front view of an exemplary 2D beam scanner, according to some embodiments.
Figure 7C:
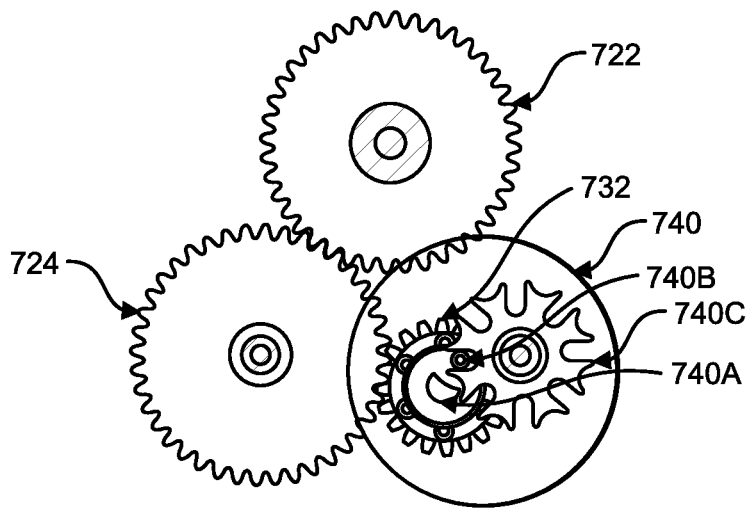
FIG. 7C shows a view of an exemplary intermittent mechanism, according to some embodiments.

Referring now to FIGS. 7B-7C, an intermittent mechanism 740 is shown in mechanical communication with both the reciprocating mechanism 710 and the motor 720. FIG. 7B shows a front view of the exemplary 2D beam scanner 700. FIG. 7C shows a view of an exemplary intermittent mechanism. A fifth gear 732 meshes with the second gear 724. The gear ratio between the second gear 724 and the fifth gear 732 is about 1:2. Therefore, a rotational speed of the fifth gear 732 is twice that of the second gear 724, and ultimately the motor 720. The intermittent mechanism comprises a crank 740A having an eccentric pin 740B. The crank 740A is coupled with the fifth gear 732 and therefore rotates at the same speed as the fifth gear 732. The intermittent movement is provided for by a Geneva wheel 740C, which is moved intermittently once per every rotation of the crank 740A. The Geneva wheel 740C is shown with 8 slots, into which the eccentric pin 740B periodically rides, rotating the Geneva wheel 740C. Because the Geneva wheel has 8 slots, it moves approximately ⅛th of a rotation for every rotation of the crank 740A. For the remaining ⅞th of crank rotation, the Geneva wheel dwells (i.e., does not rotate); as, it is held in place by a half-moon profile of the crank 740A. Finally, the intermittent rotational movement of the Geneva wheel 740C is transferred to intermittent linear movement through the combination of a lead screw 742 and a lead screw nut assembly 750. The lead screw nut assembly 750 introduces the intermittent linear movement to the reciprocating mechanism 710 and objective 708 causing an EMR beam focus 752 to move generally along the y-axis.

Figure 7D:
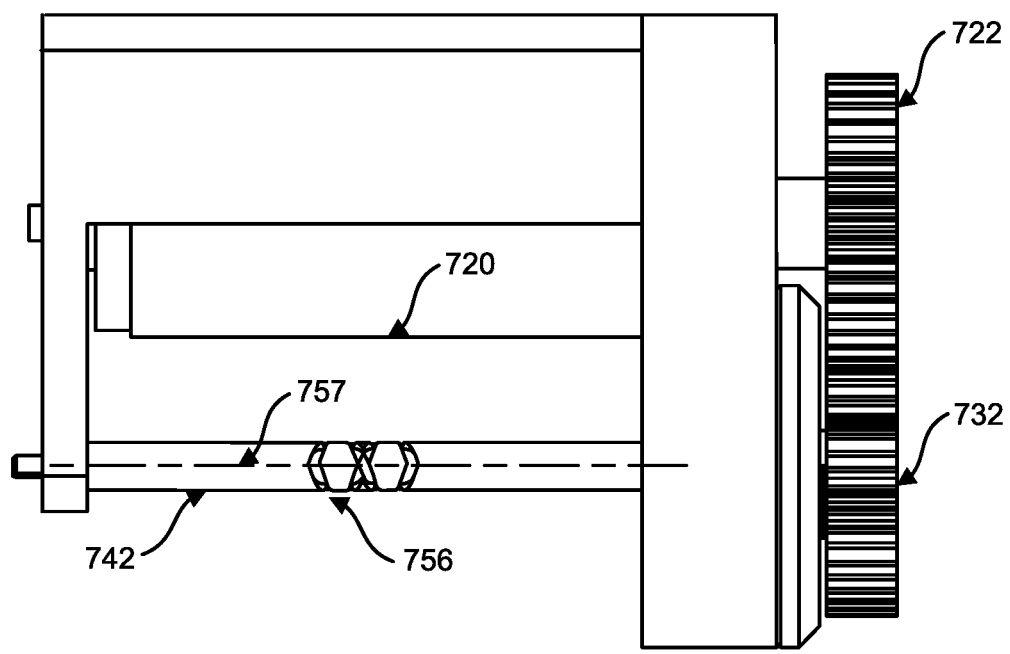
FIG. 7D shows a side view of an exemplary self-reversing lead screw, according to some embodiments.

FIG. 7D illustrates the drivetrain of the scanner 700 without the reciprocating mechanism 710 or the optical system. In FIG. 7D, a lead screw thread 756 is shown. The lead screw thread 756 is a self-reversing thread, commonly known as a diamond thread. These threads allow a nut to reverse directions along a lead screw axis 757, without changing a direction of rotation of the lead screw 742.

Figure 7E:
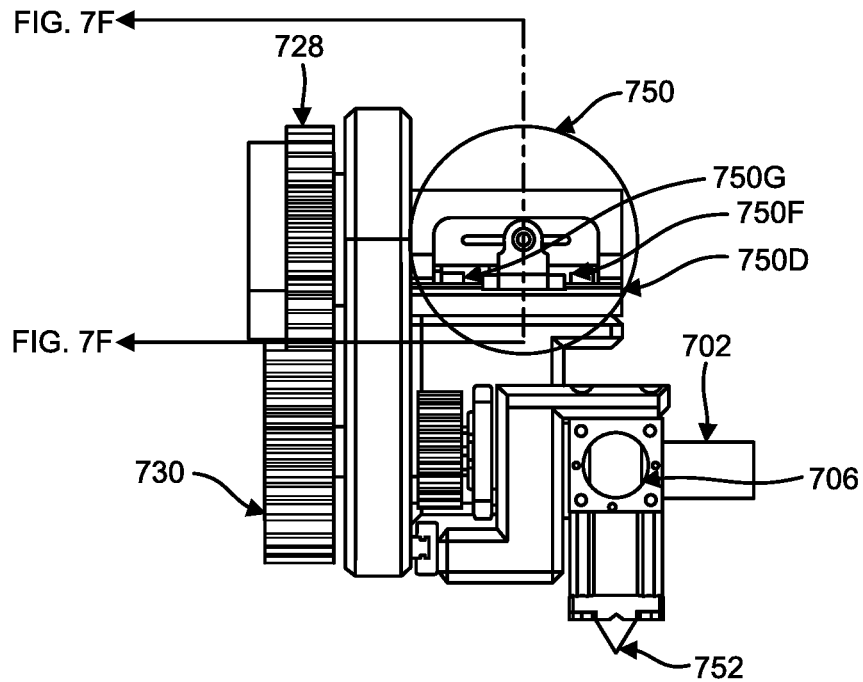
FIG. 7E shows a front view of a portion of an exemplary 2D beam scanner, according to some embodiments.
Figure 7F:
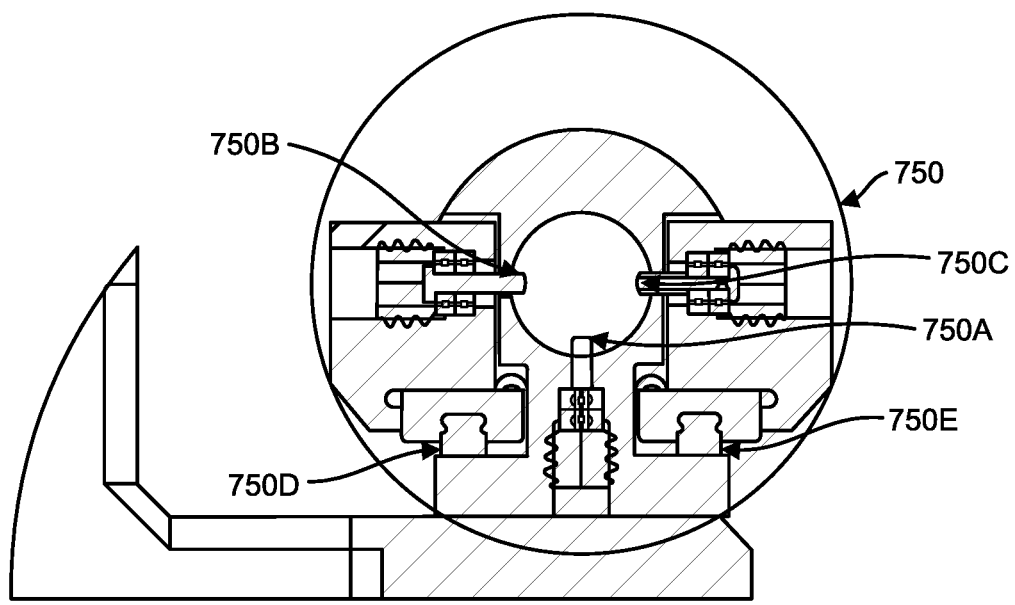
FIG. 7F shows a cross-section view of a self-reversing lead screw nut assembly, according to some embodiments.

Referring now to FIGS. 7E-7F, the lead screw nut assembly 750 is shown affixed to the reciprocating mechanism 710 and a portion of the optical system. FIG. 7E shows a front view of a portion of the exemplary 2D beam scanner 700. FIG. 7F shows a cross-section view of a self-reversing lead screw nut assembly 750. The lead screw nut assembly 750 is like the Reversing Nut for a Diamond Thread Screw, which is described in U.S. Pat. No. 3,779,094, and is incorporated herein by reference. The nut assembly 750 comprises a static roller 750A, a first sliding roller 750B, and a second sliding roller 750C. The first sliding roller 750B slides along a first rail 750D that runs parallel to the lead screw axis. The second sliding roller 750C slides along a second rail 750E that also runs parallel to the lead screw axis 757. Sliding movement of each of the sliding rollers 750B, 750C is limited by a fore and an aft stop. Referring to FIG. 7E, a first fore stop 750F arrests the sliding of the first sliding roller 750B as the nut assembly is moving forward on the thread 756. Likewise, a first aft stop 750G arrests the sliding of the first sliding roller 750B as the nut assembly 750 is moving backward on the thread 756.

Figure 8:
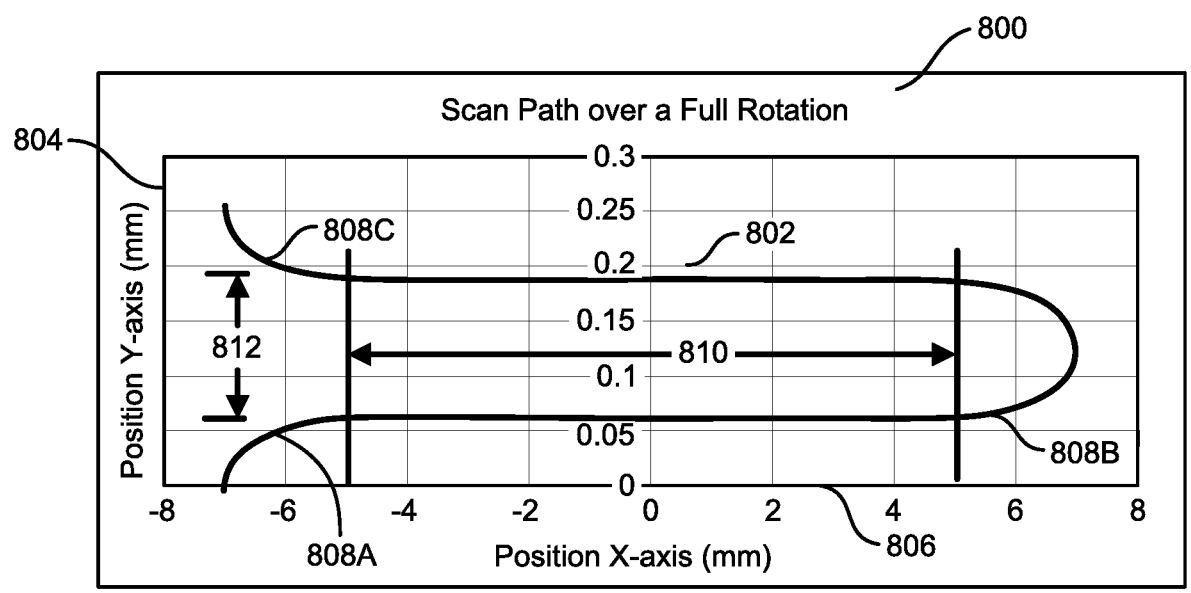
FIG. 8 is a graph showing a modeled scan path for an exemplary 2D beam scanner, according to some embodiments.

Performance of an exemplary 2D scanner 700 is modeled and displayed in FIG. 8. The exemplary 2D scanner comprises: a motor, a reciprocating mechanism, a Scotch yoke mechanism, and an intermittent mechanism. The motor is driven at a constant velocity of about 2089 RPM. The reciprocating mechanism comprises elliptical bilobe gears having a K value of about 1.7. The Scotch yoke mechanism possesses a stroke length of about 14 mm and an eccentric radius of about 7 mm, and a gear ratio between the motor and reciprocating mechanism of about 1:1. The intermittent mechanism comprises a Geneva Wheel having a crank radius of about 5 mm, about 8 slots, and separation between driving and driven elements of about 13.07 mm, a lead screw pitch of 1 mm/rev, and a gear ratio between the motor and the intermittent mechanism of 1:2. Parameters of the exemplary 2D scanner are summarized in table 1 below.

TABLE 1

Exemplary 2D Scanner Parameter Values

| Exemplary 2D Scanner Parameter | Value |
|---|---|
| Motor Velocity (RPM) | 2089 |
| K Value, Bilobe gears (—) | 1.7 |
| Scotch Yoke Crank Radius (mm) | 7 |
| Scotch Yoke Stroke Length (mm) | 7 |
| Motor to Reciprocating Mechanism Gear Ratio (Motor:Rec. Mech.) | 1:1 |
| Geneva Wheel Crank Radius (mm) | 5 |
| Geneva Wheel Shaft Spacing (mm) | 13.07 |
| Geneva Wheel Slots (—) | 8 |
| Motor to Intermittent Mechanism Gear Ratio (Motor:Int. Mech.) | 1:2 |
| Lead Screw Pitch (mm/rev) | 1 |

As shown in FIG. 8, graph 800 plots a scan path 802 in two dimensions. Scan location along an intermittent movement axis is displayed in millimeters along a vertical axis 804. Scan location along a reciprocating axis is displayed in millimeters along a horizontal axis 806. The scan path 802 is a raster or pseudo-raster pattern. The intermittent mechanism and reciprocating mechanism are timed such that an intermittent movement 808A-808C is introduced substantially at a stroke's end/beginning. A full rotation of the reciprocating mechanism results in two strokes. And, a single rotation of the intermittent mechanism results in only one intermittent movement. Therefore, mechanical communication between the reciprocating mechanism and the intermittent mechanism results in two rotations to the intermittent mechanism corresponding to a single rotation of the reciprocating mechanism (e.g., gear ratio of about 1:2). In some instances, it may be undesirable to have an electromagnetic radiation (EMR) beam firing during the intermittent movements 808A-C. In these instances, the EMR beam may be gated to fire during a window 810 wherein the scan path 802 movement is desirable. A vertical pitch 812 is approximately 0.13 mm. Referring above to FIG. 4B, an exemplary reciprocating mechanism having identical parameters is shown to have an average scan speed of approximately 1000 mm/s over axial positions ranging from about −5 mm to about +5 mm (e.g., within the window 810). Therefore, to have a horizontal pitch about equal to the vertical pitch the EMR beam will need to be pulsed at a repletion rate of about 7.7 KHz. According to some embodiments, it is advantageous for a 2D scan path to reverse direction after reaching an end of a pass.

As described above, a self-reversing lead screw 756 and nut 750 allow a rotational motion of a single direction to produce linear motion in two directions. According to some embodiments, a self-reversing lead screw 756 reverses a 2D scan path direction once the scan path has reached an extremum along a lead screw scan axis (e.g., finished a pass). According to some embodiments, a change in direction along the lead screw axis is sensed and provided as input to a controller. According to some embodiments, the lead screw nut 750 comprises one or more sliding thread engaging elements 750B and 750C. These sliding thread engaging elements 750B and 750C allow for the thread to remain in an engaged condition when the static thread engaging element 750A is at an intersection of forward and backward turning threads (and therefore unengaged). Where the nut assembly 750 is reversing direction (e.g., at an extremum), one or more of the sliding thread engaging elements 750B and 750C slide along an axis that is parallel to the lead screw axis. According to some embodiments, a detector (e.g., a microswitch, a linear encoder, etc.) is used to detect sliding of one or more of the sliding thread engaging elements 750B and 750C, and therefore also the scan path reversing direction along the lead screw axis. According to some embodiments, it is advantageous to scan over a two-dimensional area with a beam focus at different depths (e.g., scan in three dimensions).

Figure 9:
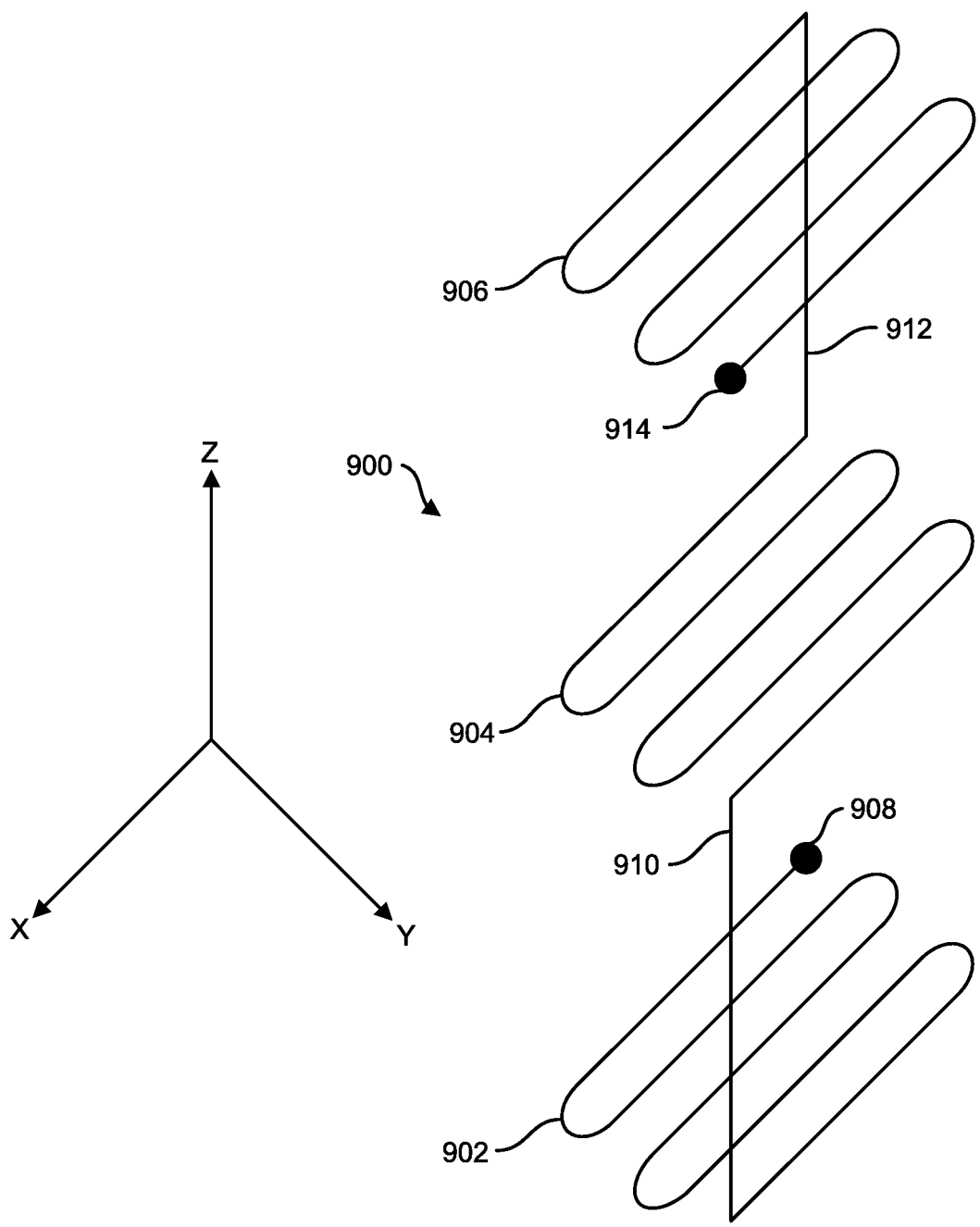
FIG. 9 schematically represents a 3-dimensional (3D) scan path, according to some embodiments.

Referring to FIG. 9, a three-dimensional (3D) scan path 900 is shown having three scan passes at three depths (along a z-axis): a first scan pass 902 at a lowermost depth, a second scan path 904 at a middle depth, and third scan pass 906 at an uppermost depth. The scan path 900 begins at a start point 908 at the lowermost depth and scans the first pass 902. At the end of the first pass 902, the scan path 900 moves up (along the z-axis) 910 and reverses directions (along a y-axis), thereby starting the second pass 904. At the end of the second pass 904, the scan path 900 again moves up (along the z-axis) 912 and again reverses directions (along the y-axis), thereby starting the third pass 906. Finally, the scan path 900 reaches an end point 914 upon completion of the third pass 906. According to some embodiments, movement along the z-axis is movement of a focus along an optical axis. The focus is formed by a focus optic shaping a wavefront of an electromagnetic radiation (EMR) beam. Movement of the focus along the optical axis is achieved in some versions by moving the focus optic along (e.g., up and down) the optical axis. Alternatively, according to some versions, movement of the focus along the optical axis is achieved by varying a divergence of the EMR beam. For example, a distance between the focus optic and the focus is increased by increasing the divergence of the beam being focused.

Treatment of Disorders of Pigmentation

Figure 10:
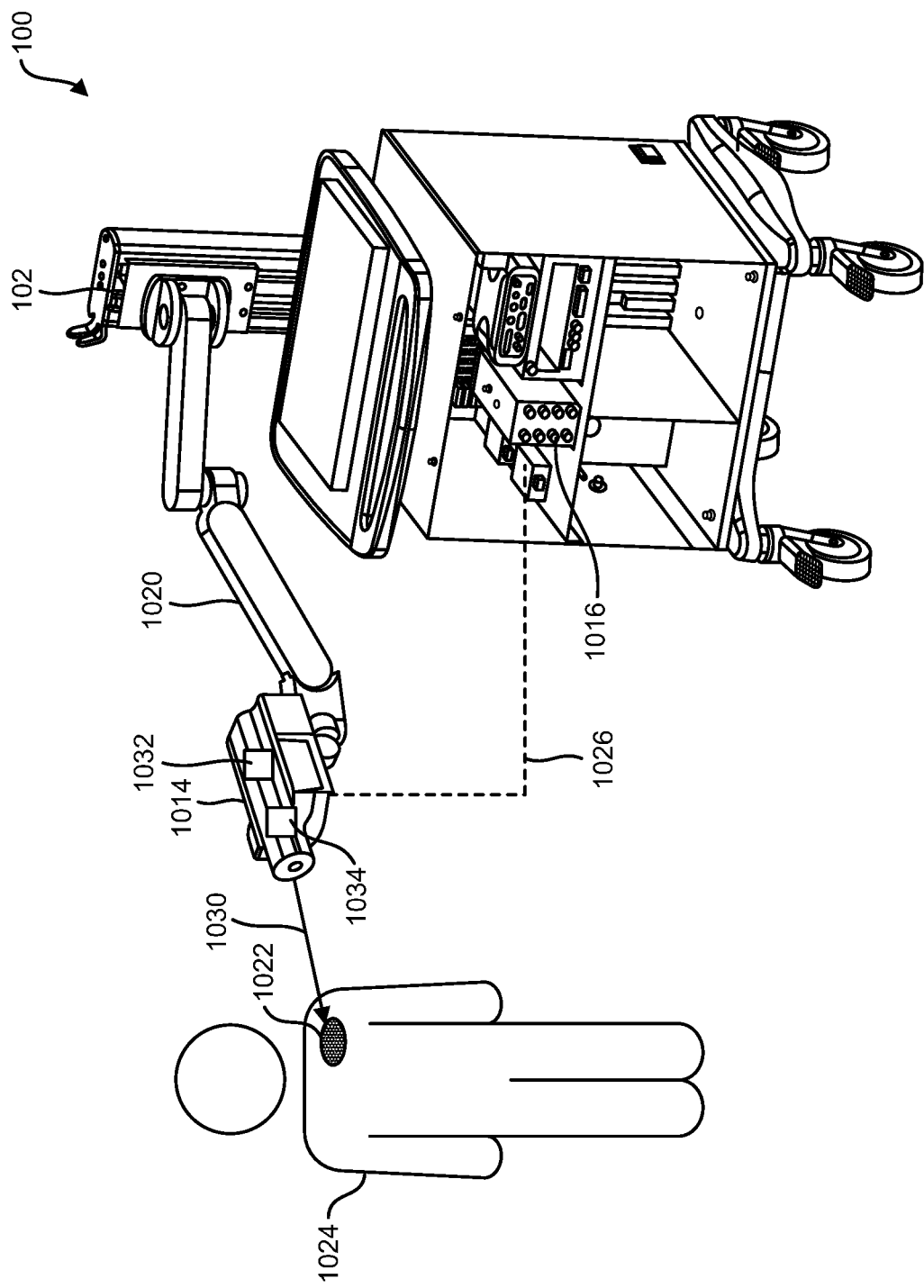
FIG. 10 illustrates an exemplary embodiment of a treatment system.

FIG. 10 illustrates one exemplary embodiment of a treatment system 1010. As shown, the treatment system 1010 includes a platform 1012, and emitter 1014, and a controller 1016. The platform 1012 can include one or more manipulator or arm 1020. The arm 1020 can be coupled to the emitter 1014 for performing various treatments on a target tissue 1022 of a subject 1024. Operation of the platform 1012 and emitter 1014 can be directed by a user, manually or using the controller 1016 (e.g., via a user interface). In certain embodiments (not shown), the emitter can have a hand-held form factor and the platform 1012 can be omitted. In other embodiments, the platform can be a robotic platform and the arms can be communicatively coupled to the controller for manipulation of the emitter.

The emitter 1014 and controller 1016 (and optionally the platform 1012) can be in communication with one another via a communications link 1026, which can be any suitable type of wired and/or wireless communications link carrying any suitable type of signal (e.g., electrical, optical, infrared, etc.) according to any suitable communications protocol.

Embodiments of the controller 1016 can be configured to control operation of the emitter 1014. In one aspect, the controller 1016 can control movement of EMR 1030. As discussed in detail below, the emitter 1014 can include a source 1032 for emission of the EMR 1030 and a scanning system 1034 for manipulation of the EMR 1030. As an example, the scanning system 1034 can be configured to focus EMR 1030 to a focal region and translate and/or rotate this focal region in space. The controller 1016 can send signals to the source 1032, via the communications link 1026 to command the source 1032 to emit the EMR 1030 having one or more selected properties, such as wavelength, power, repetition rate, pulse duration, pulse energy, focusing properties (e.g., focal volume, Raleigh length, etc.). In another aspect, the controller 1016 can send signals to the scanning system 1034, via the communications link 1026 to command the scanning system 1034 to move the focal region of the EMR 1030 with respect the target tissue 1022 in one or more translation and/or rotation operations.

As will be apparent from the description that follows, one advantageous aspect of the system described herein is that control of the treatment, by the controller 1016 and/or the scanning system 1034, enables a treatment pattern substantially in the form of a circle or overlapping circles. Thus, a feature of the system is to utilize a scanning pattern in the form of concentric circles rather than simply depositing a pattern of linear dots.

Embodiments of the treatment system 1010 and methods are discussed herein in the context of targets within skin tissue, such as a dermal layer. However, the disclosed embodiments can be employed for treatment of any tissue in any location of a subject, without limit. Examples of non-skin tissues can include, but are not limited to, surface and sub-surface regions of mucosal tissues, genital tissues, internal organ tissues, and gastrointestinal tract tissues.

Figure 11:
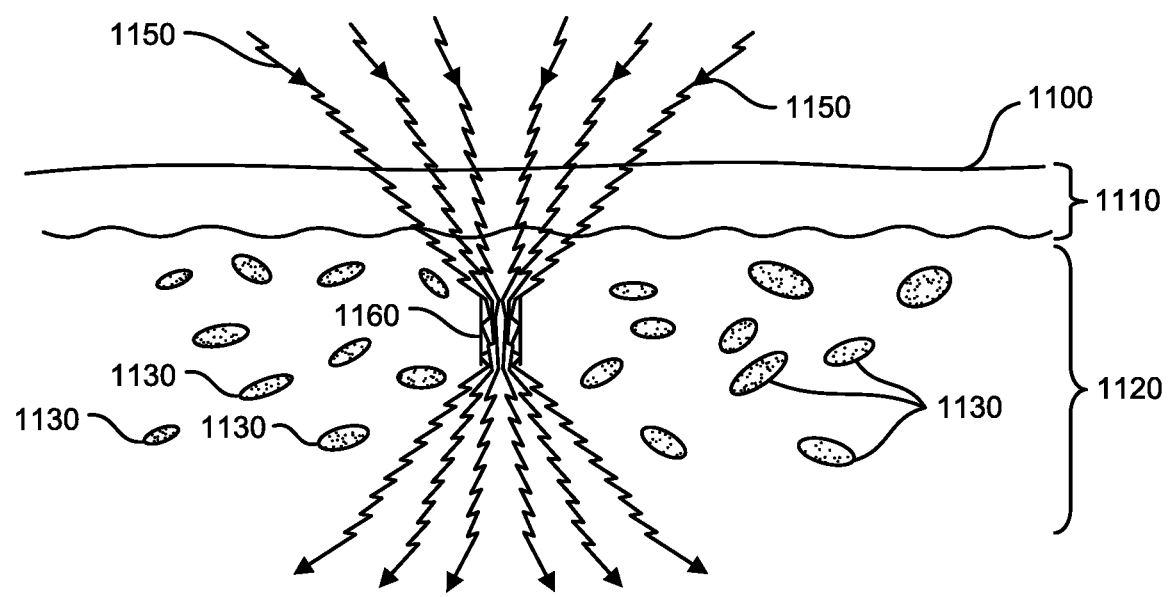
FIG. 11 is a schematic illustration of a laser beam focused into a pigmented region of a dermal layer in skin.

FIG. 11 is a schematic view of an illustration of a laser beam focused into a pigmented region of a dermal layer in a skin tissue. The skin tissue includes a skin surface 1100 and an upper epidermal layer 1110, or epidermis, which can be, e.g., about 60-120 μm thick in the facial region. The dermis can be slightly thicker in other parts of the body. For example, in general, the thickness of the epidermis can range from about 30 μm (e.g., on the eyelids) to about 1500 μm (e.g., on the palm of the hand or soles of the feet). Such epidermis may be thinner or thicker than the examples above in certain conditions of the skin, for example psoriasis. The underlying dermal layer 1120, or dermis, extends from below the epidermis 1110 to the deeper subcutaneous fat layer (not shown). Skin exhibiting deep or dermal melasma can include a population of pigmented cells or regions 1130 that contain excessive amounts of melanin. Electromagnetic radiation (EMR) 1150 (e.g., a laser beam) can be focused into one or more focal regions 1160 that can be located within the dermis 1120, or the epidermis, 1110. The EMR 1150 can be provided at one or more appropriate wavelengths that can be absorbed by melanin. EMR wavelength(s) can be selected based on one or more criteria described below.

Properties of Treatment Radiation

Figure 12A:
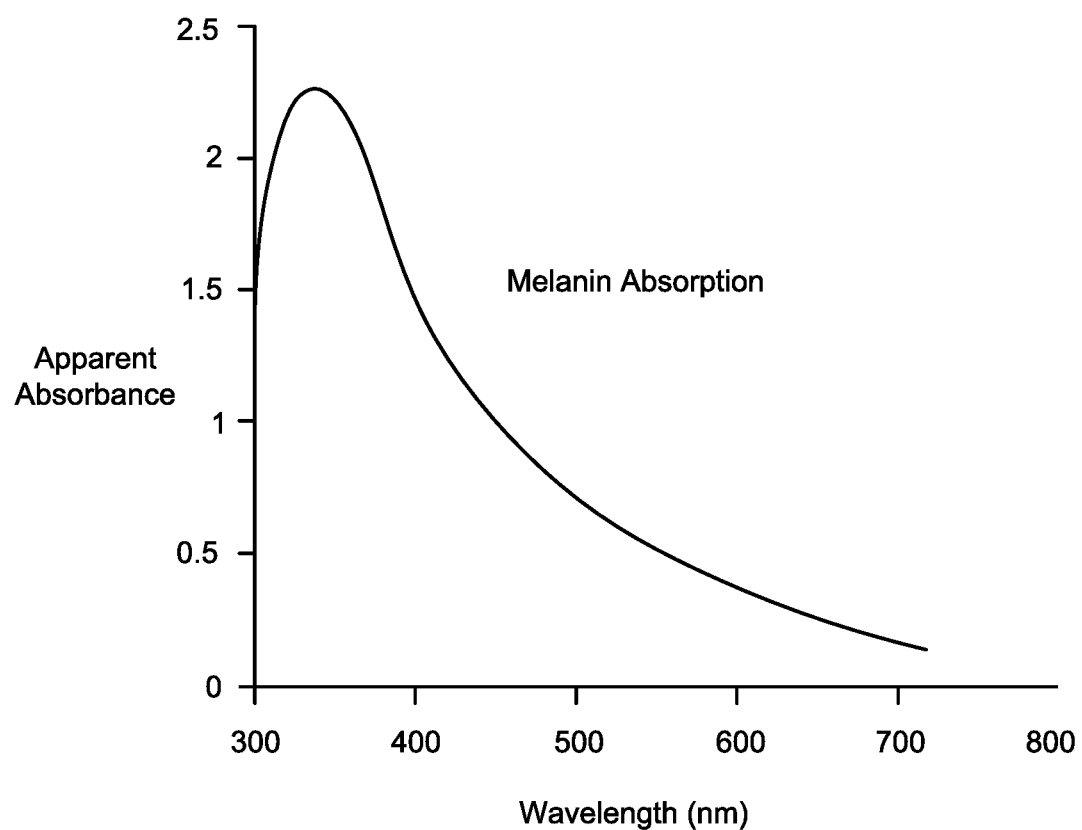
FIG. 12A is an exemplary absorbance spectrum graph for melanin.

Determination of desirable wavelength for treatment of certain skin conditions, such as pigmentary conditions and non-pigmentary conditions, can depend on, for example, the wavelength dependent absorption coefficient of the various competing chromophores (e.g., chromophore, hemoglobin, tattoo ink, etc.) present in the skin. FIG. 12A is an exemplary absorbance spectrum graph for melanin. The absorption of EMR by melanin is observed to reach a peak value at a wavelength of about 350 nm, and then decreases with increasing wavelength. Although absorption of the EMR by the melanin facilitates heating and/or disruption of the pigmented regions 1130, a very high melanin absorbance can result in high absorption by pigment in the epidermis 1110 and reduced penetration of the EMR into the dermis 1120, or the epidermis 1110. As illustrated in FIG. 12A, melanin absorption at EMR wavelengths that are less than about 500 nm are relatively high, such that wavelengths less than about 500 nm may not be suitable for penetrating sufficiently into the dermis 1120 to heat and damage or disrupt pigmented regions 1130 therein. Such enhanced absorption at smaller wavelengths can result in unwanted damage to the epidermis 1110 and upper (superficial) portion of the dermis 1120, or the epidermis 1110, with relatively little unabsorbed EMR passing through the tissue into the deeper portions of the dermis 1120.

Figure 12B:
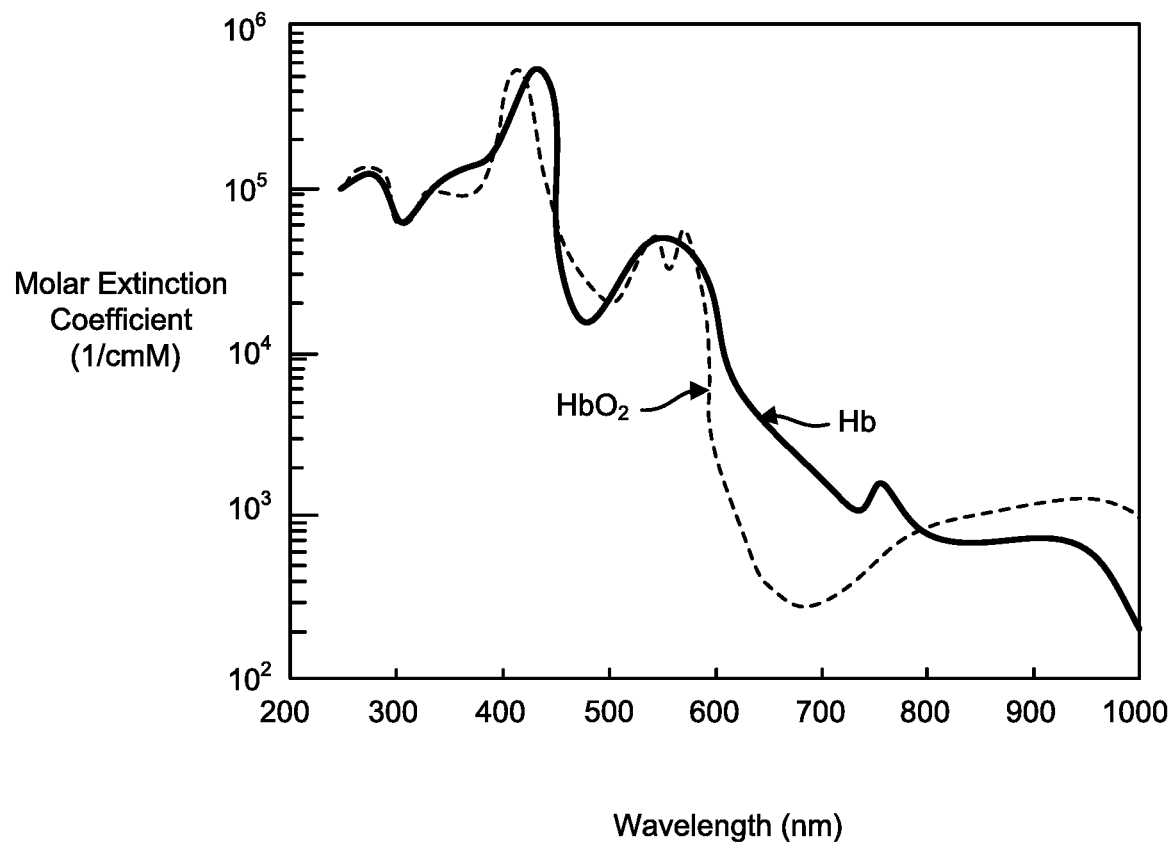
FIG. 12B is an exemplary absorbance spectrum graph for hemoglobin.

FIG. 12B is an exemplary absorbance spectrum graph for oxygenated or deoxygenated hemoglobin. Hemoglobin is present in blood vessels of skin tissue, and can be oxygenated ($HbO_2$) or deoxygenated (Hb). Each form of Hemoglobin may exhibit slightly different EMR absorption properties. As illustrated in FIG. 12B, exemplary absorption spectra for both Hb and $HbO_2$ indicate a high absorption coefficient for both Hb and $HbO_2$ at EMR wavelengths less than about 600 nm, with the absorbance decreasing significantly at higher wavelengths. Strong absorption of EMR directed into skin tissue by hemoglobin (Hb and/or $HbO_2$) can result in heating of the hemoglobin-containing blood vessels, resulting in unwanted damage to these vascular structures and less EMR available to be absorbed by the melanin.

Figure 13:
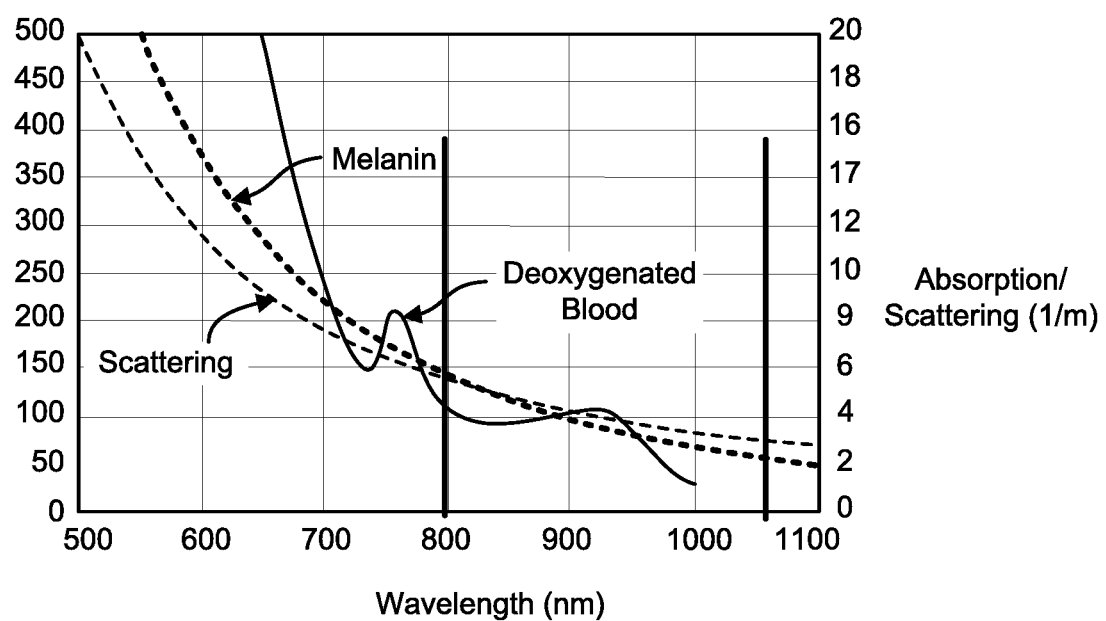
FIG. 13 illustrates a plot of the absorption coefficients of melanin and venous blood, and scattering coefficients of light in skin versus wavelength.

The choice of an appropriate wavelength for EMR can also depend on wavelength dependent scattering profile of tissues interacting with the EMR. FIG. 13 illustrates a plot of the absorption coefficient of melanin and venous blood versus wavelength. FIG. 13 also illustrates a plot of the scattering coefficient of light in skin versus wavelength. Absorption in melanin decreases monotonically with wavelength. If melanin is the target of a pigmentary condition treatment, a wavelength having a high absorption in melanin is desirable. This would suggest that the shorter the wavelength of light, the more efficient the treatment. However, absorption by blood increases at wavelengths shorter than 800 nm, thereby increasing the risk of unintentional targeting of blood vessels. In addition, as the intended target can be located below the skin surface, the role of scattering by skin (e.g., dermal layer) can be significant. Scattering reduces the amount of light that reaches the intended target. The scattering coefficient decreases monotonically with increasing wavelength. Therefore, while a shorter wavelength can favor absorption by melanin, a longer wavelength can favor deeper penetration due to reduced scattering. Similarly, longer wavelengths are better for sparing blood vessels due to a lower absorption by blood at longer wavelengths.

With the above considerations in mind, wavelengths can range from about 300 nm to about 3000 nm, and more particularly about 800 nm to about 1064 nm, can be used for targeting certain structures (e.g., melanin) in the dermis. In particular, wavelengths of about 800 nm and about 1064 nm can be useful for such treatments. The 800 nm wavelength can be attractive because laser diodes at this wavelength are less costly and readily available. However, 1064 nm can be particularly useful for targeting deeper lesions due to lower scattering at this wavelength. A wavelength of 1064 nm can also be more suitable for darker skin types in whom there is a large amount of epidermal melanin. In such individuals the higher absorption of lower wavelength EMR (e.g., about 800 nm) by melanin in the epidermis increases the chances of thermal injury to the skin. Hence, 1064 nm may be a more suitable wavelength of the treatment radiation for certain treatments for some individuals.

Various laser sources can be used for the generation of EMR. For example, Neodymium (Nd) containing laser sources are readily available that provide 1064 nm EMR. These laser sources can operate in a pulsed mode with a predetermined repetition rate. Examples of the predetermined repetition can be selected from about 1 Hz to about 100 KHz. Q-Switched Nd lasers sources may provide laser pulses having a pulse duration of less than one nanosecond. Other Nd laser sources may provide pulses having pulse durations more than one millisecond. An exemplary laser source providing 1060 nm wavelength EMR is a 20 W NuQ fiber laser from Nufern of East Granby, Conn., USA. The 20 W NuQ fiber laser provides pulses having a pulse duration of about 100 ns at a repetition rate in the range between about 20 KHz and about 100 KHz. Another laser source, is an Nd:YAG Q-smart 850 from Quantel of Les Ulis, France. The Q-smart 850 provides pulses having a pulse energy up to about 850 mJ and a pulse duration of about 6 ns at a repetition rate of up to about 10 Hz.

The systems described herein can be configured to focus the EMR in a highly convergent beam. For example, the system can include a focusing or converging lens arrangement having a numerical aperture (NA) selected from about 0.3 to 0.9 (e.g., between about 0.5 and 0.9). The correspondingly large convergence angle of the EMR can provide a high fluence and intensity in the focal region of the lens (which can be located within the dermis) with a lower fluence in the overlying tissue above the focal region. Such focal geometry can help reduce unwanted heating and thermal damage in the overlying tissue above the pigmented dermal regions. The exemplary optical arrangement can further include a collimating lens arrangement configured to direct EMR from the emitting arrangement onto the focusing lens arrangement.

The exemplary optical scanning systems can be configured to focus the EMR to a focal region having a width or spot size that is less than about 200 μm, for example, less than about 100 μm, or even less than about 50 μm, e.g., as small as about 1 μm. For example, the spot size can have ranges from about 1 μm to about 50 μm, from about 50 μm to about 100 μm, and from about 100 μm to about 200 μm. The spot size of the focal region can be determined, for example, in air. Such spot size can be selected as a balance between being small enough to provide a high fluence or intensity of EMR in the focal region (to effectively irradiate pigmented structures in the dermis), and being large enough to facilitate irradiation of large regions/volumes of the skin tissue in a reasonable treatment time.

The exemplary optical arrangement can also be configured to direct the focal region of the EMR onto a location within the dermal tissue that is at a depth below the skin surface, such as in the range from about 120 μm to about 1000 μm, e.g., between about 150 μm to about 300 μm. Such exemplary depth ranges can correspond to typical observed depths of pigmented regions in skin that exhibits dermal melisma or other targets of interest. This focal depth can correspond to a distance from a lower surface of the apparatus configured to contact the skin surface and the location of the focal region. Additionally, some embodiments can be configured for treating targets within the epidermis. For example, an optical arrangement may be configured to direct a focal region of the EMR to a location within the epidermis tissue, for example in a range from about 5 μm to 2000 μm beneath the skin surface. Still other embodiments may be configured for treating a target deep in the dermis. For example, a tattoo artist typically calibrates his tattoo gun to penetrate the skin to a depth from about 1 mm to about 2 mm beneath the skin surface. Accordingly in some embodiments, an optical arrangement may be configured to direct a focal region of the EMR to a location within the dermis tissue in a range from about 0.4 mm to 2 mm beneath the skin surface.

As described above, it can be desirable that the optical scanning system for treatment of tissues has a high numerical aperture. Additionally, it can also be desirable that the optical system be capable of treating large treatment areas (e.g., several square centimeters). This can be achieved, for example, by scanning a focused laser beam over the treatment area. However, it can be challenging to scan a treatment area with a laser beam using a high NA optical system. For example, high NA optical systems can be geometrically unfeasible for treatment of skin. Optical systems that are geometrically feasible have low numerical apertures, are bulky, and/or have long scan-times. Therefore, it is desirable to develop optical systems with high numerical apertures that can quickly and efficiently irradiate large treatment areas with a focused laser beam. Below, various embodiments of pre-objective scanning systems, post-objective scanning systems, and rotary objective scanning systems are described.

Pre-Objective Scanning System

Figure 14:
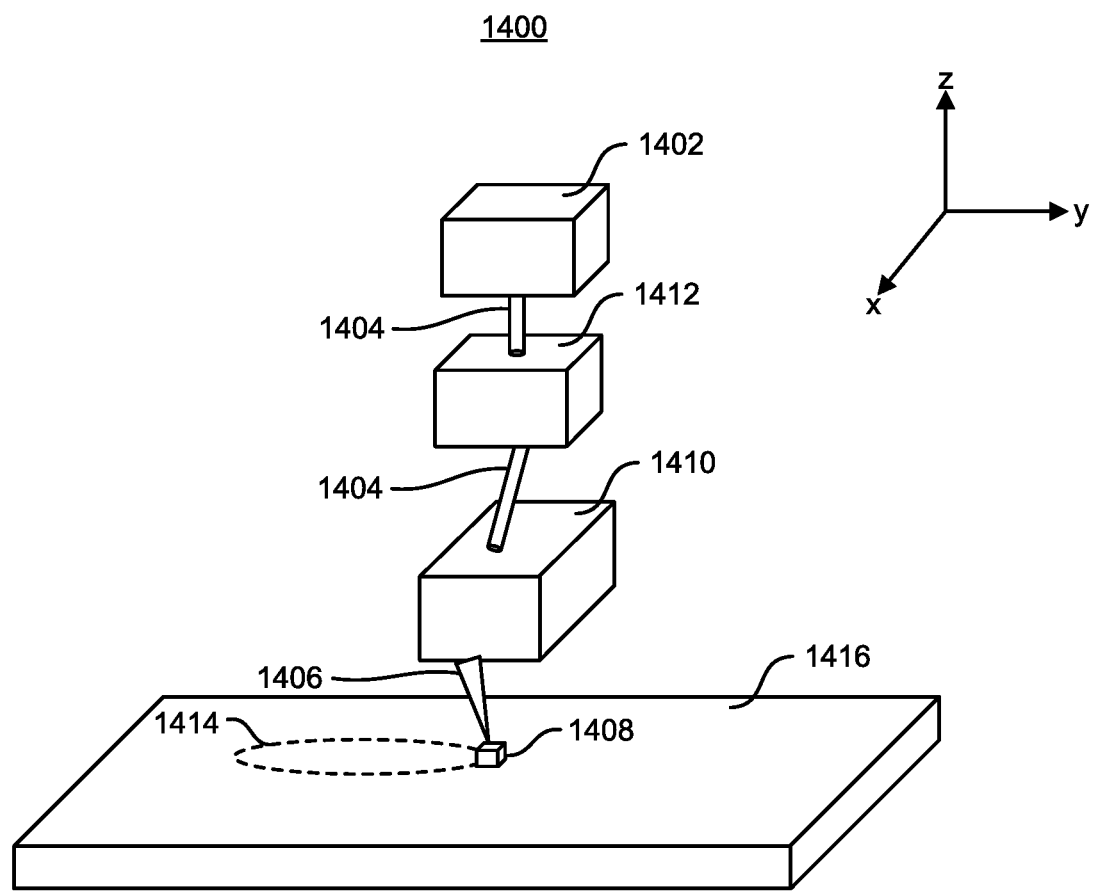
FIG. 14 is a schematic illustration of a pre-objective scanning system.

FIG. 14 is a schematic illustration of a pre-objective scanning system 1400, which includes an objective 1410 and a scanning unit 1412. The scanning unit 1412 can receive a laser beam 1404 from a laser source 1402 and direct the laser beam 1404 to the objective 1410. The objective 1410 can receive the laser beam 1404 and direct a focused laser beam 1406 to a focal volume 1408 in the treatment region of a tissue 1416 (e.g., skin). The scanning system 1412 can alter the direction of the laser beam 1404 directed towards the objective 1410. For example, the scanning system 1412 can alter the direction of the outgoing laser beam along one or more scan directions. Change in the direction of the laser beam 1404 impinging the objective 1410 can cause the focal volume 1408 to trace a treatment path 1414 in the tissue 1412. The focal volume 1408 traverses the treatment path 1414 at a scan rate. The scanning unit 1412 includes one or more optical elements that can direct the laser beam 1404 (or a portion of the laser beam 1404) to the objective 1410. The pre-objective scanning system 1400 can include a contacting surface (e.g., as shown below) that can be positioned between the objective 1410 and the tissue 1416. The contacting surface can apply pressure to the surface of the tissue 1416, and allow for dissipation of heat from the surface of the tissue 1416.

Figure 15:
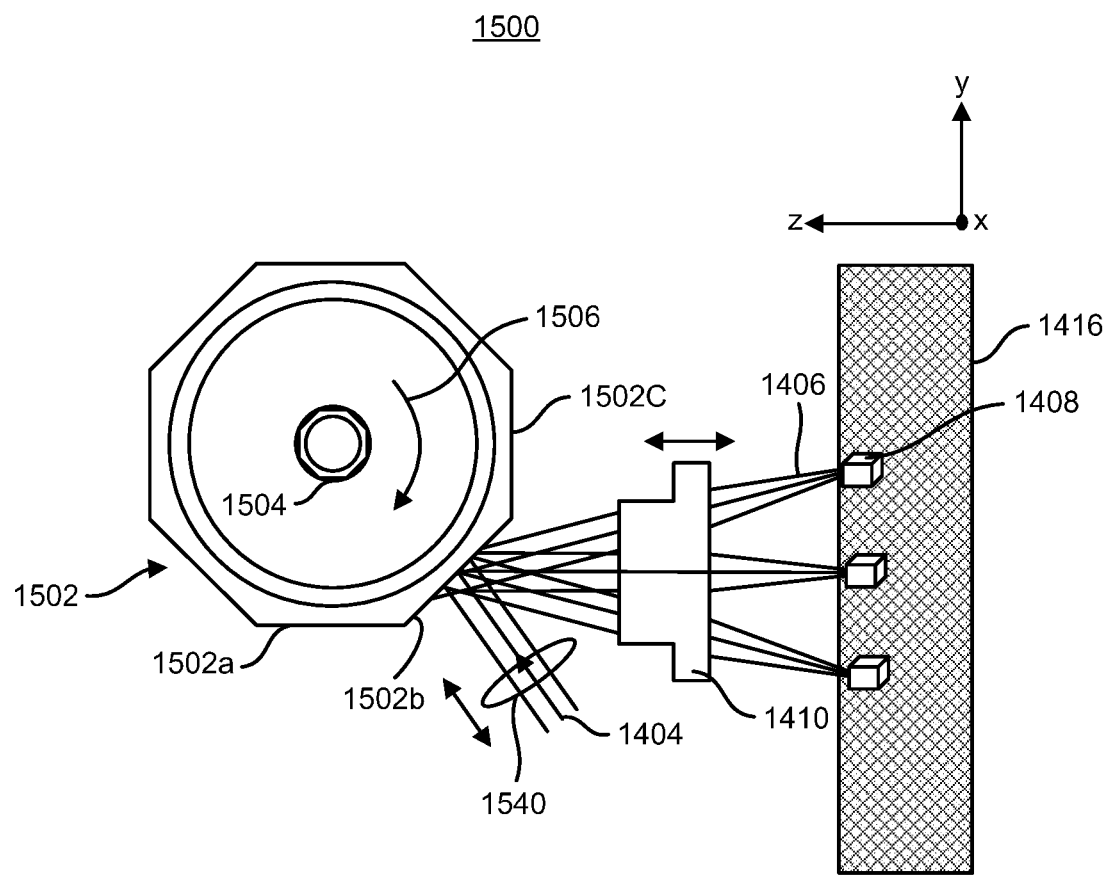
FIG. 15 is an illustration of an exemplary pre-objective scanning system.

FIG. 15 is an illustration of an exemplary pre-objective scanning system 1500. The scanning system 1500 includes a polygon scanner 1502 which can receive an incident laser beam 1404 (e.g., from a laser source 1402) and direct the incident laser beam 1404 towards an objective 1410 (e.g., f-theta lens). The outgoing direction of the incident laser beam 1404 (e.g., incidence angle with which the incident laser beam 1404 impinges on the objective 1410) can determine the location of the focal volume 1408 in the tissue 1416 (e.g., in the x-y plane). According to some embodiments, the laser source 1402 provides a plurality of laser pulses resulting in a plurality of corresponding focal volumes. A distance between two focal volumes resulting from sequential laser pulses is focal volume pitch.

The polygon scanner 1502 can include multiple reflecting surfaces (e.g., 1502 *a-c*). The polygon scanner 1502 can rotate about a polygon axis 1504 along a rotational direction 1506. As the reflecting surfaces 1502*a-c* rotate around the axis 1504 (e.g., angular position of the reflecting surfaces 1502*a-c* with respect to the axis 1504 changes), the angle of incidence of the incident laser beam 1404 in the y-z plane changes. This varies the direction of the outgoing laser beam 1404 along a first scan direction (e.g., along the y-axis). For example, if a reflecting surface (e.g., 1502*b*) is rotating about the axis 1504 along the rotational direction 1506, the direction of the outgoing laser beam sweeps from a higher y-value to a lower y-value.

The axis 1504 can tilt/rotate about the z-axis and/or the x-axis. This can cause the angle of incidence of the incident laser beam 1404 in the x-z plane to change, which varies the direction of the outgoing laser beam 1404 along a second scan direction (e.g., along the x-axis). Rotation of the polygon scanner 1502 and the rotation/tilting of the polygon axis 1504 can allow for varying of the direction of the outgoing beam 1404 that can result in the scanning of the outgoing laser beam 1404 in the x-y plane.

Based on the variation of the direction of the outgoing laser beam 1404, the objective 1410 can trace the focal volume 1408 along one or more treatment paths in the tissue 1416. For example, variation of the direction of the outgoing beam due to rotation of the polygon 1502 can cause the focal volume 1408 to move along the y-axis. Variation of the direction of the outgoing beam due to tilting of the polygon axis 1504 can cause the focal volume 1408 to move along the x-axis. In one implementation, the pre-objective scanning system 1500 can be moved along the x-axis relative to the tissue 1416. This can result in the tracing of the focal volume 1408 location along the x-axis.

Focal volume 1408 can also be moved along a third treatment path, namely, along the z-axis. This can be done by varying the objective 1410 along the z-axis (e.g., away from or towards the tissue 1416). Alternatively or additionally, lens 1540 can be placed in the beam path of the incident or outgoing laser beam 1404. By varying the position of the lens 1540 along the beam propagation direction 1542 (also referred to as optical axis), the location focal volume 1408 can be traced along the z-axis (e.g., depth of the tissue 1416).

Figure 16:
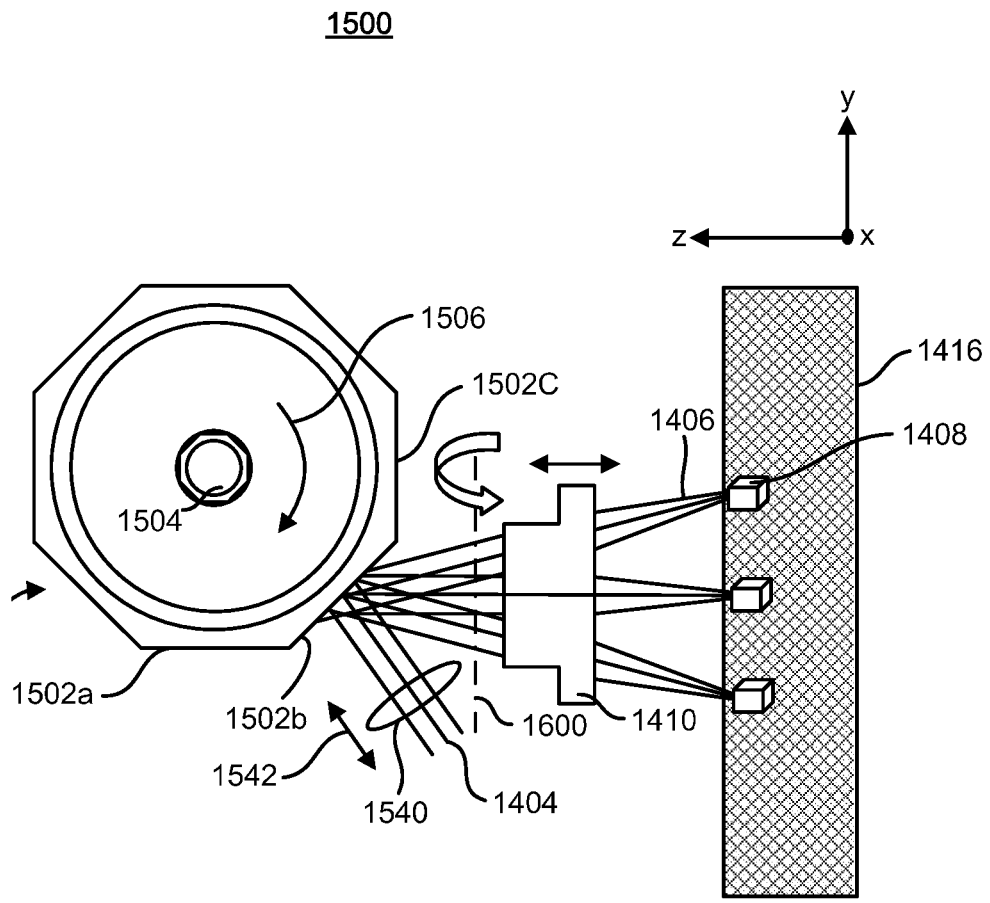
FIG. 16 illustrates a beam folding plane for the pre-objective scanning system in FIG. 6.

FIG. 16 illustrates a beam folding plane 1600 for the pre-objective scanning system 1500. The scanning system 1500 can be made compact (e.g., by reducing the extent of the scanning system 1500 along the z-axis) by folding the scanning system 1500 about the beam folding plane 1600. This can be achieved, for example, by placing a mirror (e.g., a flat mirror) in the beam folding plane and orienting the mirror parallel to the x-y plane.

Figure 17:
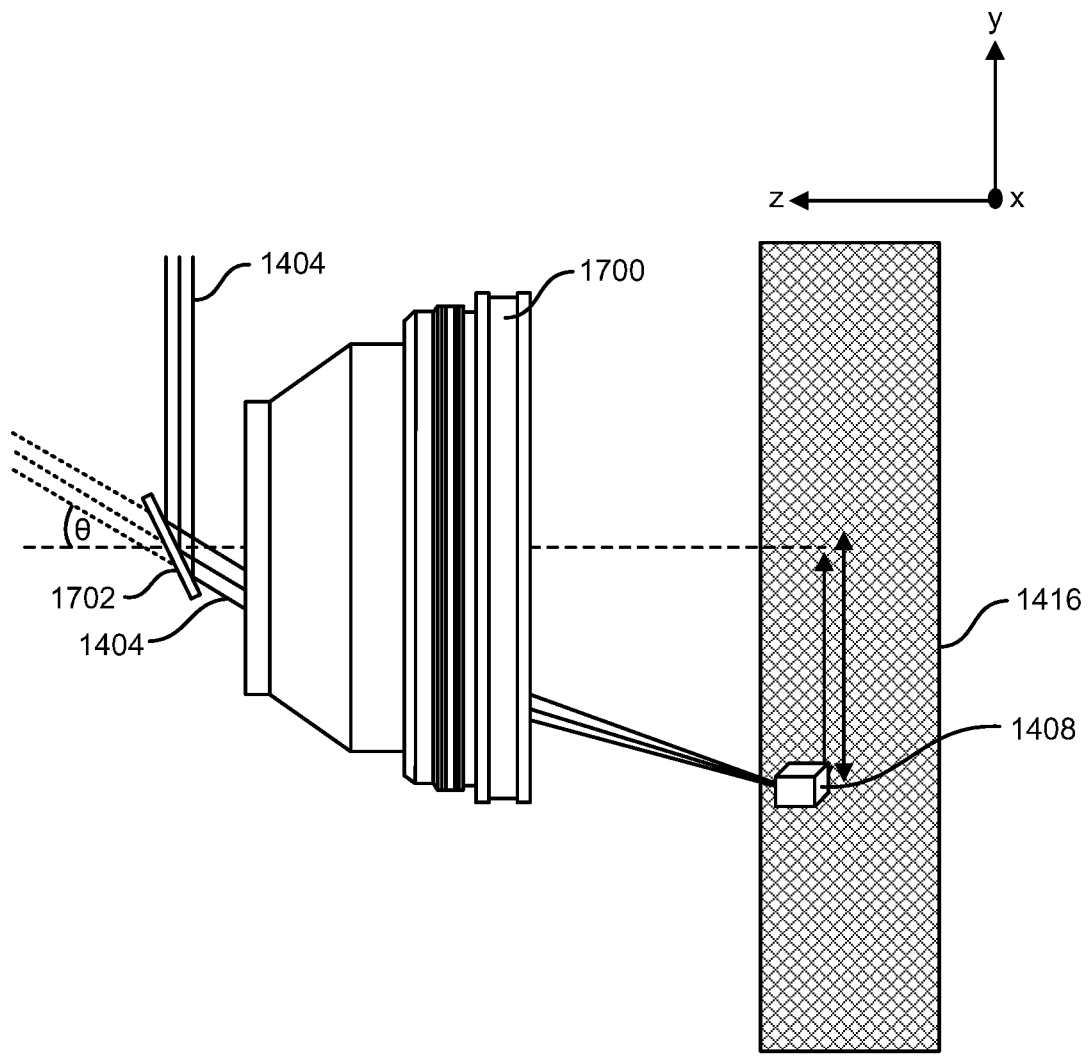
FIG. 17 illustrates an exemplary f-theta lens.

FIG. 17 illustrates an exemplary f-theta lens 1700 that can be used as an objective in the pre-objective scanning system 1500. The incident laser beam 1404 can impinge on a reflecting surface 1702 (e.g., reflective surface 1501b of the polygon scanner 1502) which can direct an outgoing laser beam 1404 to the f-theta lens 1700. The orientation of the reflecting surface 1702 can determine the incidence angle at which the outgoing laser beam 1404 impinges on the f-theta lens (e.g. angle of incidence in the y-z plane). The incidence angle can determine the location of the focal volume 1408 (e.g., along the y-axis).

Figure 18:
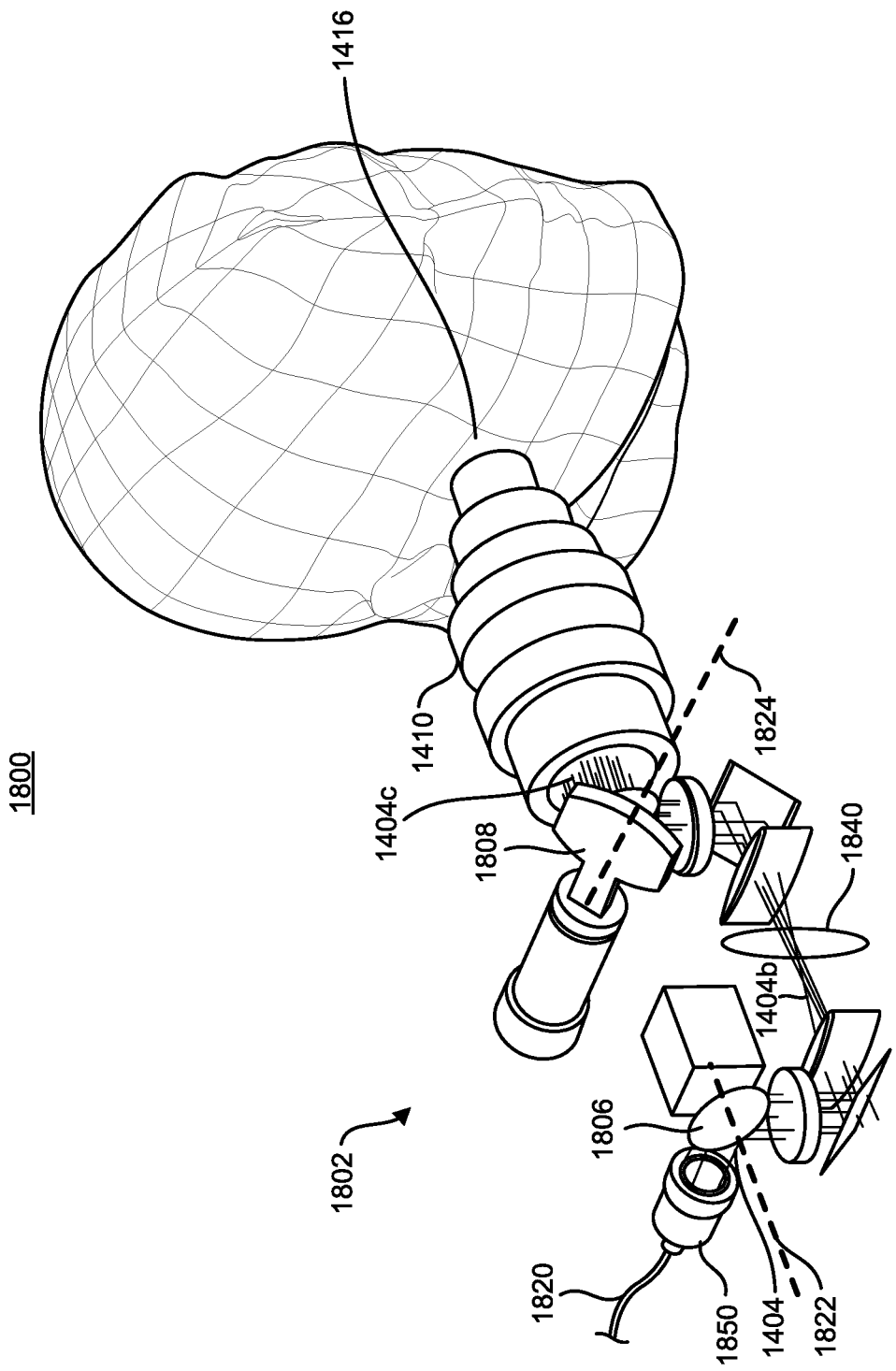
FIG. 18 is an illustration of an exemplary pre-objective scanning system.

FIG. 18 is an illustration of an exemplary pre-objective scanning system 1800. The scanning system 1800 includes a mirror system 1802 which can receive an incident laser beam 1404 (e.g., through an optical fiber 1820) and direct the laser beam 1404 towards an objective 1410 (e.g., f-theta lens). The direction of the outgoing beam 1404c can determine the location of the focal volume 1408 in the tissue 1416 (e.g., in the x-y plane).

The mirror system 1804 can include two scanning mirrors. The first scanning mirror 1806 can rotate about a first axis 1822 (e.g., clockwise counter clockwise, etc.), and the second scanning mirror 1808 can rotate about a second axis 1824 (e.g., clockwise, counter clockwise, etc.). As the first scanning mirror 1806 rotates the angle of incidence of the incident laser beam 1404 on the mirror 1806 changes. This varies the direction of the outgoing laser beam 1404b along a first scan direction (e.g., along the y-axis). As the second scanning mirror 1808 rotates the angle of incidence of the laser beam 1404b on the mirror 1808 changes. This varies the direction of the outgoing laser beam 1404c along a second scan direction (e.g., along the x-axis). Rotation of the first scanning mirror 1806 and the second scanning mirror 1808 can allow for varying of the direction of the outgoing laser beam 1404c that can result in the scanning of the outgoing laser beam 1404c in the plane of the objective 1802.

Based on the variation of the direction of the outgoing laser beam 1404c, the objective 1410 can trace the focal volume 1408 (not shown) along one or more treatment paths in the tissue 1416. For example, variation of the direction of the outgoing laser beam 1404c due to rotation of the first scanning mirror 1806 can cause the focal volume 1408 to move along a first treatment path. Variation of the direction of the outgoing laser beam 1404c due to rotation of the second scanning mirror 1808 can cause the focal volume 1408 to move along a second treatment path.

The scanning system 1800 can include a lens 1840 that can be placed in the beam path of laser beams 1404a, 1404b or 1404c. By varying the position of the lens 1840 along the beam propagation direction, the location focal volume 1408 can be traced along the depth of the tissue 1416.

Figure 19:
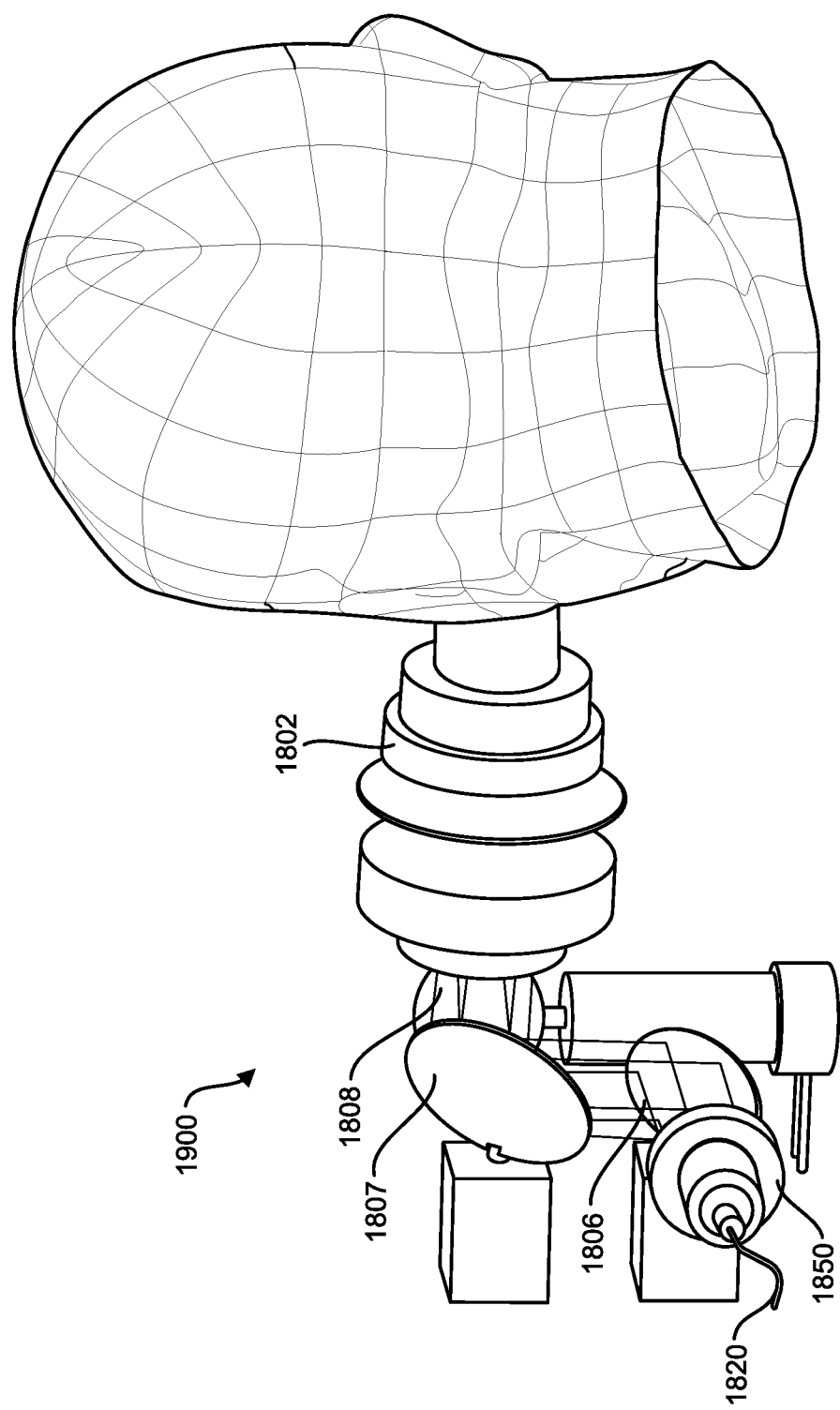
FIG. 19 is an illustration of an exemplary pre-objective scanning system.

In some implementations of the scanning mirror system, the variation in the direction of the laser beam 1404b by the first scanning mirror 1806 can be large. This can prevent the laser beam 1404b from impinging on the second scanning mirror 1808. Additionally, large angles of incidence of the laser beam 1404b on the second scanning mirror 1808 can result in curved treatment path of the focal volume. These effects can be prevented/reduced by including a third scanning mirror between the first scanning mirror 1806 and the second scanning mirror 1808. FIG. 19 is an illustration of an exemplary pre-objective scanning system 1900 that includes a third scanning mirror 1807 which is downstream from the first scanning mirror 1806 and upstream from the second scanning mirror 1808. The third scanning mirror 1807 can allow for smaller second scanning mirror 1808, and can prevent/reduce the curvature of the focal region treatment path.

Figure 20A:
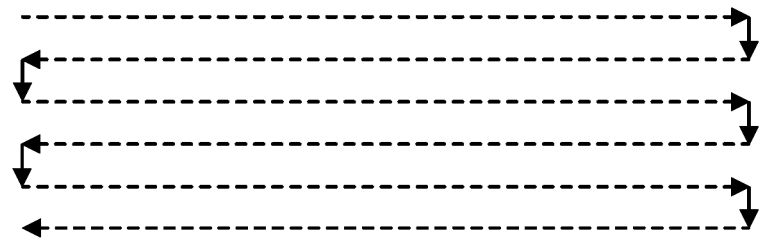
FIGS. 20A-20C illustrate exemplary scanning patterns associated with pre-objective scanning systems in FIGS. 15, 18 and 19.
Figure 20B:
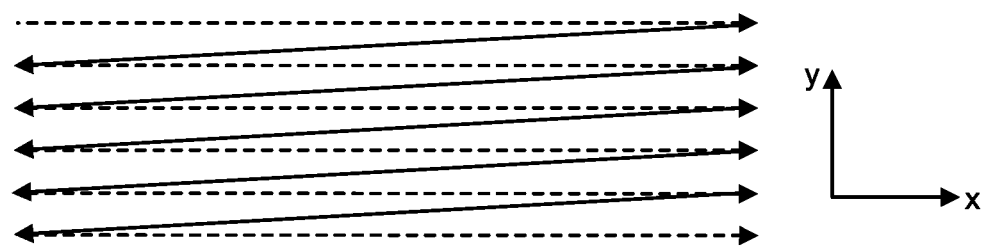
Figure 20C:
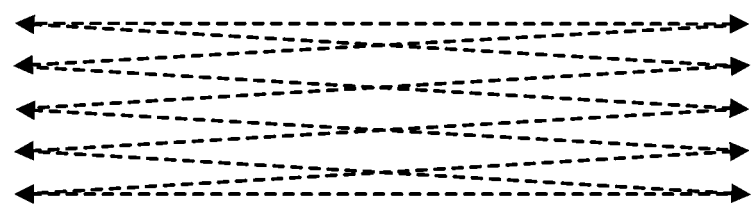

FIGS. 20A-20C illustrate various scanning patterns of an outgoing beam (e.g., outgoing laser beam 1404) from the scanning unit 1416 (e.g., polygon scanner 1502, mirror system 1802, etc.). FIG. 20A illustrates a first scanning pattern in which the outgoing beam scans in the following sequence: (a) left to right movement (e.g., along the x-axis), (b) top to down movement (e.g., along the y-axis), and (c) right to left movement (e.g., along the negative x-axis). FIG. 20B illustrates a second scanning pattern in which the outgoing beam scans in the following sequence: (a) left to right movement (e.g., along the x-axis), (b) a superposition of top to down movement and right to left movement, and (c) left to right movement. FIG. 20C illustrates a third scanning pattern in which the outgoing beam scans in the following sequence: (a) superposition of left to right movement and top to down movement, and (b) superposition of right to left movement and top to down movement. Movements of the light beam (e.g., from left to right, from right to left, from top to down, etc.) can be obtained by clockwise or anticlockwise rotation of scanning mirrors 1806, 1807, 1808, or by rotation/axis tilting of the polygon scanner 502.

Figure 21:
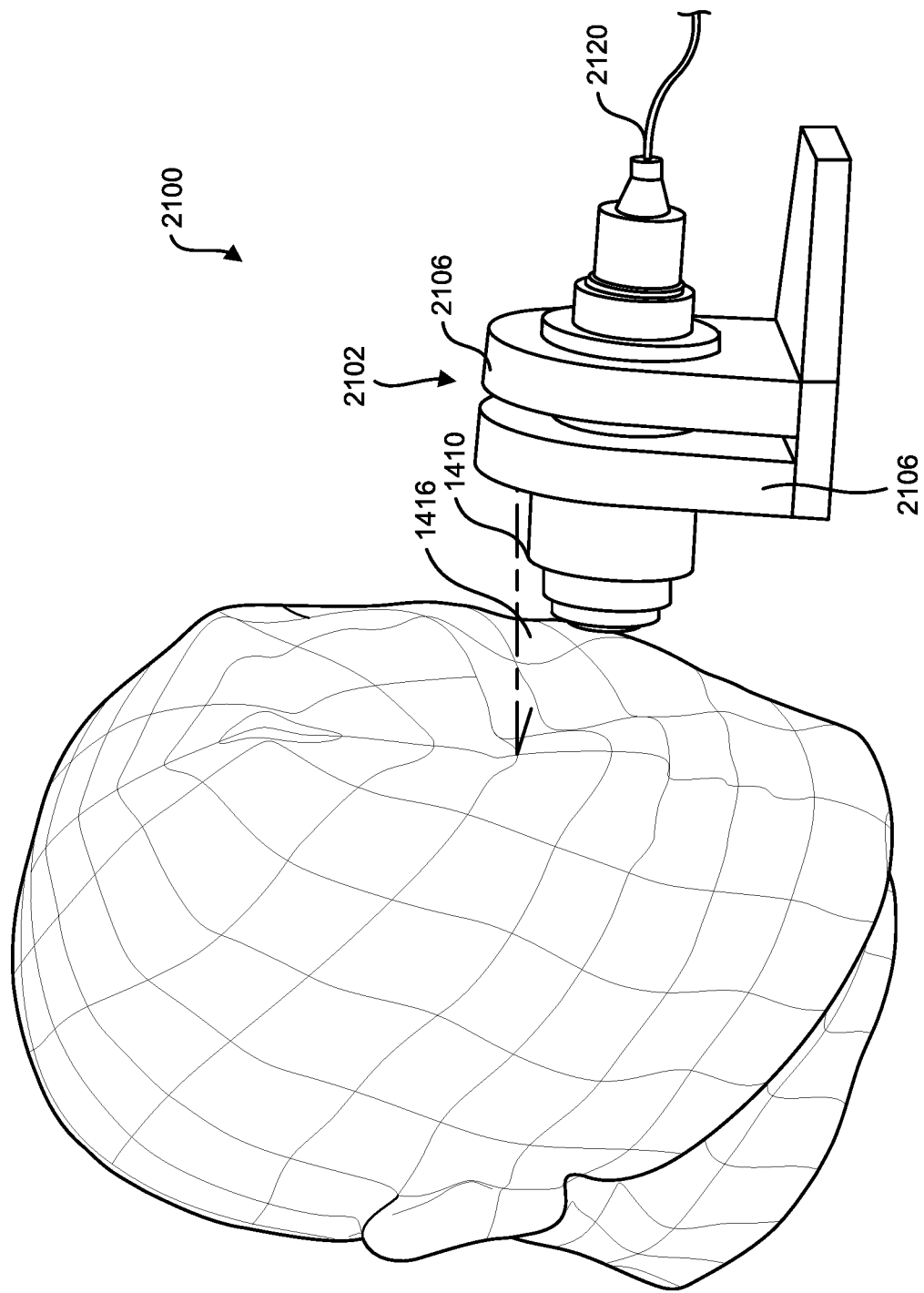
FIG. 21 is an illustration of an exemplary pre-objective scanning system.

FIG. 21 is an illustration of an exemplary pre-objective scanning system 2100. The scanning system 2100 includes a prism system 2102 which can receive an incident laser beam (e.g., through an optical fiber 2120) and transmit an outgoing beam 1405 (see above) towards an objective 1410 (e.g., f-theta lens). The direction of the outgoing beam 1405 can determine the location of the focal volume 1408 in the tissue 1416.

Figure 22:
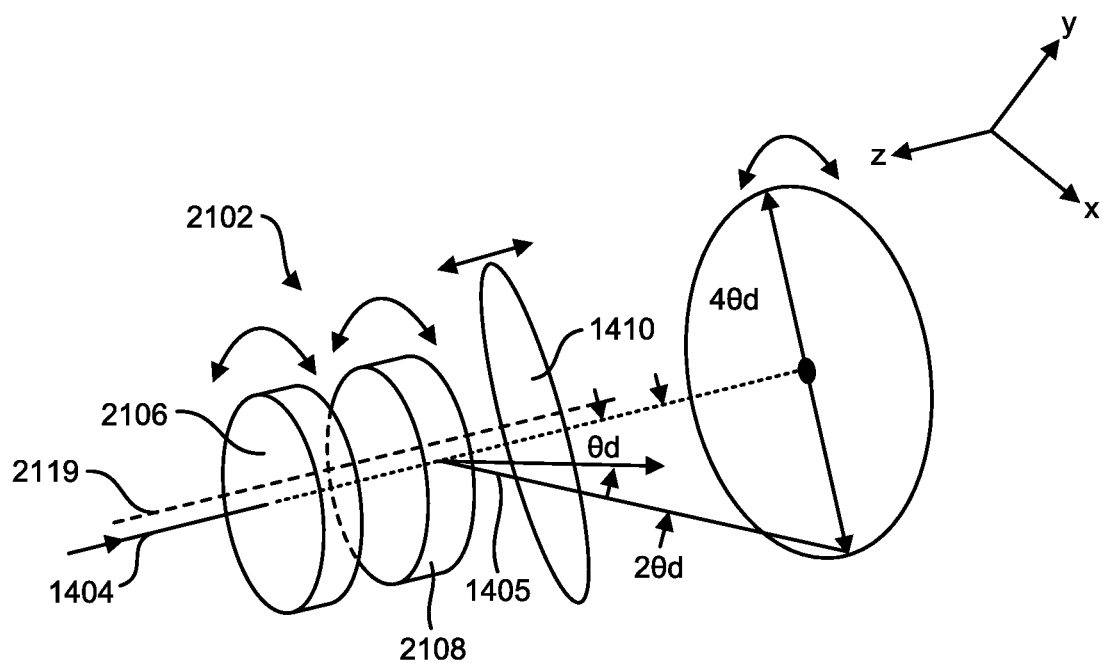
FIG. 22 illustrates an exemplary prism system of the pre-objective scanning system of the FIG. 20.

FIG. 22 illustrates a prism system 2102 that can be used with the pre-objective scanning system 2100. The prism system 2102 includes a first prism 2106 and a second prism 2108 that can rotate about a common axis 2119. Each of the prisms can alter the direction of an incident light beam by a characteristic angle. If both prisms 2106 and 2108 are perfectly aligned, the direction of an incident laser beam is altered by twice the characteristic angle. If the prisms 2106 and 2108 are perfectly misaligned, the direction of the incident laser beam remains unchanged. For all other orientations of the prisms 2106 and 2108, the direction of the incident laser beam can be altered by an angle that lies in the range between zero degrees and twice the characteristic angle.

If both the prisms 2106 and 2108 are rotating at the same angular velocity (e.g., their relative orientation does not change during rotation), the outgoing beam 1405 scans along a circular treatment path. If the prisms 2106 and 2108 are rotating at different angular velocities, their relative orientation will change during rotation. For example, the prism pair will swing between the states of perfect alignment (where the direction of the outgoing beam is deviated by twice the characteristic angle) and perfect misalignment (where the direction of the outgoing beam remains unchanged).

Figure 23:
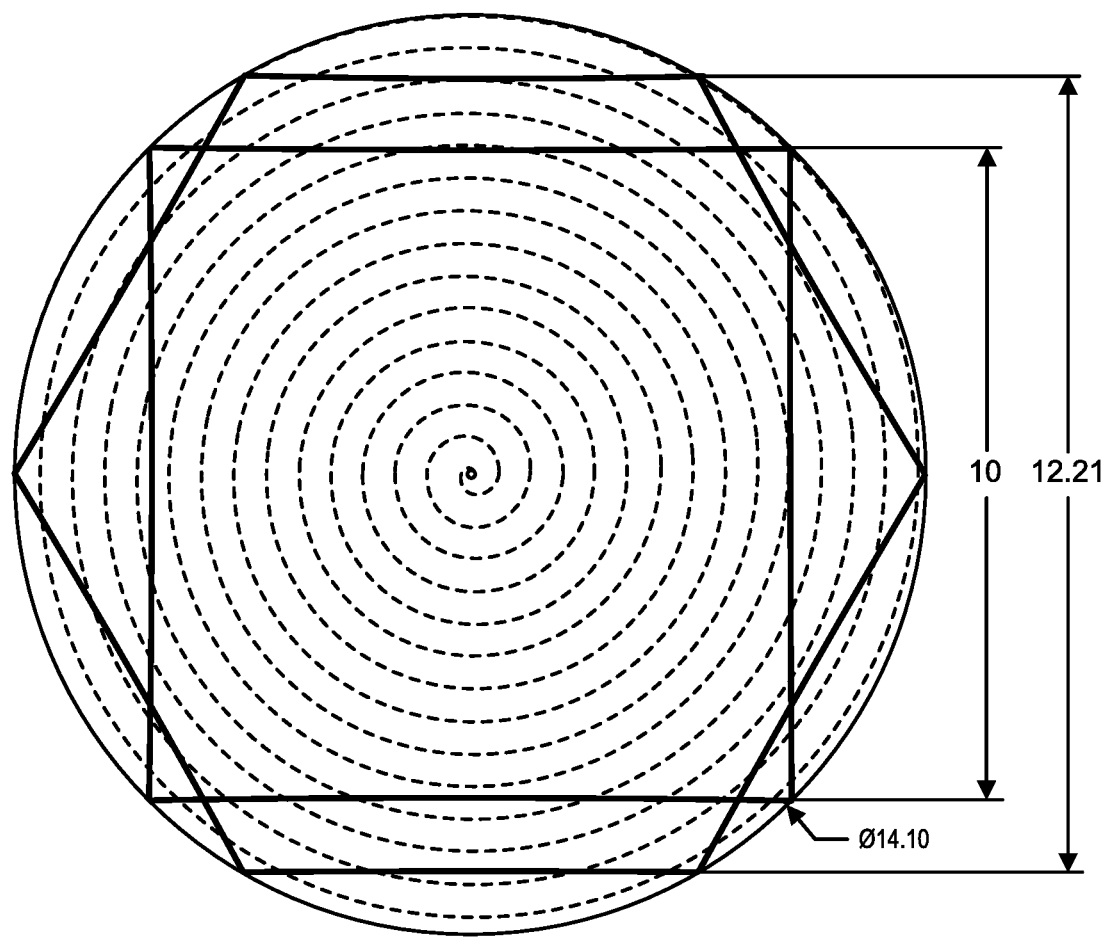
FIG. 23 illustrates an exemplary scanning pattern associated of FIG. 22.

FIG. 23 illustrates a scanning pattern of the outgoing beam 1405 resulting from the prism system 2102 where the angular velocities of the first and second prisms are different. The outgoing beam forms a spiral pattern—the outgoing beam 1405 can spiral inwards (e.g., until it reaches the center) which can be followed by outward spiral.

Figure 24:
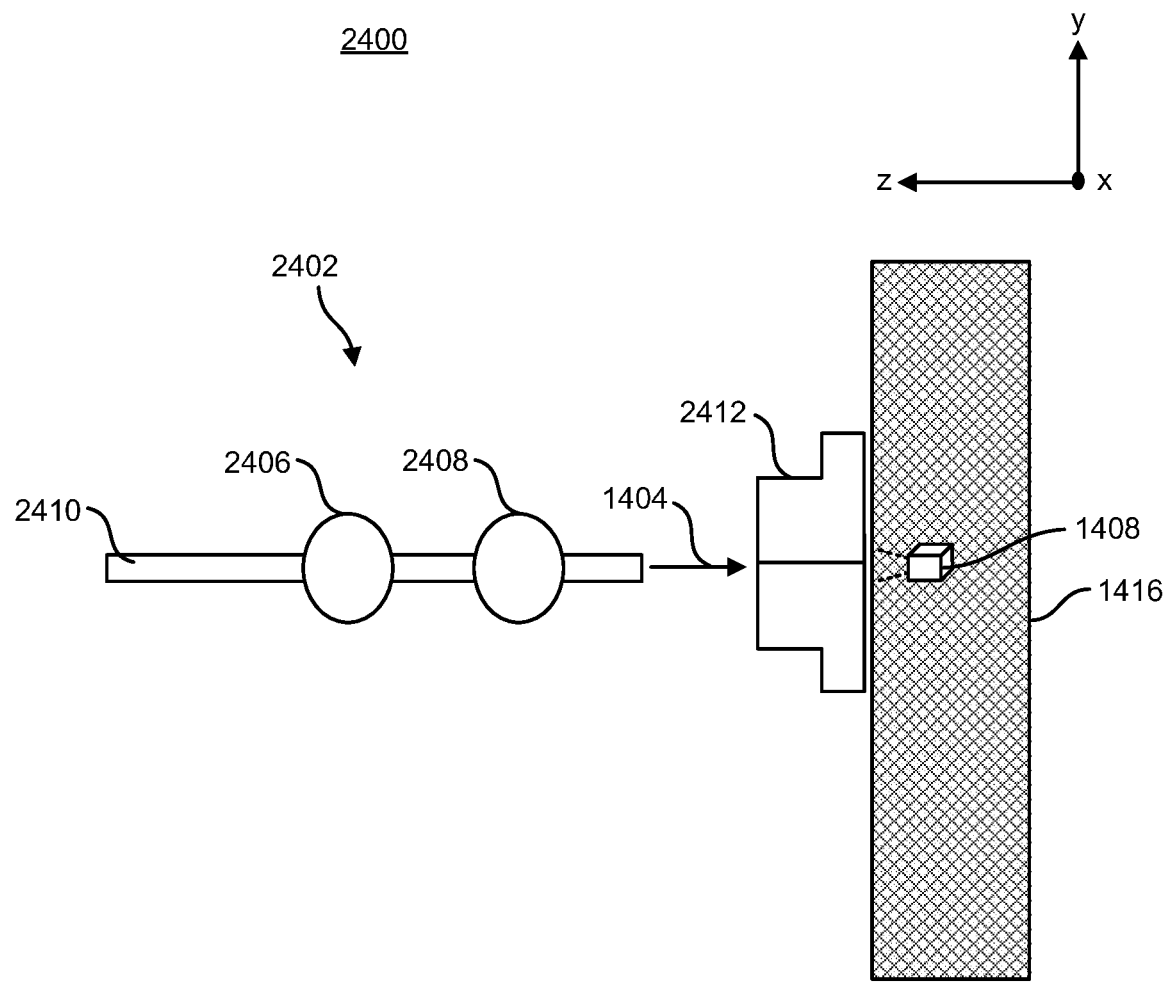
FIG. 24 is an illustration of an exemplary pre-objective scanning system.

FIG. 24 is an illustration of an exemplary pre-objective scanning system 2400. The scanning system 2400 includes a scanning unit 2402 coupled to an optical fiber 2410 that can guide the laser beam 1404. The scanning unit 2402 can include a first actuator 2406 and a second actuator 2408. The first actuator 2406 can rotate a portion of the optical fiber 2410 (e.g., tip of the fiber proximal to the objective 2412) about the x-axis. This varies the direction of the outgoing laser beam 1404 along a first scan direction (e.g., along the y-axis). The second actuator 2408 can rotate a portion of the optical fiber 2410 (e.g., tip of the fiber proximal to the objective 2412) about the y-axis. This varies the direction of the outgoing laser beam 1404 along a second scan direction (e.g., along the x-axis). Actuation by the first and second actuators can allow for varying of the direction of the outgoing laser beam 1404 that can result in the scanning of the outgoing laser beam 1404 in the plane of the objective 2412 (e.g., x-y plane). Based on the variation of the direction of the outgoing laser beam 1404, the objective 2412 (e.g., f-theta lens) can trace the focal volume 1408 along one or more treatment paths in the tissue 1416.

Figure 25:
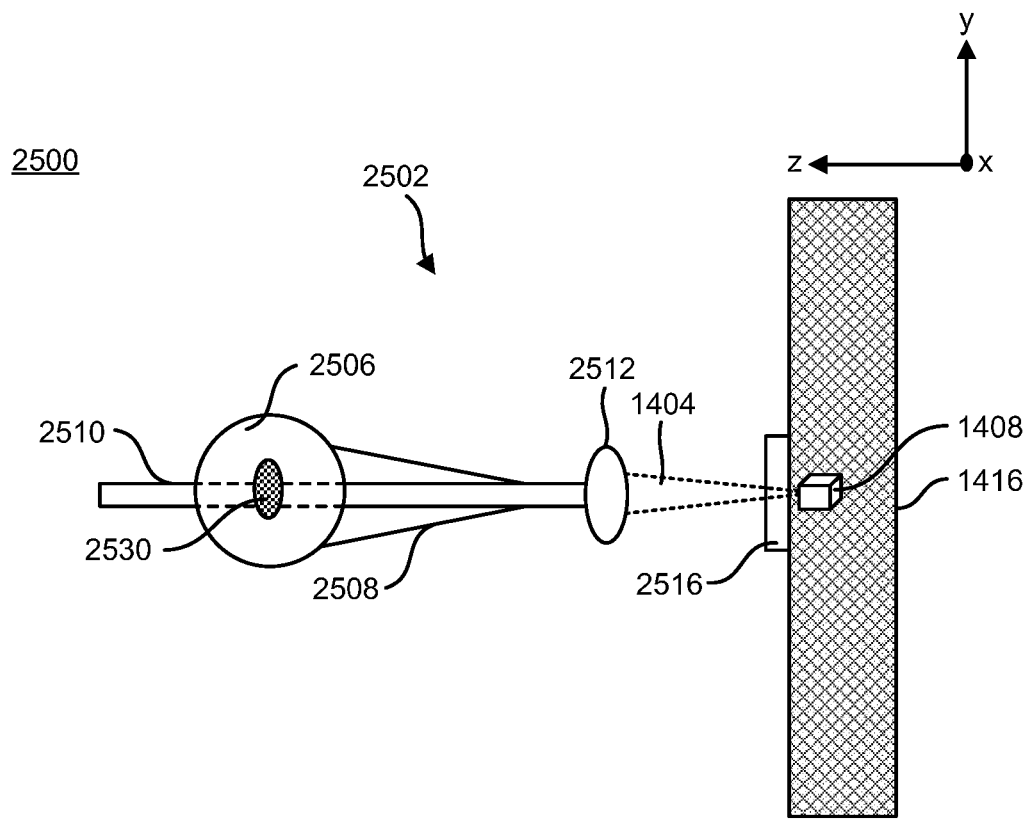
FIG. 25 is an illustration of an exemplary pre-objective scanning system.

FIG. 25 is an illustration of an exemplary pre-objective scanning system 2500. The scanning system 2500 includes a scanning unit 2502 coupled to an optical fiber 2510 (e.g., rigidly coupled) that can guide the laser beam 1404. The scanning unit 2502 can include a six-axis actuator 2506 and a support arm 2508. A portion of the optical fiber 2510 can be rigidly coupled to a mounting location 2530 on the six-axis actuator 2506. The support arm 2508 can support the portion of the optical fiber proximal to the tissue 1416.

The six-axis actuator 2506 can move the optical fiber 2510 along the x, y and z axes. Additionally or alternatively, the six-axis actuator 2506 can rotate the optical fiber 2510 about the x, y and z axes. Tip of the optical fiber 2510 can be coupled to the objective 2512 that can focus the outgoing laser beam 1404 to a focal volume 1408 in the tissue 1416. The pre-objective scanning system 2500 can also include a contacting surface 2516 that can lie in the optical path of the outgoing laser beam 1404 between the objective 2512 and the tissue 1416.

The focal volume 1408 can be moved along a first treatment path (e.g., along the x axis) by rotating the optical fiber around the y-axis. The focal volume 1408 can also be moved along a second treatment path (e.g., along the y axis) by rotating the optical fiber around the x axis. In some implementations, it may be desirable to alter the distance between the tip of the optical fiber 2510 and the tissue 1416 (e.g., by moving the tip of the optical fiber along the z-axis) during rotation (e.g., along the x axis, y axis, etc.) to ensure that the focal volume 1408 remains at a fixed depth in the tissue 1416.

Post-Objective Scanning System

Figure 26:
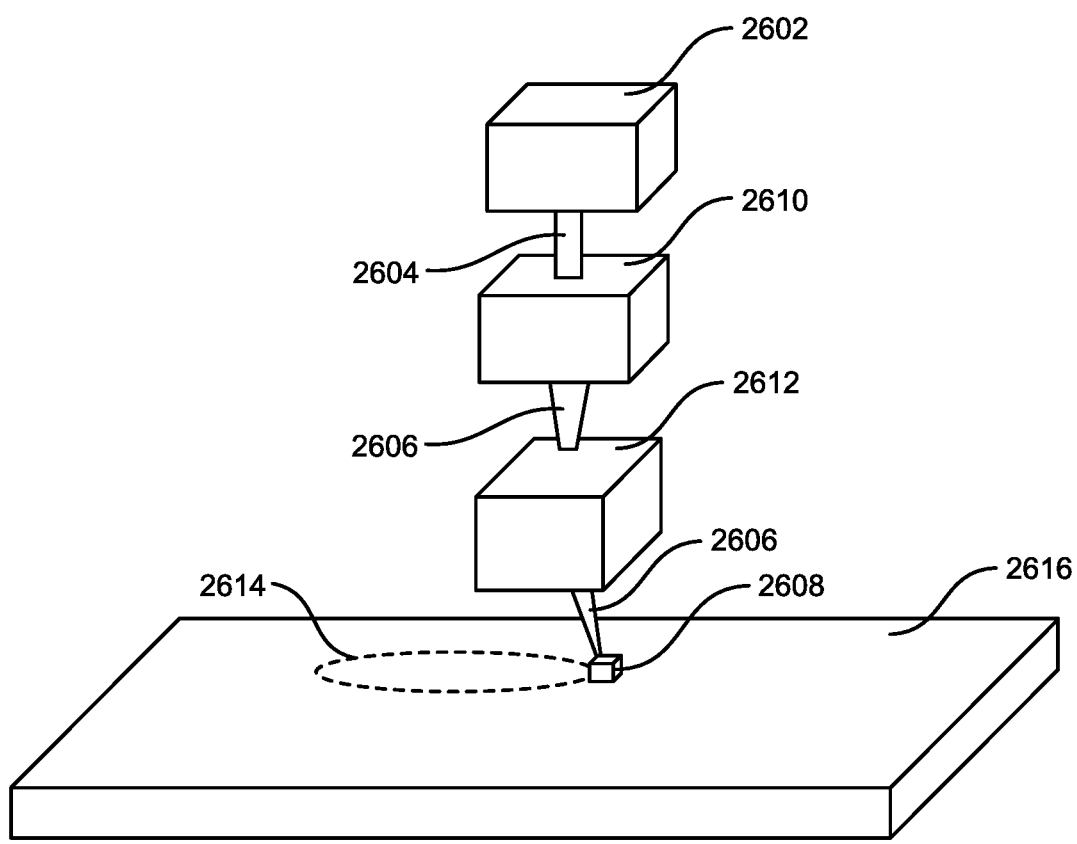
FIG. 26 is a schematic illustration of a post-objective objective scanning system.

FIG. 26 is a schematic illustration of a post-objective scanning system 2600. The post-objective scanning system 2600 includes an objective 2610 and a scanning unit 2612. The objective 2610 can receive a laser beam 2604 from a laser source 2602 and direct focused laser beam 2606 to the scanning unit 2612. The scanning unit 2612 can receive the focused laser beam 2606 and direct it to a focal volume 2608 in the treatment region of a tissue 2616 (e.g., skin). The scanning system 2612 can allow the focal volume 2608 to trace a treatment path 2614. The scanning unit 2612 includes one or more optical elements that can direct the laser beam 2606 (or a portion of the laser beam 2606) towards the skin.

Figure 27:
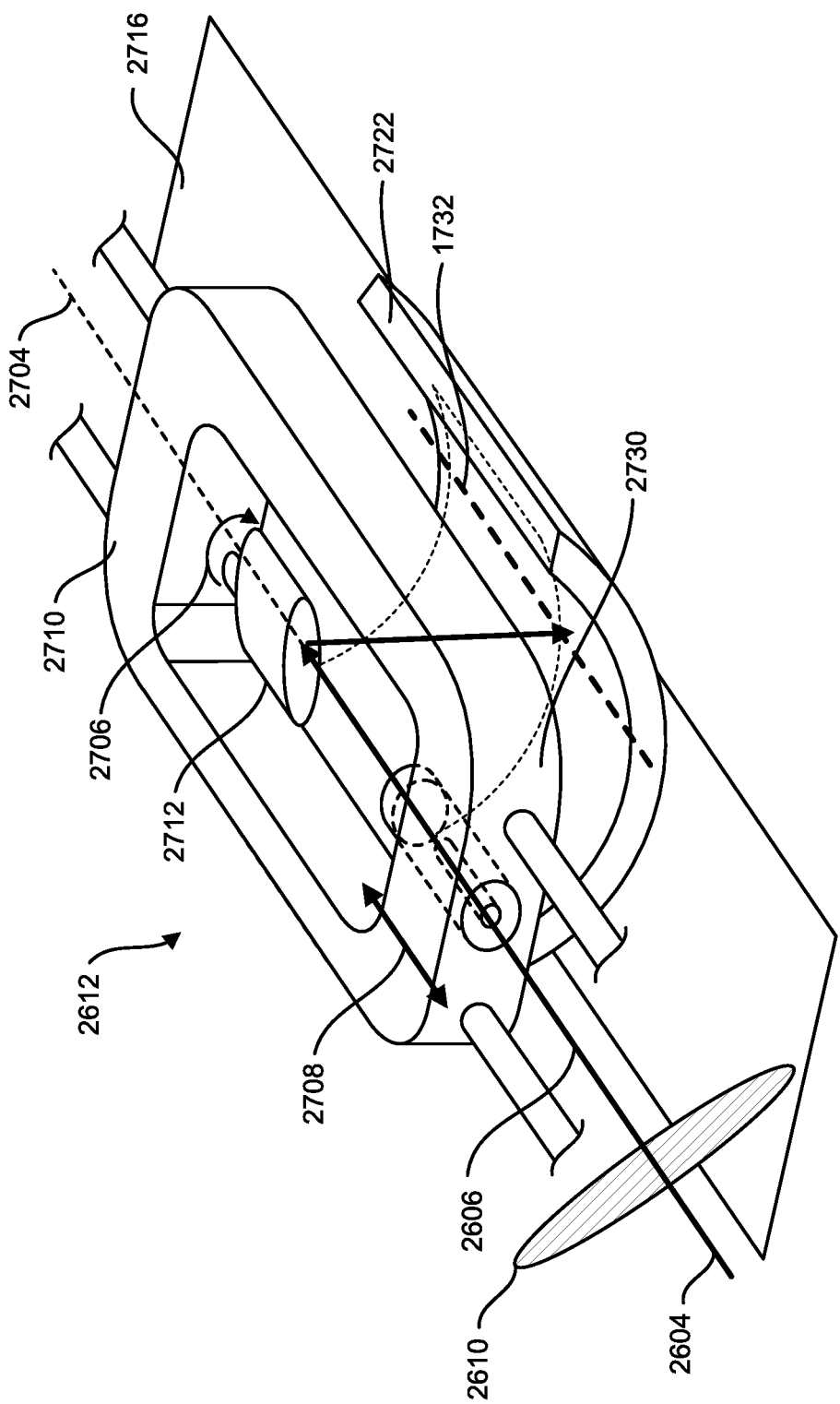
FIG. 27 is a perspective view of optical elements in an exemplary scanning unit.

FIG. 27 is a perspective view of the arrangement of optical elements in an exemplary scanning unit 2612. The scanning unit 2612 includes a housing having a support platform 2710 and a contacting surface 2722. The scanning unit 2612 also includes an optical element 2712 that is rotatably coupled to the support platform 2710. The optical element 2712 can rotate about the axis 2704 along a rotational direction 2706. The scanning unit 2612 can receive the focused laser beam 2606 from the objective 2610, and can direct the focused laser beam 2606 to the focal volume 2608 in the tissue 2616. As the scanning unit 2612 rotate, the focal volume 2608 can trace a first treatment path 2730 in the tissue 2616. The scanning unit 2612 can also translate along the axis 2704 that can result in the focal volume 1608 tracing a second treatment path 2732 in the tissue 2616.

The contacting surface 2722 can be curved and can apply pressure the surface of the tissue 2616. This can allow for efficient transfer of optical energy by the focused beam 2606 reflected by the optical element 2712 to a focal volume 2608 in the treatment region of the tissue 2616. The contacting surface 2722 or portions thereof can allow for dissipation of heat from the surface of the tissue 2616. In one implementation, the contacting surface can be made of sapphire.

The scanning systems described in this application (e.g., pre-objective scanning system 1400 and post-objective scanning system 2600) can include an interface (also referred to as "base," "window," or "contacting surface") that can stabilize the treatment region (e.g., surface of the tissue 1416, 2616, etc.) and/or facilitate control and uniformity of the irradiation profile of the laser beam (e.g., beam 1406, 2606, etc.). For example, the interface can immobilize the treatment region through application of pressure and/or by including a gel pad between the interface and the treatment region. Pressure applied by the interface on the treatment region can be detected by a pressure detector. The interface can also include a contact sensor that detect relative motion between the skin and the interface. Pressure provided by the interface on the treatment region can also blanche (or remove some blood from) the volume of treatment region being irradiated. This can result in selectivity of absorption of focused laser beam (e.g., 1406, 2606, etc.) by the treatment region (e.g., pigmented cells in the treatment region) while reducing a risk of unwanted damage to blood vessels.

The interface can cool/dissipate heat from the treatment region that can be generated, for example, by heating of the treatment region due to the focused laser beam. The interface can be made of materials suitable for heat dissipation (e.g., sapphire, diamond, glass, and the like). In some implementations, the interface can include a cooling system that can prevent the temperature of the treatment region from crossing a threshold temperature. The cooling system can include a temperature sensor that can detect the temperature of the treatment region. If the temperature exceeds the threshold temperature, a user can be notified and/or a cooling unit (e.g., Peltier device, cryospray, conductive cold conduit, and the like) can be activated to cool the treatment region.

Example parameters according to some embodiments of pre-objective and post-objective beam scanners are disclosed below in Table 2.

TABLE 2

Example Pre- and Post-Objective Scanner Parameters

| Parameter | Typical Minimum | Nominal | Typical Maximum |
|---|---|---|---|
| Treatment Path Distance (mm) | 0.5 | 10 | 100 |
| Focal Volume Pitch, x-y plane (μm) | 1 | 25 | 1000 |
| Focal Volume Pitch, z-axis (μm) | 1 | 50 | 200 |
| Scan Speed, x-y plane (mm/S) | 0.001 | 1000 | 50000 |
| Numerical Aperture of Objective (—) | 0.3 | 0.5 | 0.9 |
| Focal Region Depth Beneath Skin Surface (μm) | 20 | 200 | 2000 |
| Average Power of Laser (W) | 0.5 | 10 | 30 |
| Repetition Rate of Laser (Hz) | 1 | 20000 | C.W. |
| Pulse Duration of Laser (nS) | 1 | 100 | 100000 |
| Energy per Pulse (mJ) | 0.1 | 2 | 20 |
| Wavelength (nm) | 300 | 1064 | 3000 |

Rotary Objective Scanning System

Figure 28:
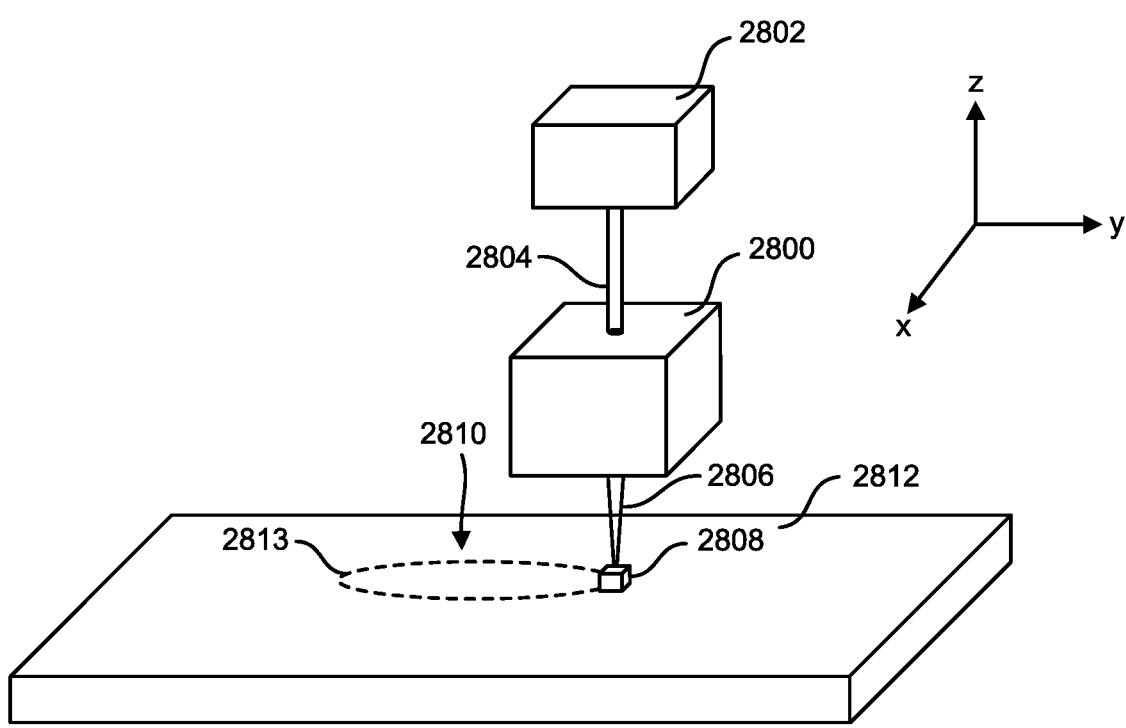
FIG. 28 is a schematic illustration of a rotary objective scanning system.

FIG. 28 is a schematic illustration of a rotary objective scanning system 2800. The rotary objective scanning system 2800 can receive a laser beam 2804 from a laser source 2802. The scanning system 2800 includes an objective (not shown) that focus the laser beam 2804 and directs a focused laser beam 2806 to a focal region 2808 in the treatment region 2810 of a tissue 2812 (e.g., skin). As the objective moves (e.g., relative to the scanning system 2800 and/or due to movement of the entire scanning system 2800), the focal region can trace a treatment path 2813 through the treatment region 2810. The treatment path 2813 can have path geometries (e.g., circular, elliptical, and the like). The scanning system 2800 includes optical elements that can direct the laser beam 2804 (or a portion of the laser beam 2804) towards the moving objective.

The scanning system 2800 can also include an interface (also referred to as "base," "window," or "contacting surface") that can stabilize the treatment region 2810 and/or facilitate control and uniformity of the irradiation profile. For example, the interface can immobilize the treatment region 2810 through application of pressure and/or by including a gel pad between the interface and the treatment region. Pressure applied by the interface on the treatment region 2810 can be detected by a pressure detector. The interface can also include a contact sensor that detect relative motion between the skin and the interface. Pressure provided by the interface on the treatment region can also blanche (or remove some blood from) the volume of treatment region being irradiated. This can result in selectivity of absorption of focused laser beam 2806 by the treatment region (e.g., pigmented cells in the treatment region) while reducing a risk of unwanted damage to blood vessels.

The interface can cool/dissipate heat from the treatment region 2810 that can be generated, for example, by heating of the treatment region 2810 due to the focused laser beam 2806. The interface can be made of materials suitable for heat dissipation (e.g., sapphire, diamond, glass, and the like). In some implementations, the interface can include a cooling system that can prevent the temperature of the treatment region from crossing a threshold temperature. The cooling system can include a temperature sensor that can detect the temperature of the treatment region. If the temperature exceeds the threshold temperature, a user can be notified and/or a cooling unit (e.g., Peltier device, cryospray, conductive cold conduit, and the like) can be activated to cool the treatment region.

The rotary objective scanning system can have various embodiments. Two exemplary embodiments of the rotary objective scanning system include an in-plane rotary objective scanning system and a transverse rotary objective scanning system, both of which are described below.

In Plane Rotary Objective Scanning System

Figure 29B:
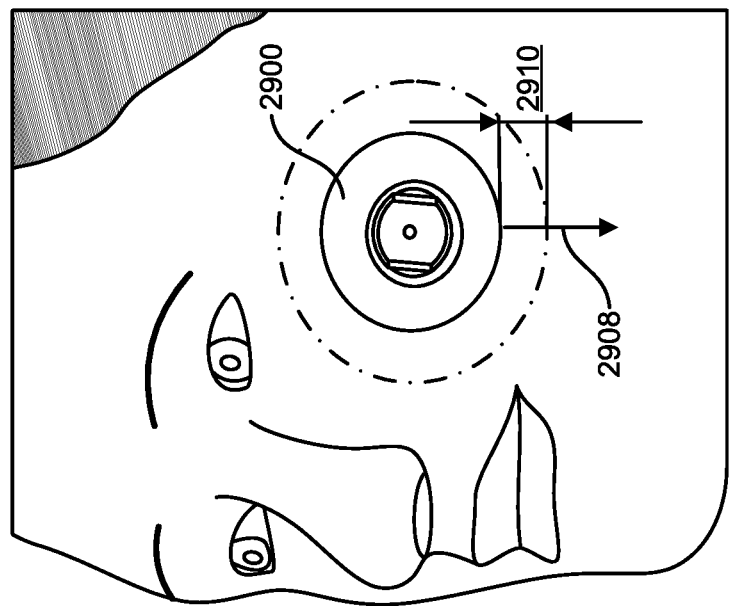
FIG. 29B is a top-down view of an in-plane rotary objective scanning system located over the treatment region.
Figure 29A:
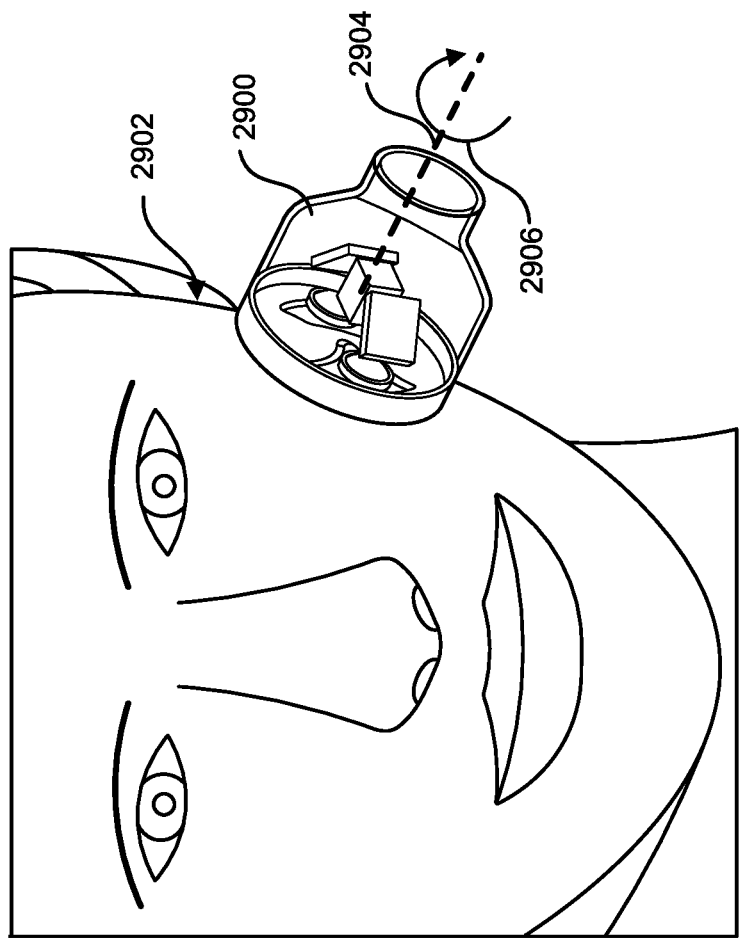
FIG. 29A is a perspective view of an in-plane rotary objective scanning system located over a treatment region.

FIG. 29A is a perspective view of an in-plane rotary objective scanning system 2900 located over a treatment region 2902. The scanning system 2900 includes an objective that can move relative to a housing of the scanning system. For example, the objective can rotate (e.g., clockwise, counter-clockwise, and the like) about an axis 2904 of the scanning system 2900. As the objective rotates (along a rotational scan direction 2906), it can traverse a rotational scan path relative to the treatment region 2902. FIG. 29B is a top-down view of the in-plane rotary objective scanning system 2900. The axis 2904 (which projects out of the page) can move (along a second scan direction 2908) relative to the treatment region 2902. For example, the scanning system 2900 can be moved by hand or by an actuator resulting in the displacement of the axis 2904. If both the rotation of the objective (about the axis 2904) and displacement of the axis 2904 occurs approximately at the same time (e.g., simultaneously), the objective is displaced by a certain distance after it completes a rotation. This displacement of the objective is referred to as a translational pitch 2910 of the scanning system. The translational pitch can be varied, for example, by changing the angular velocity of the rotating platform and/or speed of translation of the axis 2904.

Figure 30:
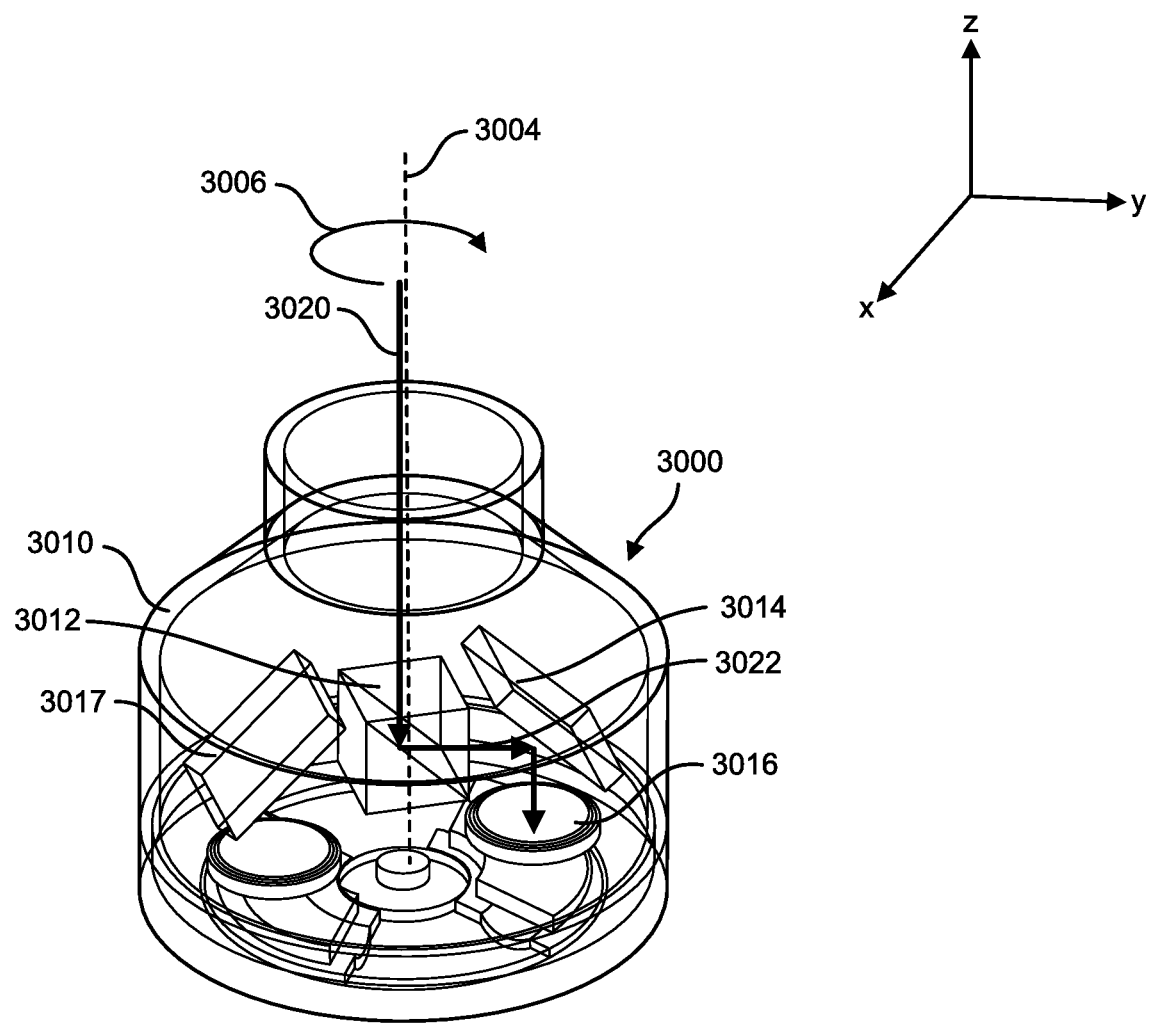
FIG. 30 is a perspective view of the arrangement of optical elements in an exemplary in-plane rotary objective scanning system.

FIG. 30 is a perspective view of the arrangement of optical elements in an exemplary in-plane rotary objective scanning system 3000. The scanning system 3000 comprises a housing 3010 and a rotating platform (not shown) that can rotate (along a rotational scan direction 3006) about the axis 3004. The rotating platform 3032 (shown in FIG. 31) can be rigidly coupled to a first optical element 3012 (e.g., beam splitter, mirror, etc.), a first mirror 3014 and an objective 3016 that rotate with the rotating platform. A laser beam 3020 can impinge on the first optical element 3012 that can reflect a first reflected beam 3022. The first reflected beam 3022 can be redirected towards the objective 3016 by the first mirror 3014. The objective 3016 can focus the first reflected beam 3022 to a focal region in the treatment region.

As disclosed herein, a first optical element is said to be "upstream" from a second optical element if a light beam impinges on the first optical element prior to impinging on the second optical element. For example, in FIG. 30, first optical element 3012 is considered to be upstream from the first mirror 3014 as the laser beam 3020 first impinges on the first optical element 3012 before a portion of the laser beam 3020 (i.e., first reflected beam 3022) is directed to the first mirror 3014. Alternately, the first mirror 3014 is considered to be "downstream" from the first optical element 3012.

Figure 31:
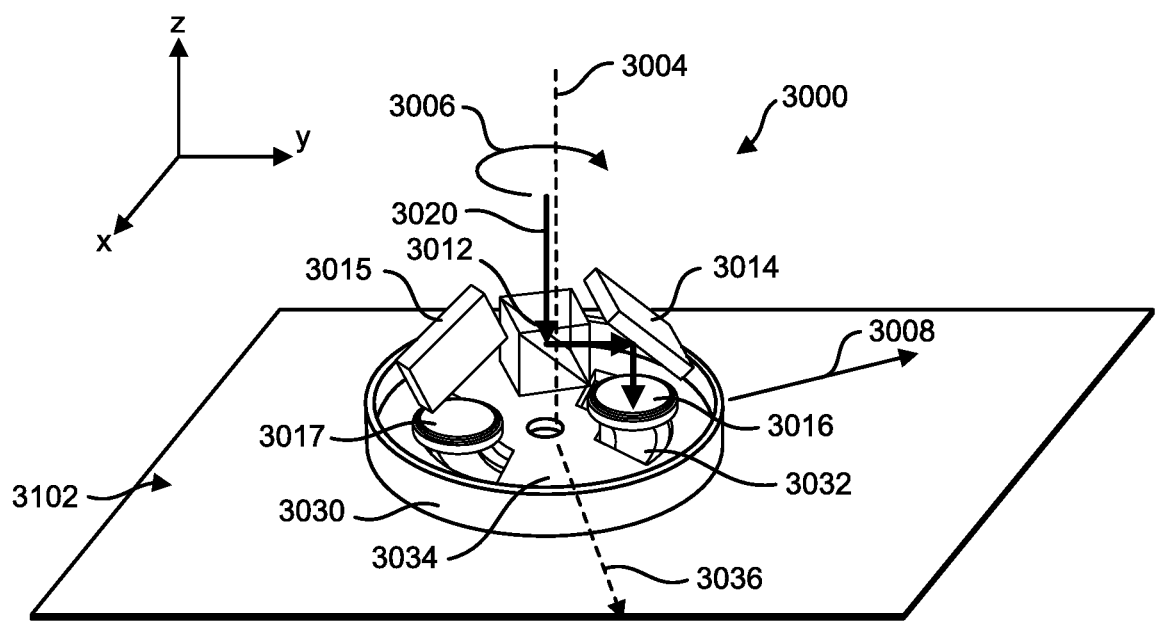
FIG. 31 is the perspective view of the in-plane rotary objective scanning system of FIG. 30 located over a tissue surface.

FIG. 31 is the perspective view of the in-plane rotary objective scanning system 3000 located over a tissue surface 3102. The objective 3016 can rotate about the axis 3004 along the rotational scan direction 3006. The axis 3004 is configured to translate along the lateral scan direction 3008. The housing 3010 of the scanning system 3000 can include a platform 3030 that can support the rotating platform 3032. The platform 3030 abuts/interfaces with the tissue surface 3102 and separates the objective 3016 from the tissue surface 3102. As described above, the platform 3030 (also referred to as "interface) can stabilize and/or cool the tissue surface 3102 (or tissue portions below the tissue surface 3102).

The scanning system 3000 can also include an optical barrier 3034 that can prevent the first reflected beam 3022 from impinging on the objective 3016. The optical barrier 3034 can be oriented substantially perpendicular to the second scan direction (e.g., by rotating about the axis 3004). For example, the optical barrier axis 3036 can be oriented substantially perpendicular to the lateral scan direction 3008. As the lateral scan direction 3008 changes, the optical barrier 3034 can be reoriented to remain orthogonal to the lateral scan direction 3008. The lateral scan direction 3008 (or a change thereof) can be determined, for example, by an accelerometer. Change in the lateral scan direction 3008 can be signaled to an actuator coupled to the optical barrier 3034 by the accelerometer. Based on the signal from the accelerometer, the actuator can reorient the optical barrier 3034.

The optical barrier 3034 can prevent the irradiation of portions of the tissue surface located along the optical barrier axis 3036 (e.g., when the optical barrier axis region is substantially perpendicular to lateral scan direction 3008 ["peripheral regions"]). This can be desirable as there is a possibility of providing excessive optical energy by the first reflected beam 3022 in the peripheral regions (see discussion below). In another implementation, first reflected beam 3022 can be turned off when the objective 3016 is oriented substantially orthogonal to lateral scan direction 3008 (e.g., when the objective 3016 passes over the peripheral regions). The extent of the peripheral region (e.g., range of angular values with respect to the lateral scan direction 3008) can be determined based on scan density (or optical energy delivered per unit area) that is considered safe for treatment.

It can be desirable that the scanning system 3000 remains stable (e.g., does not wobble) as rotating platform 3032 rotates about the axis 3004. This can be done, for example, by designing the scanning system 3000 such that its center of mass remains close to the axis 3004 during rotation. This can be done, for example, by including a second mirror 3015 and a second objective 3017 that are rigidly coupled to the rotating platform 3034. The radial locations of the second mirror 3015 and the second objective 3017 are determined based on the location of the center of mass of the scanning system 3000 prior to coupling with the second mirror 3015 and the second objective 3017. In some implementations, a portion of the incident laser beam 3020 can be directed to the second objective 3017 via the second mirror 3015. The second objective 3017 can focus the received portion of the laser beam to a second focal region in the treatment region. The second focal region can also trace treatment paths which can be different from the treatment paths of the first focal region associated with objective 3016.

Figure 32A:
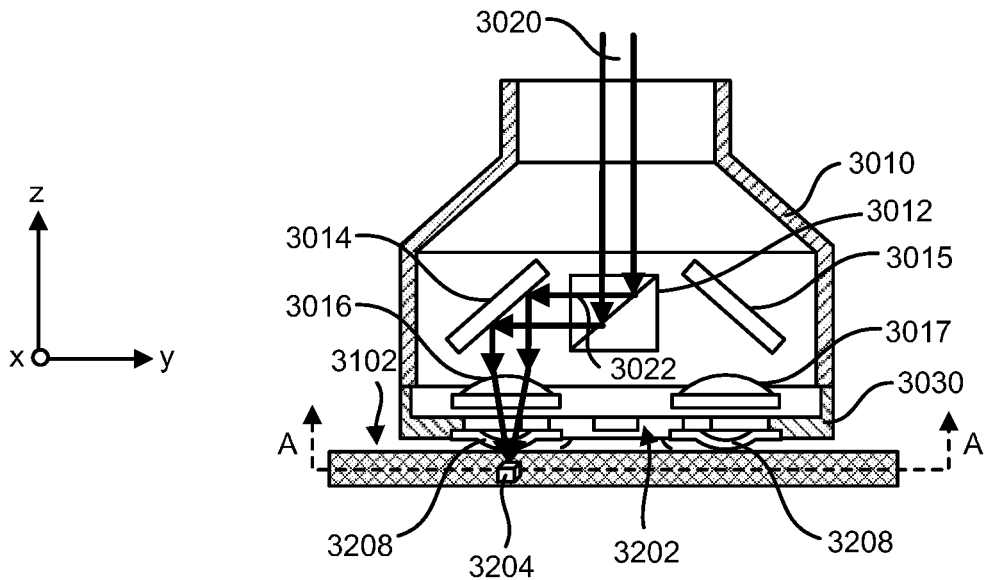
FIG. 32A is a side view of the in-plane rotary objective scanning system of FIG. 30 located over a tissue surface.

FIG. 32A is a side view of the in-plane rotary objective scanning system of FIG. 30 located over a tissue surface 3102. The incident laser beam 3020 is described using two light rays that are indicative of a beam width the incident laser beam 3020 extends laterally (e.g., perpendicular to the direction of propagation of the laser beam 3020). A person skilled in the art would recognize that the beam width of a laser beam can refer to, for example, the full-width-half-maximum of the lateral intensity profile of the laser beam 3020. The beam width may not change upon reflection from the first optical element 3012 and the first mirror 3014. Upon focusing of the first reflected beam 3022 by the objective 3016, the beam width can reduce to a focal volume 3204 in the tissue (e.g., beneath the tissue surface 3102). The platform 3030 can include a contacting surface 3202 that abuts the tissue surface 3102. The contacting surface 3202 is located in a plane (e.g., in the x-y plane parallel to the tissue surface 3102) and separates the objective 3016 and the tissue surface 3102. The contacting surface can include an elevated region 3208 that can project towards the surface of the tissue surface 3102. The plane of the contacting surface and the axis 3004 intersect (e.g., orthogonally). The contacting surface is discussed in greater detail below.

Figure 32B:
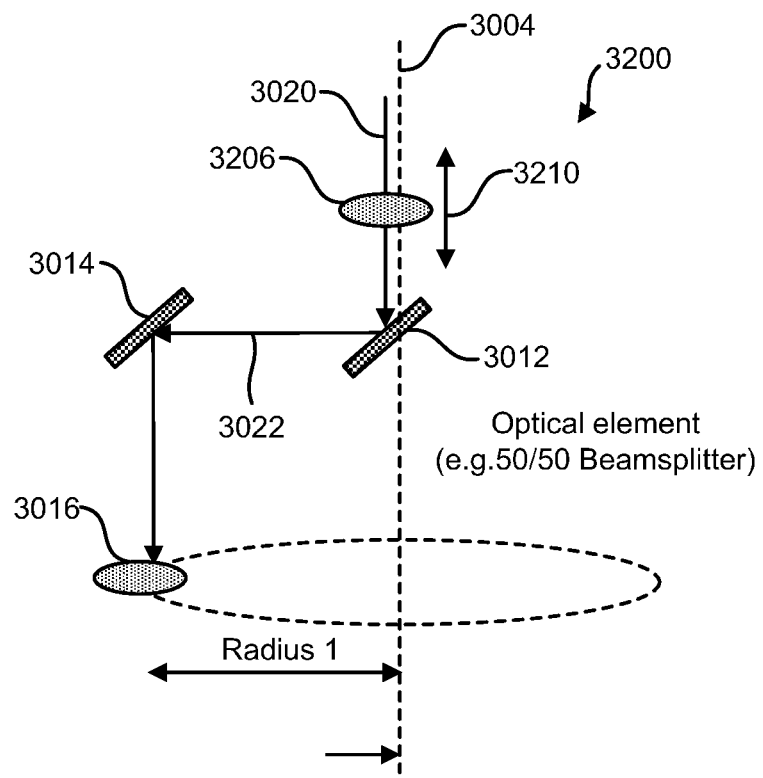
FIG. 32B is a schematic illustration of a first optical sub-system of FIG. 32A.

FIG. 32B is a schematic illustration of a first optical sub-system 3200 of FIG. 32A. The first optical sub-system 3200 includes the first optical element 3012, the first mirror 3014 and the rotating objective 3016. The first optical sub-system 3200 is rigidly coupled to a rotating platform (e.g., rotating platform 3032). In one implementation, first optical element 3012 can be a mirror. The reflectivity of the first optical element 3012 determines the intensity of the first reflected beam 3022 relative to the incident laser beam 3020. For example, if the reflectivity of the mirror is approximately 1, almost all of the light in the laser beam 3020 is reflected in the form of first reflected beam 3022. Alternately, in some implementations, the first optical element 3012 can be a beam splitter that can reflect a first portion of the laser beam 3020 and transmit a second portion of the laser beam 3020. This implementation will be further discussed below.

The first optical element 3012 can be located at a first radial distance ("Radius 1") from the axis of rotation 3004. As the objective rotates about the axis 3004 along a rotational scan direction, it can trace a rotational scan path. Because both the first optical element 3012 and the reflecting mirror 3014 rotates with the objective 3012, the incident laser beam 3020 can be directed to the first optical element 3012 during the traversal of the rotational scan path by the first optical element 3012.

The motion of the objective 3016 along the rotational scan path can result in the motion of the focal volume 3204 in the x-y plane. The focal volume can also be varied along the z-direction (e.g., varying the depth of the focal volume 3204 with respect to the tissue surface 3102). This can be done, for example, by placing a lens 3206 (or multiple lenses) in the beam path of laser beam 3020 and/or beam path of light beam 3022 and moving the lens along the beam path. In one implementation, a lens 3206 can be placed upstream from the first optical element 3012 and its position can be varied along the beam path 3210. In other implementation, the lens 3206 can be placed between in the optical path of first reflected beam 3022 (e.g., downstream from first optical element 3012 and upstream from the first mirror 3014, downstream from mirror 3014 and upstream from objective 3016, etc.). Alternately, the depth of the focal volume 3204 can also be varied by moving the objective 3016 towards or away from the tissue surface 3102.

Figure 33:
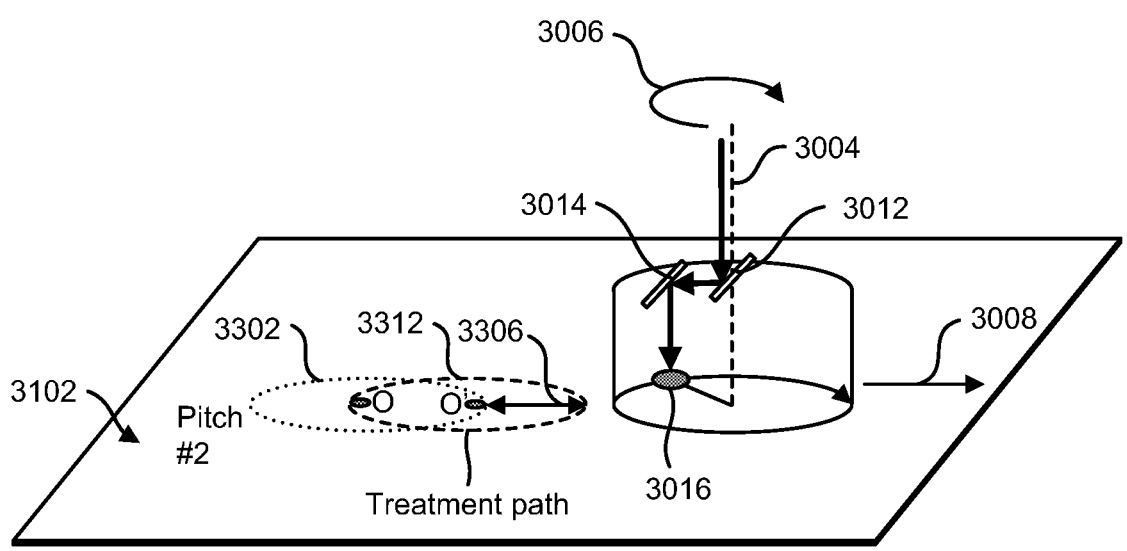
FIG. 33 is a schematic illustration of the scan paths associated with the objective of the in-plane rotary objective scanning system of FIG. 30.

FIG. 33 is a schematic illustration of the scan paths associated with the objective 3016 of the in-plane rotary objective scanning system 3000. As described before, the objective 3016 can rotate along a rotational scan direction 3006 about the axis 3004, and the axis 3004 can translate along the lateral scan direction 3008. FIG. 33 illustrates two exemplary scan paths 3302 and 3312 corresponding to the stationary location of the axis 3004 at O and O', respectively. If both the rotation and the translation motion occur simultaneously, the motion of the objective 3016 with respect to the tissue surface 3102 is a superposition of the two motions. The lateral translation of the objective 3016 after it has completed a full rotation (e.g., rotation by approximately 360 degrees around the axis 3004) is called the lateral pitch 3306 of the scanning system 3000. The lateral pitch is indicative of the separation between focal regions associated with the objective 3016 along the lateral scan direction. The length of the lateral pitch can depend on both the angular velocity of rotation of the objective along the rotational scan direction and the speed of translation of the axis 3004 along the lateral scan direction. For example, the length of the lateral pitch 3306 can increase if the speed of translation of the axis 3004 increases or angular velocity of the objective 3016 decreases. The length of the lateral pitch 3306 can decrease if the speed of translation of the axis 3004 decreases or angular velocity of the objective 3016 increases.

In some implementations, the laser beam 3020 can be a pulsed laser beam that includes a series of laser pulses that are separated in space (e.g., due to different time of emission by the laser source). If the objective 3016 is moving (e.g., along the rotational scan direction 3006), adjacent laser pulses can impinge on the laser at different times and/or different locations of the objective. This can result in the adjacent laser pulses being directed to adjacent locations along the treatment path of the focal volume 3204. The separation between the adjacent locations (e.g., along the rotational scan direction 3006) is called the rotational pitch of the scanning system 3000. The length of the rotational pitch can depend on both the angular velocity of rotation of the objective 3016 along the rotational scan direction and temporal separation between adjacent laser pulses, which can be adjusted by changing the repetition rate of the laser. For example, the length of the rotational pitch can increase if the angular velocity of the objective 3016 increases or adjacent pulse separation increases. The length of the rotational pitch can decrease if the angular velocity of the objective 3016 decrease or adjacent pulse separation decreases.

Figure 34:
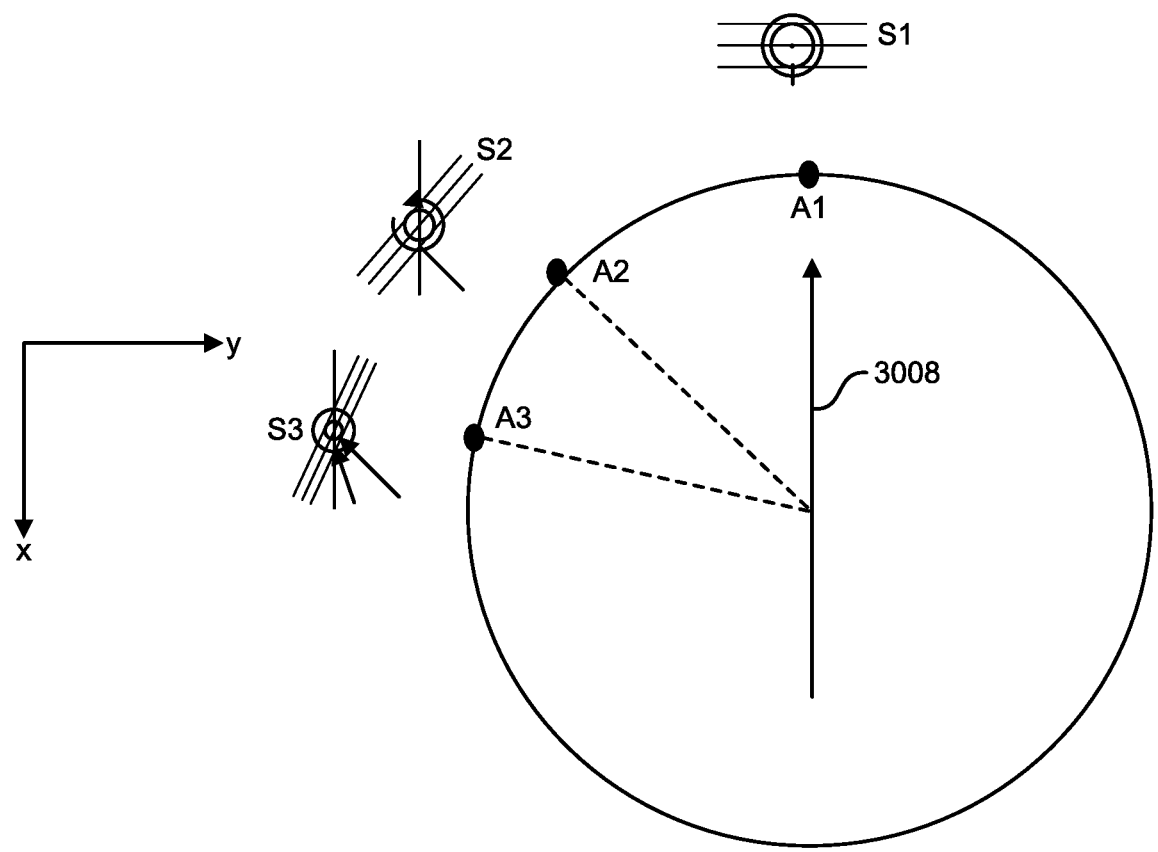
FIG. 34 illustrates variation in lateral pitch based on angular position of an objective in the rotary objective scanning system of FIG. 30.
Figure 35:
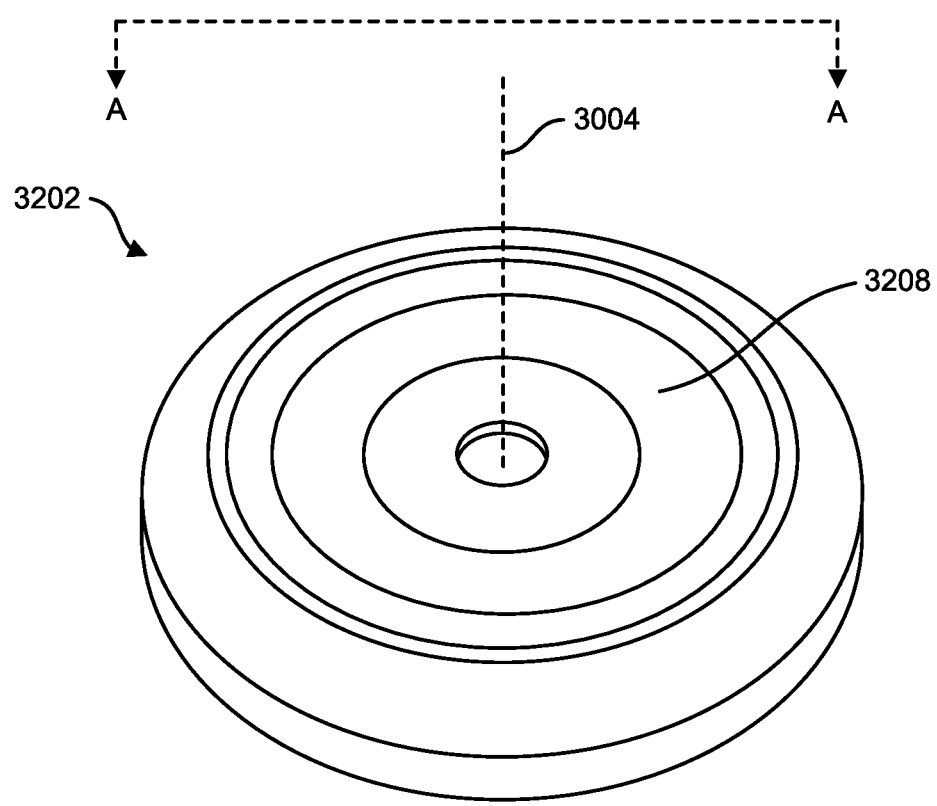
FIG. 35 is an illustration of a contacting surface of the in-plane rotary objective scanning system of FIG. 30.

FIG. 34 illustrates variation in lateral pitch based on angular position of the objective 3016 with respect to the lateral scan direction. At location A1 (located at a first angle with respect to the lateral scan direction 3008), the lateral pitch is S1. At location A2 (located approximately at a second angle with respect to the lateral scan direction 3008), the lateral pitch is S2. At location A3 (located approximately at a third angle with respect to the lateral scan direction 3008), the lateral pitch is S3. The lateral pitch can be inversely proportional to the angular position. For example, if the third angle is larger than the second angle, the lateral pitch S3 is smaller than the lateral pitch S2. If the first angle is smaller than the second angle, the lateral pitch S1 is larger than the lateral pitch S2.

FIG. 34 is an illustration of the contacting surface 3202 from the perspective of the cross section A-A in FIG. 32A. The contacting surface can include an elevated region 3208 that can project towards the surface of the tissue surface 3102. The elevated region 3208 can form, for example, a ring on the contacting surface 3202. The shape of the elevated region 3208 can depend on the path of the objective 3016 relative to the contacting surface 3202 (e.g., path of the objective 3016 along the rotational scan direction 3006). It can be desirable that the objective 3016 remains over the elevated region 3208 as it rotates/travels over the contacting surface. This can be useful because the tissue surface 3102 below the elevated region 3208 is stretched due to the pressure applied by the elevated region 3208. This can allow for efficient transfer of optical energy by the focused beam emanating from the objective 3016 to a focal region in the treatment region of the tissue. The contacting surface 3202 or portions thereof can allow for dissipation of heat from the tissue surface 3102. In one implementation, the contacting surface can be made of sapphire.

Figure 36:
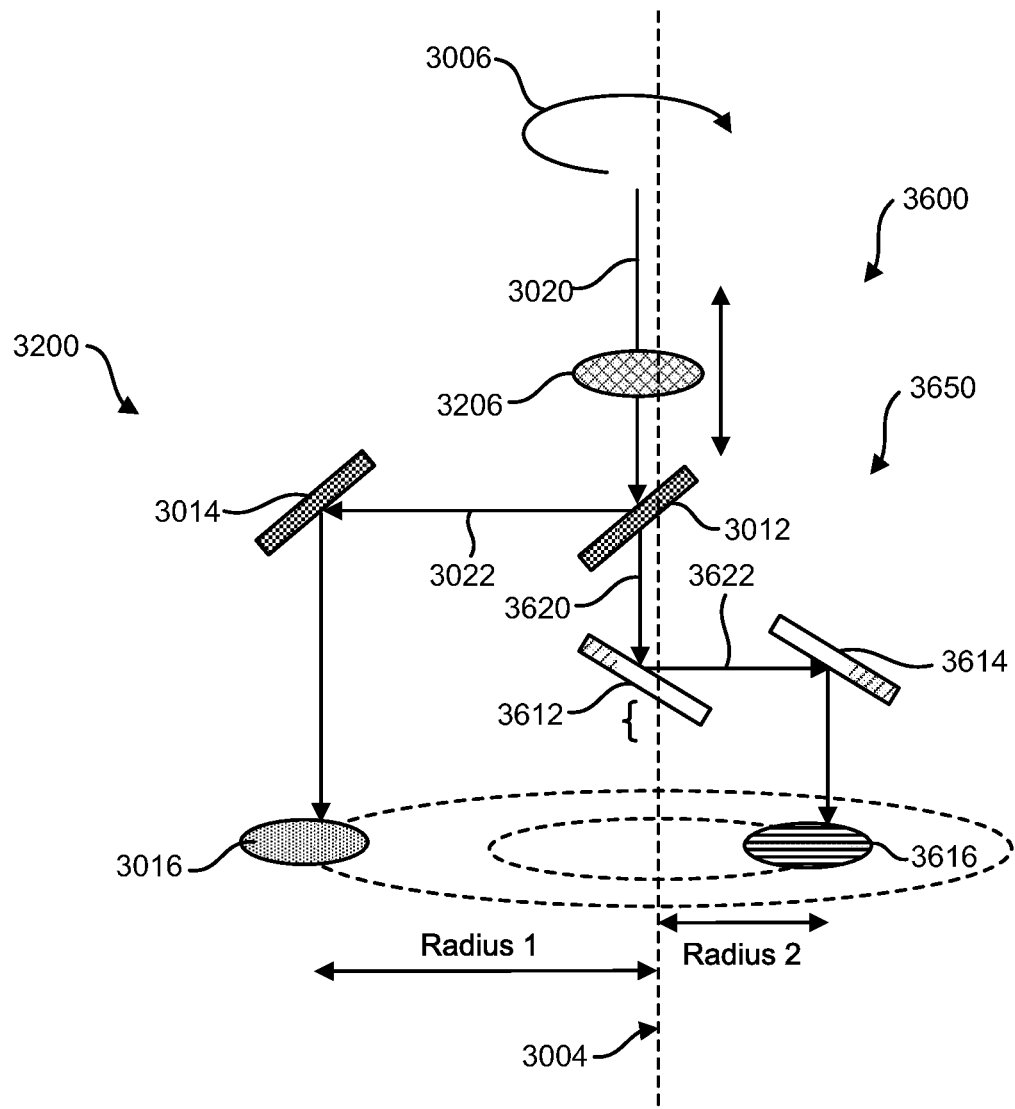
FIG. 36 is a schematic illustration of the arrangement of optical elements in an exemplary in-plane rotary objective scanning system with two objectives.

FIG. 36 is a schematic illustration of the arrangement of optical elements in an exemplary in-plane rotary objective scanning system 3600 that includes two objectives. The two objectives can generate two focal regions from the incident laser beam 3020. The objective scanning system 3600 can include a second optical sub-system 3650 that can optically interact with the first optical sub-system 3200. The second optical sub-system 3650 can include a second optical element 3612, a second mirror 3614, and a second objective 3616. The sub-system 3650 is rigidly coupled to a rotating platform (e.g., rotating platform 3032). The second optical element 3612 can receive a first transmitted beam 3620 transmitted by the first optical element 3012. The first optical element 3012 can be a beam splitter (e.g., 50/50 beam splitter) that can reflect a portion of the incident laser beam 3020 as a first reflected beam 3022 and transmit a portion of the incident laser beam 3020 as the first transmitted beam 3620. The second optical element 3612 can direct a second reflected beam 3622 (e.g., a portion of the first transmitted beam 3620) towards the second mirror 3614 which in turn can direct the laser beam 3622 towards the objective 3616. In one implementation, second optical element 3612 can be a mirror. Alternately, in other implementations, the second optical element 3612 can be a beam splitter that can reflect a first portion of the first transmitted beam 3620 and transmit a second portion of the first transmitted beam 3620. The second objective 3616 can be located at a second radial distance ("Radius 2") from the axis of rotation 3004. The second objective 3616 can rotate along a rotational scan direction. If the objectives 3016 and 1216 are rigidly coupled to the platform 3030, they can rotate along the same rotational scan direction (e.g., 3006). The focal region associated with the second objective 3616 can trace a treatment path. If the axis 3004 remains stationary with respect to the tissue surface 3102, the treatment path associated with the first objective 3016 and the treatment path associated with the second objective 3616 can be concentric (e.g., centered approximately about the axis 3004). The contacting surface (e.g., contacting surface 3202) can include a second elevated region that can project towards the surface of the tissue surface 3102. The second objective 3616 can traverse over the second elevated region as it rotates/travels over the contacting surface In one implementation, the objective system 3600 can independently control the depth of focal volumes associated with objective 3016 and 3616. This can be done, for example, by placing a first lens in the beam path of first reflected beam 3022 and by placing a second lens in the beam path of light beam 3622.

Figure 37:
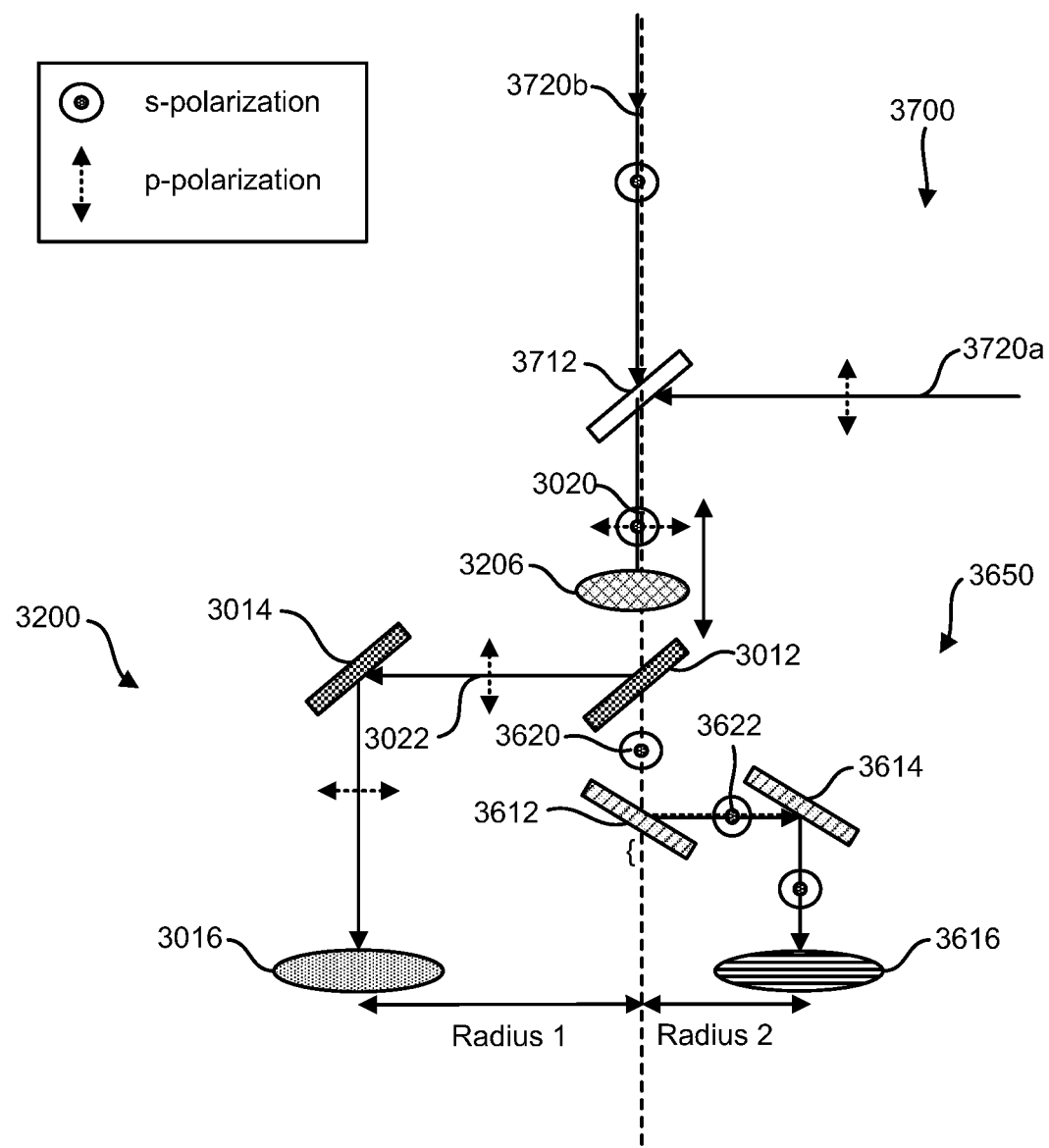
FIG. 37 is a schematic illustration of the arrangement of optical elements in an exemplary polarization based in-plane rotary objective scanning system.

FIG. 37 is a schematic illustration of the arrangement of optical elements in an exemplary polarization based in-plane rotary objective scanning system 3700. The scanning system 3700 includes the first optical sub-system 3200 optically coupled to the second optical sub-system 3650. The scanning system 3700 can include a polarizing beam combiner 3712 that can receive two polarization beams 3720a (e.g., p-polarized) and 3720b (e.g., s-polarized), and can combine them (e.g., superpose them) into the incident laser beam 3020. The first optical element 3012 can be a polarization beam splitter that can direct the first polarization (e.g., p-polarized) to the first optical sub-system 3200, and can direct the second polarization (e.g., s-polarized) to the second optical sub-system 3650. The objectives 3016 and 3616 can focus the first and second polarization laser beam, respectively.

Figure 38:
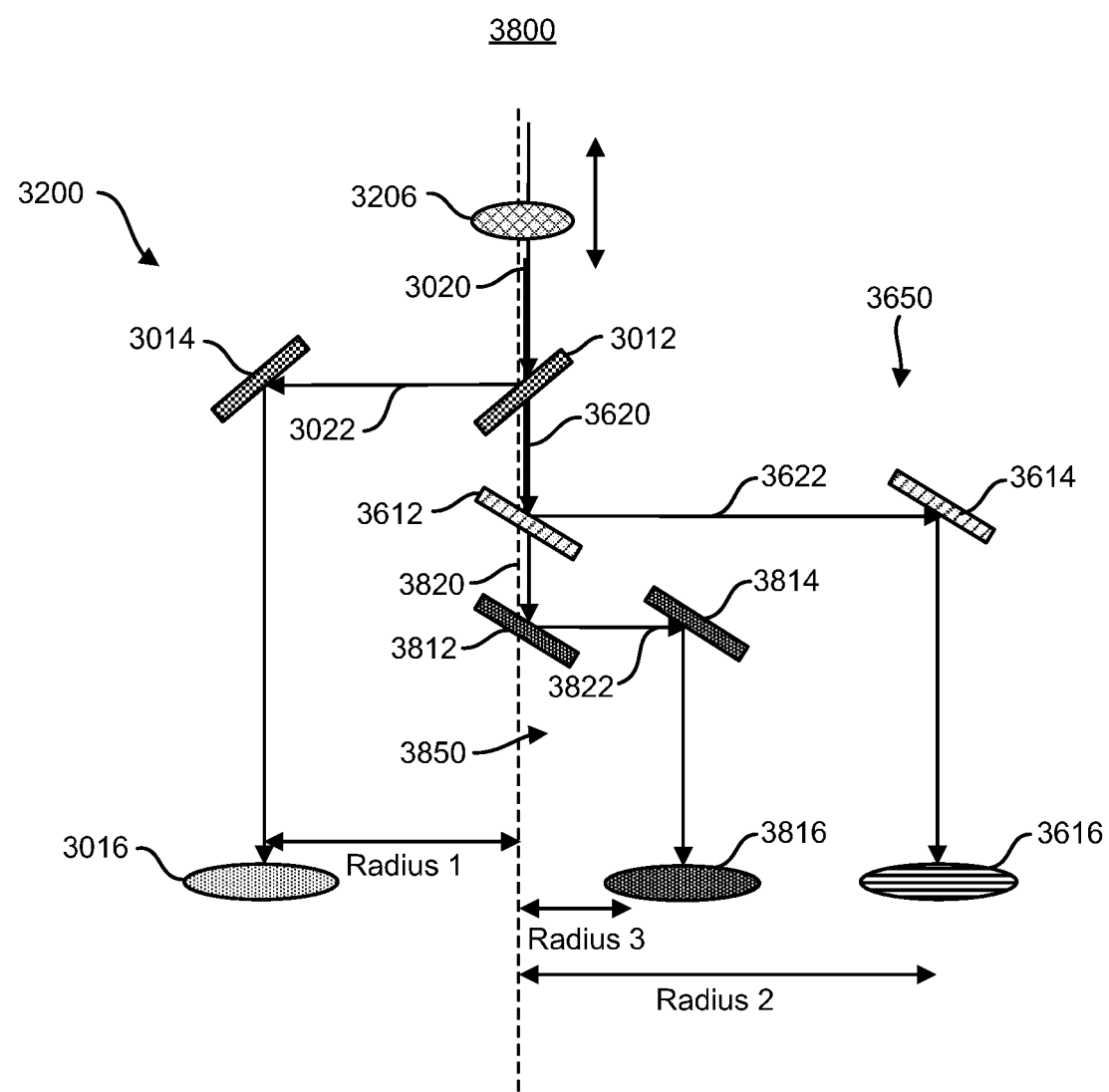
FIG. 38 is a schematic illustration of the arrangement of optical elements in an exemplary in-plane rotary objective scanning system with three objectives.

FIG. 38 is a schematic illustration of the arrangement of optical elements in an exemplary in-plane rotary objective scanning system 3800 that includes three objectives that can generate three focal volumes from the incident laser beam 3020. The objective scanning system 3800 can include a third optical sub-system 3850 that can be optically coupled with the first optical sub-system 3200 and the second optical sub-system 3650.

The third optical sub-system 3850 can include a third optical element 3812, the third mirror 3814 and the third objective 3816. The third optical sub-system 3850 can be rigidly coupled to a rotating platform (e.g., rotating platform 3032). The third objective 3816 can receive a transmitted optical beam 3820 transmitted by the second optical element 3612.

In one implementation, the first and second optical elements 3012 and 3612 can be beam splitters (e.g., a 50/50 beam splitter, a 66/33 beam splitter, etc.) For example, the first optical element 3012 can be a 66/33 beam splitter (e.g. transmit/reflect 66/33 percent of an incident laser beam). The first optical element 3012 can transmit a first transmitted beam 3620 and reflect a first reflected beam 3022. The first reflected beam 3022 is directed to the first optical sub-system. The second optical element 3612 can receive the first transmitted beam 3620. The second optical element can reflect a second reflected beam 3622 and transmit a second transmitted beam 3820. The second reflected beam 3622 is directed to the second optical sub-system 3650. The third optical element 3812 can receive the second transmitted beam 3820 and direct it to the third optical sub-system.

The third objective 3816 can be located at a third radial distance ("Radius 3") from the axis 3004 of rotation. The third objective 3816 can rotate along a rotational scan direction. If the objectives 3016, 3616 and 3816 are rigidly coupled to the platform 3030, they can rotate along the same rotational scan direction (e.g., 3006). The focal region associated with the third objective 3816 can trace a third treatment path. If the axis 3004 remains stationary with respect to the tissue surface 3102, the first, second and third treatment paths can be concentric (e.g., centered approximately about the axis 3004).

In one implementation, the objective scanning system 3800 can independently control the depth of focal volumes associated with objectives 3016, 3616 and 3816. This can be done, for example, by placing a first lens in the beam path of first reflected beam 3022, a second lens in the beam path of light beam 3622, and a third lens in the beam path of light beam 3822.

Transverse Rotary Objective Scanning System

Figures 39A, 39B:
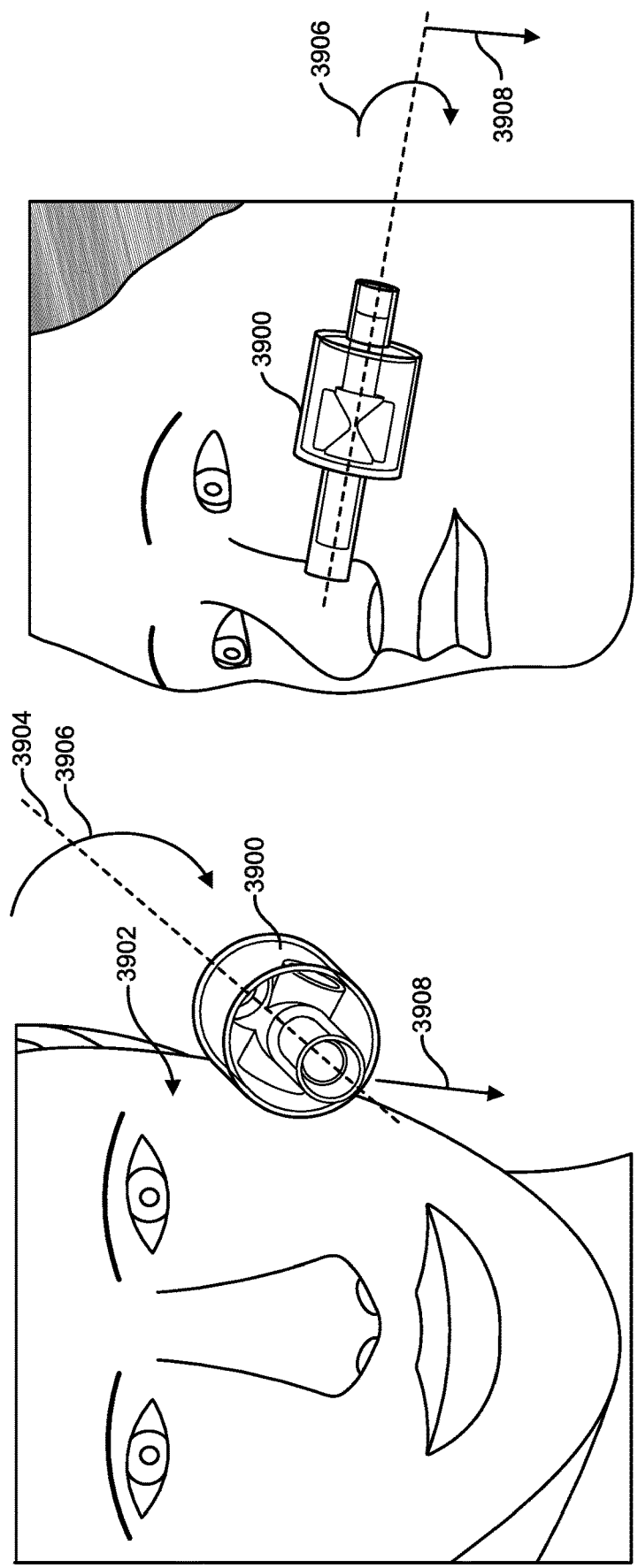
FIG. 39A is a perspective view of a transverse rotary objective scanning system over a treatment region.
FIG. 39B is another perspective view of a transverse rotary objective scanning system over the treatment region.

FIG. 39A is a perspective view of a transverse rotary objective scanning system 3900 over a treatment region 3902. The objective scanning system 3900 can rotate about an axis 3904 along a rotational scan direction 3906. Additionally, the axis 3904 can lateral translate along a lateral scan direction 3908. FIG. 39B is another perspective view of a transverse rotary objective scanning system over the treatment region 3902.

Figure 40A:
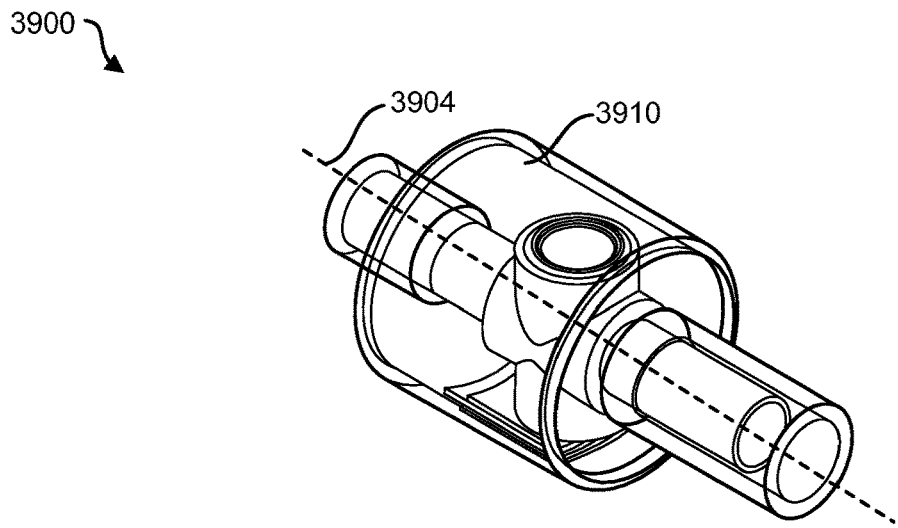
FIG. 40A is a perspective view of an exemplary transverse rotary objective scanning system.
Figure 40B:
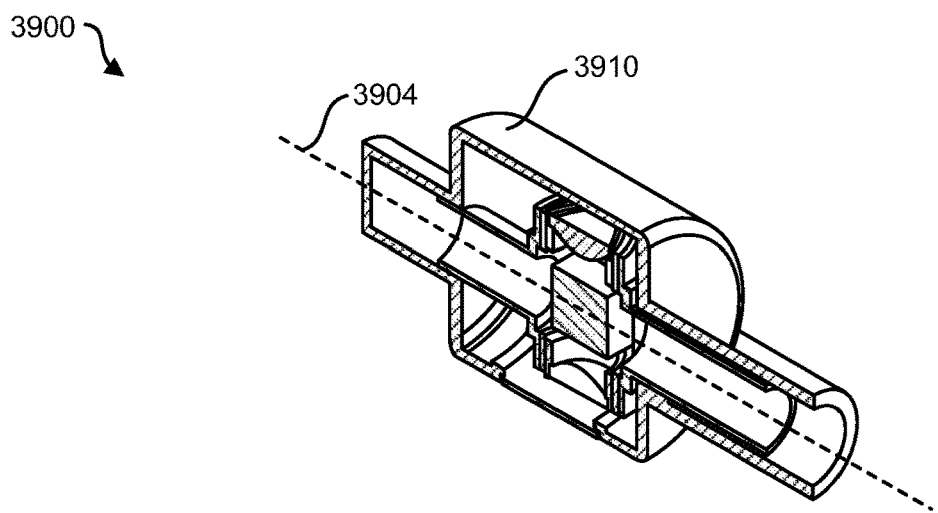
FIG. 40B is an illustration of the optical elements of the transverse rotary objective scanning system of FIG. 40A.
Figure 40C:
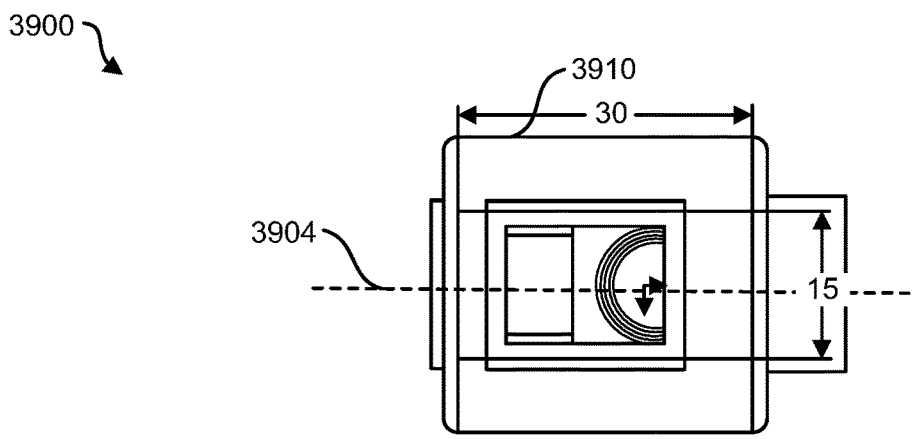
FIG. 40C is a side view of the transverse rotary objective scanning system of FIG. 40A.

FIG. 40A is a perspective view of an exemplary transverse rotary objective scanning system 3900. The scanning system 3900 can include a housing 3910 that can enclose various optical elements. The housing 3910 can have a cylindrical shape that can allow the scanning system to roll on the surface of the treatment region 3902. FIG. 40B is an illustration of the cross-section of the transverse rotary objective scanning system 3900. FIG. 40C is a side view of the transverse rotary objective scanning system 3900.

Figure 41:
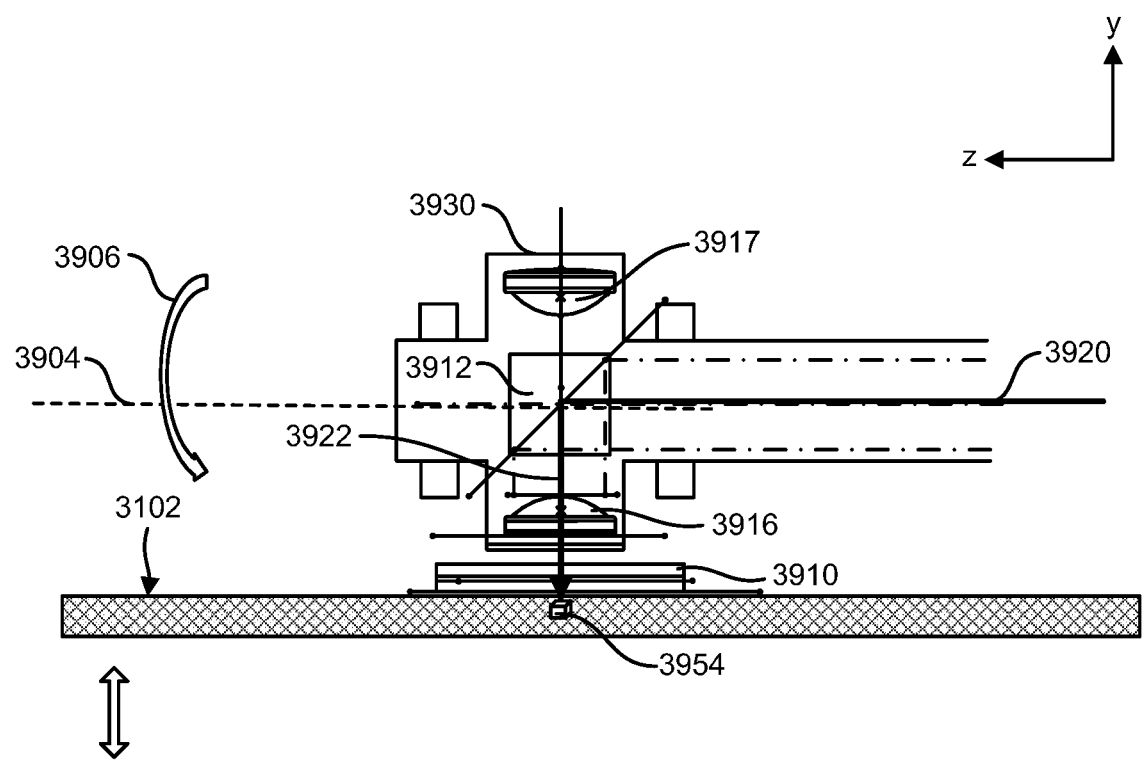
FIG. 41 is a side view of the transverse rotary objective scanning system of FIG. 40A located over a tissue surface.

FIG. 41 is a side view of the transverse rotary objective scanning system 3900 located over a tissue surface 3102. The scanning system includes a rotating platform 3930 that can rotate relative to the housing 3910. The rotating platform 3930 can be rigidly coupled to a first optical element 3912 (e.g., beam splitter, mirror, etc.), a first objective 3916 and a second objective 3917 that are rigidly coupled to the rotating platform 3930, and can rotate with the rotating platform 3930. A laser beam 3920 can impinge on the first optical element 3912 that can reflect a first reflected beam 3922. The first reflected beam 3922 can be directed towards the objective 3916. The objective 3916 can focus the first reflected beam 3922 to a focal volume 3954 in the treatment region of the tissue surface 3102.

It can be desirable that the scanning system 3900 remain stable (e.g., does not wobble) as rotating platform 3930 rotates about the axis 3904. This stability can be achieved, for example, by designing the scanning system 3900 such that its center of mass remains close to the axis 3904 during rotation. This can be done, for example, by including a second objective 3917 that is rigidly coupled to the rotating platform 3930. The radial locations of the second objective 3917 can be determined based on the location of the center of mass of the scanning system 3900 prior to coupling with the second objective 3917.

The rotating platform 3930 can be translated along the axis 3904 (e.g., by an actuator). This can allow the focal volume 3954 to scan a lateral treatment path in the tissue surface 3102. The objective 3916 can move along a radial direction with respect to the axis 3904. This can allow for varying the depth of the focal volume 3954. A portion of the housing 3910 (also referred to as contacting surface) can separate the objective 3916 and the tissue surface 3102. The housing can press against the surface of the tissue surface 3102 and allow for efficient transfer of optical energy through the first reflected beam 3922. The housing 3910 can also cool the surface of the tissue surface 3102 by dissipating heat. The housing 3910 can include a curved surface. For example, the portion of the housing in contact with treatment region (e.g., contacting surface) can be curved.

Figure 42A:
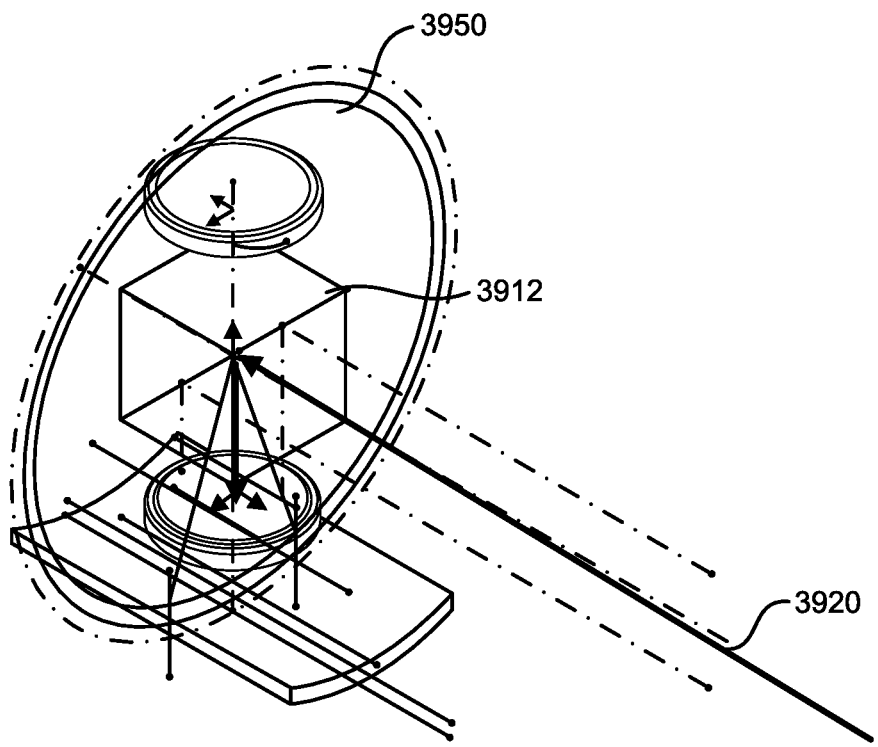
FIG. 42A is a perspective view of the arrangement of objectives in the transverse rotary objective scanning system of FIG. 40A.
Figure 42B:
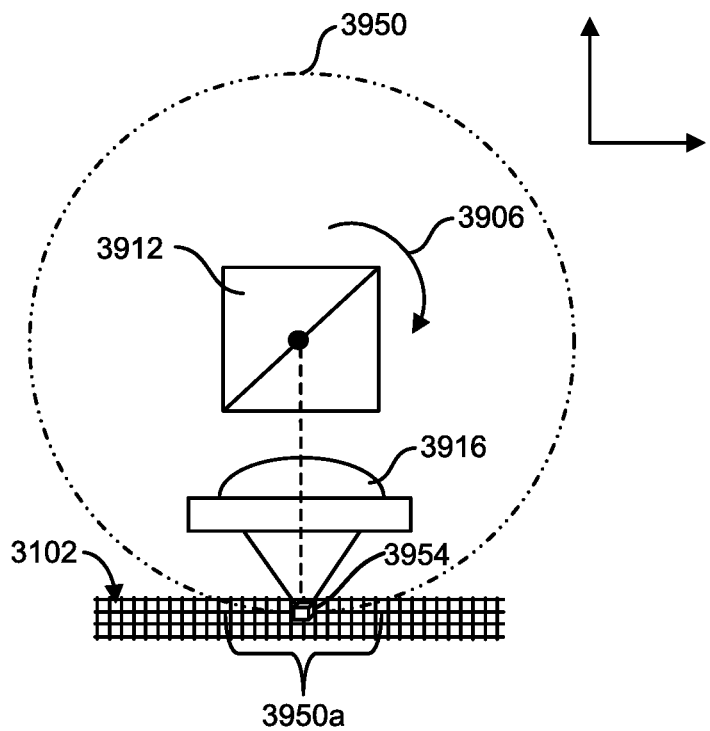
FIG. 42B is a schematic illustration of a scan path associated with an objective of the transverse rotary objective scanning system of FIG. 42A.

FIG. 42A is a perspective view of the arrangement of optical elements in the transverse rotary objective scanning system 3900. The focal volume 3954 associated with the objective 3916 traverses along a circular scan path 3950 (e.g., parallel to the x-y plane). FIG. 42B is a schematic illustration of a scan path associated with the first objective 3916. The circular scan path 3950 may overlap with the tissue surface 3102 for a portion 3950a of the circular scan path 3950.

Figure 43:
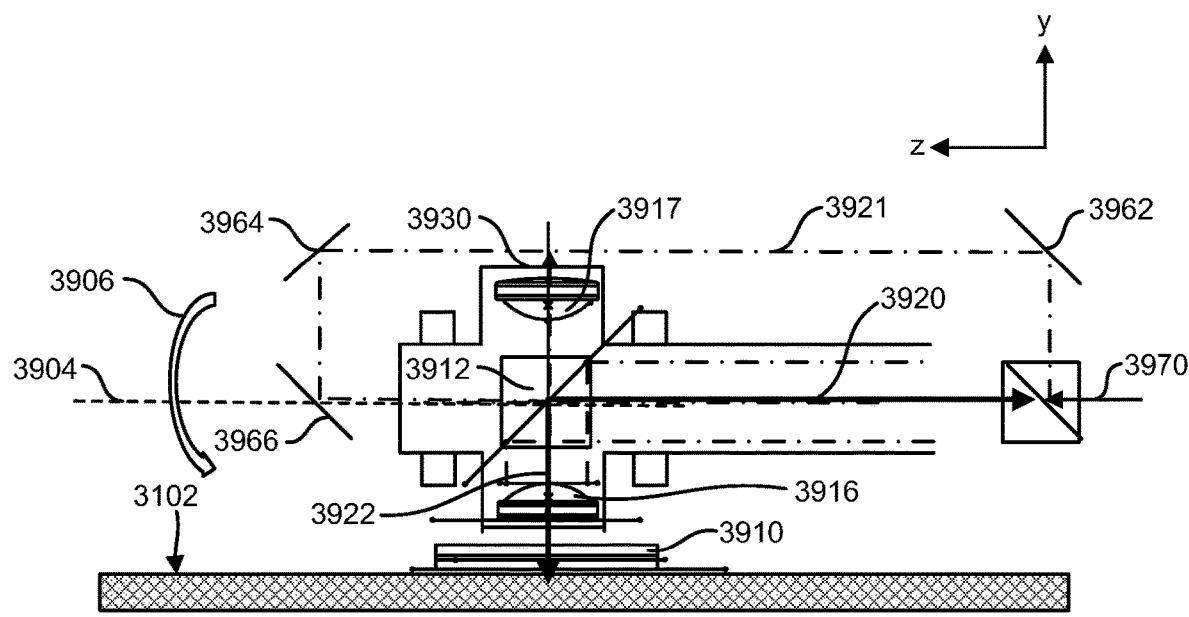
FIG. 43 is a side view of another exemplary transverse rotary objective scanning system.

FIG. 43 is a perspective view of an exemplary transverse rotary objective scanning system 4300. The objective scanning system 4300 includes a beam splitter 3960 upstream from the first optical element 3912. The beam splitter 3960 can receive an incident beam 3970, transmit a portion of the incident beam 3970 as a transmitted beam 3920, and reflect a portion of the incident beam 3970 as a reflected beam 3921. The reflected beam can be redirected to the first optical element 3912 via a separate optical path comprising mirrors 3962, 3964 and 3966. The first optical element 3912 can be a beam splitter that can direct the transmitted beam 3920 towards the first objective 3916, and direct the reflected beam 3921 towards the second objective 3917. As a result, the scanning system 4300 can generate two focal volumes (associated with objectives 3916 and 3917). The two focal volumes can rotate along the circular scan path 3950. This can expedite the treatment of the tissue surface 3102. The radial locations of the first objective 3916 and the second objective 3917 can be determined based on their masses. This can be done to ensure that the transverse rotary objective scanning system 4300 remains stable when the rotating platform 3930 rotates. In one implementation, first objective 3916 and the second objective 3917 can have similar masses and can be equidistant from the axis 3904.

Example parameters according to some embodiments of objective beam scanners are disclosed below in Table 3.

TABLE 3

Objective Scanner Example Parameter Values

| Parameter | Typical Minimum | Nominal | Typical Maximum |
|---|---|---|---|
| No. of Objectives (—) | 1 | 1 | 10 |
| Radius from Center of Objective to Rotational Axis (mm) | 0.5 | 5 | 50 |
| Rotating Speed of Objective(s) (RPM) | 50 | 2000 | 10000 |
| Translation Distance of Rotating Axis (mm) | 1 | 10 | 100 |
| Translating Speed of Rotating Axis (mm/min) | 1 | 10 | 1000 |
| Translational Pitch (μm) | 1 | 25 | 1000 |
| Rotational Pitch (μm) | 1 | 25 | 1000 |
| Numerical Aperture of Objective (—) | 0.3 | 0.5 | 0.9 |
| Focal Region Depth Beneath Skin Surface (μm) | 20 | 200 | 2000 |
| Average Power of Laser (W) | 0.5 | 10 | 30 |

TABLE 3-continued

Objective Scanner Example Parameter Values

| Parameter | Typical Minimum | Nominal | Typical Maximum |
|---|---|---|---|
| Repetition Rate of Laser (Hz) | 1 | 20000 | C.W. |
| Pulse Duration of Laser (nS) | <1 | 100 | >1000000 |
| Energy per Pulse (mJ) | 0.1 | 2 | >100 |
| Wavelength (nm) | 300 | 1064 | 3000 |

Systems and methods for scanning an EMR beam are explained above with reference to specific applications (e.g., dermatological treatments). While the beam scanning systems and methods described herein are expected to speed and benefit treatment of currently intractable dermatological conditions, the beam scanning systems and methods are generally well-suited for other applications, specifically those that require a high NA beam.

Methods of treating various skin conditions, such as for cosmetic purposes, can be carried out using the systems described herein. It is understood that although such methods can be conducted by a physician, non-physicians, such as aestheticians and other suitably trained personnel may use the systems described herein to treat various skin conditions with and without the supervision of a physician.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. An electromagnetic beam scanning system, comprising:
   a motor configured to generate a rotational movement,
   a reciprocating mechanism operatively coupled with the motor and configured to convert the rotational movement to a reciprocating movement including a plurality of strokes along a first scanned axis, wherein the reciprocating movement has a constant speed over at least a portion of a stroke of the plurality of strokes,
   a focus optic operatively coupled to the reciprocating mechanism such that the focus optic moves according to the reciprocating movement of the reciprocating mechanism, the focus optic configured to focus an electromagnetic radiation (EMR) beam incident upon the focus optic to a focal region along an optical axis substantially orthogonal to the first scanned axis, and
   an intermittent mechanism operatively coupled with the reciprocating mechanism, configured to introduce an intermittent movement that translates along a second scanned axis which is substantially orthogonal to the first scanned axis, and
   wherein the focus optic is operable coupled to the intermittent mechanism such that the focus optic moves according to the intermittent movement.

2. The system of claim 1, wherein the constant speed is within 50% of a desired constant speed and the portion of the stroke is at least 10% of the stroke.

3. The system of claim 1, further comprising:
   an electromagnetic radiation source configured to generate the EMR beam, and an optical system configured to direct the EMR beam incident upon the focus optic.

4. The system of claim 3, wherein at least one element of the optical system moves according to the reciprocating movement.

5. The system of claim 3, wherein the EMR source is configured to operate in a pulsed mode according to a predetermined repetition rate, wherein a relationship between the repetition rate of the EMR source and the constant speed of the reciprocating movement determines a nominal pitch between sequential pulsed focuses along the first scanned axis.

6. The system of claim 1, wherein the intermittent mechanism is configured to introduce the intermittent movement according to a position of the reciprocating movement.

7. The system of claim 6, wherein the intermittent movement is introduced when the reciprocating movement is generally at a position corresponding to at least one of: a beginning of the stroke, a middle of the stroke, and an end of the stroke.

8. The system of claim 1, further comprising:
a housing disposed between the focus optic and the focal region along the optical axis that is configured to contact a surface of a target tissue via a contacting surface; wherein the focal region is located down beam of the surface of the target tissue.

9. The system of claim 8, wherein the contacting surface is configured to cool the target tissue.

10. The system of claim 8, wherein the housing includes one or more of a pressure sensor, a contact sensor, and a temperature sensor.

11. A method of electromagnetic beam scanning, comprising:
generating a rotational movement,
converting the generated rotational movement into a reciprocating movement including a plurality of strokes along a first scanned axis, wherein the reciprocating movement has a constant speed over at least a portion of a stroke of the plurality of strokes,
moving a focus optic according to the reciprocating movement, wherein the focus optic is configured to focus an electromagnetic radiation (EMR) beam incident upon the focus optic to a focal region along an optical axis substantially orthogonal to the first scanned axis,
introducing an intermittent movement that translates along a second scanned axis, and that is substantially orthogonal to the first scanned axis, and
moving the focus optic according to the intermittent movement.

12. The method of claim 11, wherein the constant speed is within 50% of a desired constant speed and the portion of the stroke is at least 10% of the stroke.

13. The method of claim 12, further comprising:
generating the EMR beam, and
directing, using an optical system, the EMR beam incident upon the focus optic.

14. The method of claim 13, further comprising
moving at least one element of the optical system according to the reciprocating movement.

15. The method of claim 13, further comprising:
pulsing the EMR beam according to a predetermined repetition rate, wherein a relationship between the repetition rate and the constant speed determines a nominal pitch between sequential pulsed laser focuses along the first scanned axis.

16. The method of claim 11, wherein the intermittent movement is introduced according to a position of the reciprocating movement.

17. The method of claim 16, wherein the intermittent movement is introduced when the reciprocating movement is generally at a position corresponding to at least one of: a beginning of the stroke, a middle of the stroke, and an end of the stroke.

18. The method of claim 11, further comprising:
contacting a surface of a target tissue between the focus optic and the focal region along the optical axis with a contacting surface of a housing, wherein the focal region is located down beam of the surface of the target tissue.

19. The method of claim 18, further comprising cooling the target tissue using the contacting surface.

20. The method of claim 19, further comprising sensing, using a sensor located within the housing, one or more variables of the target tissue, comprising: a pressure, a contact between the contacting surface and the target tissue, and a temperature.

* * * * *